US 10,549,053 B2

(12) United States Patent
Armitstead et al.

(10) Patent No.: US 10,549,053 B2
(45) Date of Patent: *Feb. 4, 2020

(54) AUTOMATED CONTROL FOR DETECTION OF FLOW LIMITATION

(71) Applicant: ResMed Limited, Bella Vista (AU)

(72) Inventors: Jeffrey Peter Armitstead, Sydney (AU); Peter Edward Bateman, Sydney (AU); David John Bassin, Sydney (AU)

(73) Assignee: ResMed Pty Ltd (AU)

( * ) Notice: Subject to any disclaimer, the term of this patent is extended or adjusted under 35 U.S.C. 154(b) by 939 days.

This patent is subject to a terminal disclaimer.

(21) Appl. No.: 15/151,641

(22) Filed: May 11, 2016

(65) Prior Publication Data

US 2016/0250428 A1  Sep. 1, 2016

Related U.S. Application Data

(63) Continuation of application No. 12/599,715, filed as application No. PCT/AU2008/000647 on May 9, 2008, now Pat. No. 9,358,353.

(Continued)

(30) Foreign Application Priority Data

May 11, 2007   (AU) ................................ 2007902561

(51) Int. Cl.
*A61M 16/00*     (2006.01)

(52) U.S. Cl.
CPC .... *A61M 16/0069* (2014.02); *A61M 16/0003* (2014.02); *A61M 2016/003* (2013.01);
(Continued)

(58) Field of Classification Search
CPC .......... A61M 16/0051; A61M 16/0069; A61M 16/0003; A61M 2205/50;
(Continued)

(56) References Cited

U.S. PATENT DOCUMENTS 4,944,310 A   7/1990 Sullivan
5,199,424 A   4/1993 Sullivan et al.
(Continued)

FOREIGN PATENT DOCUMENTS

CN   1886168 A   12/2006
EP   1205203 A    5/2002
(Continued)

OTHER PUBLICATIONS

Chinese Office Action issued in corresponding CN application No. 201610756348.2 dated Mar. 16, 2018.
(Continued)

*Primary Examiner* — Timothy A Stanis
(74) *Attorney, Agent, or Firm* — Botos Churchill IP Law LLP

(57) ABSTRACT

A respiratory flow limitation detection device, which can include an airway pressure treatment generator, determines a flow limitation measure 506 based one or more shape indices for detecting partial obstruction and a measure of a patient's ventilation or respiratory duty cycle. The shape indices may be based on function(s) that ascertain the likelihood of the presence of M-shaped breathing patterns and/or chair-shaped breathing patterns. The measure of ventilation may be based on analysis of current and prior tidal volumes to detect a less than normal patient ventilation. The duty cycle measure may be a ratio of current and prior measures of inspiratory time to respiratory cycle time to detect an increase in the patient's inspiratory cycle time relative to the respiratory cycle time. A pressure setting
(Continued)

based on the flow limitation may then be used to adjust the treatment pressure to ameliorate the patient's detected flow limitation condition.

40 Claims, 39 Drawing Sheets

Related U.S. Application Data

(60) Provisional application No. 60/965,172, filed on Aug. 17, 2007.

(52) U.S. Cl.
CPC ............ *A61M 2016/0027* (2013.01); *A61M 2016/0036* (2013.01); *A61M 2205/3327* (2013.01); *A61M 2205/3334* (2013.01); *A61M 2205/50* (2013.01); *A61M 2230/40* (2013.01)

(58) Field of Classification Search
CPC .. A61M 2205/3334; A61M 2205/3327; A61M 2230/40; A61M 2016/003
See application file for complete search history.

(56) References Cited

U.S. PATENT DOCUMENTS

| | | | |
|---|---|---|---|
| 5,245,995 | A | 9/1993 | Sullivan et al. |
| 5,458,137 | A | 10/1995 | Axe et al. |
| 5,490,502 | A | 2/1996 | Rapoport et al. |
| 5,549,106 | A | 8/1996 | Gruenke et al. |
| 5,645,053 | A | 7/1997 | Remmers et al. |
| 5,704,345 | A | 1/1998 | Berthon-Jones |
| 5,740,795 | A | 4/1998 | Brydon |
| 5,794,615 | A | 8/1998 | Estes |
| 5,803,066 | A | 9/1998 | Rapoport et al. |
| 6,015,388 | A | 1/2000 | Sackner et al. |
| 6,099,481 | A | 8/2000 | Daniels et al. |
| 6,332,463 | B1 | 12/2001 | Farrugia et al. |
| 6,336,454 | B1 | 1/2002 | Farrell et al. |
| 6,532,957 | B2 | 3/2003 | Berthon-Jones |
| 6,739,335 | B1 | 5/2004 | Rapport et al. |
| 6,793,629 | B2 | 9/2004 | Rapoport et al. |
| 6,988,498 | B2 | 1/2006 | Berthon-Jones et al. |
| 7,128,069 | B2 | 10/2006 | Farrugia et al. |
| 7,225,809 | B1 | 6/2007 | Bowen et al. |
| 2001/0000346 | A1 | 4/2001 | Ruton et al. |
| 2002/0088465 | A1 | 7/2002 | Hill |
| 2004/0111040 | A1 | 6/2004 | Ni et al. |
| 2004/0123866 | A1 | 7/2004 | Berthon-Jones |
| 2005/0061319 | A1 | 3/2005 | Hartley et al. |
| 2006/0032503 | A1 | 2/2006 | Berthon-Jones et al. |
| 2006/0060198 | A1 | 3/2006 | Aylsworth et al. |
| 2006/0196508 | A1 | 9/2006 | Chalvignac |

FOREIGN PATENT DOCUMENTS

| | | | |
|---|---|---|---|
| EP | 1393767 | A | 3/2004 |
| EP | 1488743 | A2 | 12/2004 |
| JP | 2001-513387 | A | 9/2001 |
| JP | 2002-505924 | A | 2/2002 |
| JP | 2002-516159 | A | 6/2002 |
| JP | 2003-516825 | A | 5/2003 |
| JP | 2004506499 | A | 3/2004 |
| JP | 2004-526470 | A | 9/2004 |
| JP | 2004-529797 | A | 9/2004 |
| JP | 2004-533483 | A | 11/2004 |
| JP | 2005505347 | A | 2/2005 |
| WO | 9841146 | A1 | 9/1998 |
| WO | 0218002 | A1 | 3/2002 |
| WO | 2002047747 | A1 | 6/2002 |
| WO | 03030804 | A2 | 4/2003 |
| WO | 2004049930 | A2 | 6/2004 |
| WO | 2004067070 | A1 | 8/2004 |
| WO | 2004112680 | A2 | 12/2004 |
| WO | 2005051470 | A1 | 6/2005 |
| WO | 2005077447 | A1 | 8/2005 |
| WO | 2006047826 | A1 | 5/2006 |
| WO | 2006079152 | A1 | 8/2006 |
| WO | 2006133493 | A1 | 12/2006 |
| WO | 2007101297 | A1 | 9/2007 |

OTHER PUBLICATIONS

EP Search Report dated Feb. 1, 2018 to EP Patent Application No. 08733465.2.
Extended European Search Report issued in corresponding EP application No. 08733465.2 dated Jun. 1, 2018.
JP Office Action issued in corresponding JP application No. 2017-190847 dated Sep. 11, 2018.
Clark et al. (1998) Assesment of Inspiratory Flow Limitation Invasively and Non-invasively during Sleep. American Journal of Respiratory Critical Care Medicine, V158 pp. 713-722.
Clark T.J.H., 'Inspiratory Obstruction', British Medical Journal, 1970 V3, pp. 682-684.
Clark, et al. Assessment of Inspiratory Flow Limitation Invasively and Noninvasively during Sleep, Am J. Respir. Crit. Care Med, vol. 158, pp. 713-722, 1998.
Frey et al ., J. Applied Physiology, 91; 1687-1693 (2001).
Frey et al. (2001). Analysis of the Harmonic Content of the Tidal Flow Waveforms in Infants. J. Applied Physiology, V91, p. 1687-1693.
International Search Report, PCT/AU2008/000647 dated Aug. 13, 2008.
Kirkness et al. (2006). Upper Airway Obstruction in Snoring and Upper Airway Resistance Syndrome. Sleep Apnea, Prog Respir Res. V35, pp. 79-89.
Lofuso et al, Chest Original Research: Sleep Medicine, 343-349 (2006).
Marcus et al. (1999). Response to Inspiratory Resistive Loading During Sleep in Normal Children and Children with Obstructive Apnea. J. Applied Physiology, V87, p. 1448-1454.
Nolan et al, Eur. Respir. J., 28(1); 159-164 (2006).
Pellegrino R. et. al., 'Interpretative strategies for lung function tests', European Respiratory Journal, 2005, V26, pp. 948-968.
Rigau et al, Original Research: Sleep Medicine, ResMed, 350-361 (2006).
Shin et al., Sleep, 21(8); 817-828 (1998).

AUTOMATED CONTROL FOR DETECTION OF FLOW LIMITATION

CROSS-REFERENCES TO RELATED APPLICATIONS

This application is a continuation of U.S. patent application Ser. No. 12/599,715, filed May 10, 2011, which is a national phase entry under 35 U.S.C. § 371 of International Application No. PCT/AU08/00647, filed May 9, 2008, published in English, which claims priority from U.S. Provisional Patent Application No. 60/965,172 filed on Aug. 17, 2007 and Australian Provisional Patent Application No. 2007902561 filed May 11, 2007, all of which are incorporated herein by reference.

FIELD OF THE INVENTION

The presented technology relates to methods and apparatus for the detection, diagnosis and/or treatment of respiratory conditions such as the conditions related to sleep apnea hypopnea syndrome (OSAHS) or obstructive sleep apnea (OSA).

BACKGROUND OF THE INVENTION

As described by Sullivan & Lynch in U.S. Pat. No. 5,199,424, issued on Apr. 6, 1993, the application of continuous positive airway pressure (CPAP) has been used as a means of treating the occurrence of obstructive sleep apnea. The patient is connected to a positive pressure air supply by means of a nose mask or nasal prongs. The air supply breathed by the patient is slightly greater than atmospheric pressure. It has been found that the application of continuous positive airway pressure provides what can be described as a "pneumatic splint", supporting and stabilizing the upper airway and thus eliminating the occurrence of upper airway occlusions. It is effective in eliminating both snoring and obstructive sleep apnea and in many cases, is effective in treating central and mixed apnea.

In U.S. Pat. No. 5,549,106 to Gruenke, issued on Aug. 27, 1996, an apparatus is disclosed that is intended for facilitating the respiration of a patient for treating mixed and obstructive sleep apnea. The device increases nasal air pressure delivered to the patient's respiratory passages just prior to inhalation and by subsequently decreasing the pressure to ease exhalation effort.

In U.S. Pat. No. 5,245,995 Sullivan discusses how snoring and abnormal breathing patterns can be detected by inspiration and expiration pressure measurements while sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to, ideally, subvert the occurrence of the obstructive episodes and the other forms of breathing disorder.

As described by Berthon-Jones in U.S. Pat. No. 5,704,345, issued on Jan. 6, 1998, various techniques are known for sensing and detecting abnormal breathing patterns indicative of obstructed breathing. Berthon-Jones describes methods based on detecting events such as apnea, snoring, and respiratory flow flattening. Treatment pressure may be automatically adjusted in response to the detected conditions.

As described by Wickham in International Patent Application PCT/AU01/01948 (Publication No. WO0218002), a flow flattening determination may be further based upon different weighting factors. The weighing factors are applied to sections of the airflow to improve sensitivity to various types of respiration obstructions.

Other methods for detecting obstruction have also been used. For example, in U.S. Pat. Nos. 5,490,502 and 5,803,066, Rapport discloses a method and apparatus for optimizing the controlled positive pressure to minimize the flow of air from a flow generator while attempting to ensure that flow limitation in the patient's airway does not occur. Controlled positive pressure to the airway of a patient is adjusted by detecting flow limitation from the shape of an inspiratory flow waveform. The pressure setting is raised, lowered or maintained depending on whether flow limitation has been detected and on the previous actions taken by the system.

In U.S. Pat. No. 5,645,053, Remmers describes a system for automatically and continuously regulating the level of nasal pressure to an optimal value during OSA (Obstructive Sleep Apnea) treatment. Parameters related to the shape of a time profile of inspiratory flow are determined including a degree of roundness and flatness of the inspiratory profile. OSA therapy is then implemented by automatically re-evaluating an applied pressure and continually searching for a minimum pressure required to adequately distend a patient's pharyngeal airway.

Despite the availability of such devices for treating OSA, some sleep obstructive events may still go untreated with the use of some devices. Thus, new methods of automated detection and treatment of obstructive events may be desirable.

SUMMARY OF THE INVENTION

In an aspect of the present technology, apparatus and methods are provided with improved automatic detection and/or automatic treatment of sleep disordered breathing or flow limitation.

In another aspect of the present technology, improved detection and/or treatment of flow waveforms indicative of partial obstruction is provided.

In still another aspect of the present technology, apparatus and methods are provided for a more rapid response to indications of partial obstruction or flow limitation.

In still another aspect of the present technology, apparatus and methods are provided for qualifying a measure of flow limitation or partial obstruction, such as a flow limited waveform or shape index thereof, by a measured or detected secondary condition of the airway to more accurately detect obstructive events.

Aspects of the present technology involve methods for detecting flow limitation that may include determining a measure of respiratory flow, determining a shape index indicative of a pattern of flow limitation from the measure of respiratory flow, determining a ventilation measure or a breath duty cycle measure from the measure of respiratory flow and deriving a flow limitation measure as a function of the determined shape index and either or both of the determined ventilation measure and the duty cycle measure.

In certain embodiments, the shape index may be an index of flattening, an index of "M" shaping, an index of a chair shaping and/or roundness etc. or other index that may be indicative of a partial obstruction. The ventilation measure may be a tidal volume measure such as a ratio of a current tidal volume to a prior tidal volume. The breath duty cycle measure may be a ratio such as a ratio of a current breath inspiration time to breath cycle time ratio and a prior average breath inspiration time to breath cycle time ratio.

The methods may be implemented by flow limitation detectors and/or by flow limitation pressure treatment devices. For example, the methods may be implemented to adjust treatment pressure of a pressure treatment device, such as by increasing pressure as a condition of the shape index being indicative of the presence of an M shape breath in the respiratory airflow and the ventilation measure decreasing sufficiently to be indicative of less than normal ventilation. Optionally, the treatment pressure value may be adjusted or increased as a condition of the shape index being indicative of the presence of an M shape breath in the respiratory airflow and an increase of the duty cycle measure.

In one embodiment of the technology, an apparatus to detect flow limitation may include a patient interface to carry a flow of breathable gas, a flow sensor coupled with the patient interface to generate a flow signal representing flow of the breathable gas through the patient interface, and a controller coupled with the flow sensor to process the flow signal, where the controller is configured to control a method of detection to derive the flow limitation measure based on the shape index and either or both of the ventilation measure and the breath duty cycle measure. The apparatus may further include a flow generator coupled with the controller and the patient interface, so that the controller can be configured to calculate a pressure request as a function of the flow limitation measure, and set the flow generator in accordance with the pressure request such as the adjustments described herein.

In one embodiment of the technology, a system for the detection of flow limitation may include an interface means to carry a flow of breathable gas, a flow measuring means coupled with the interface means for generating a flow signal representing flow of the breathable gas through the interface means, and a processing means coupled with the flow measuring means for processing the flow signal, where the processing means is configured for processing a method of detection to derive the flow limitation measure based on the shape index and either the ventilation measure or breath duty cycle measure. The system may further include a flow means, coupled with the processing means and the interface means, for generating a controlled flow of breathable gas through the interface means such that the processing means may be configured for calculating a pressure request as a function of the flow limitation measure, and setting the flow generator in accordance with the pressure request.

In another embodiment, the technology may be an information-bearing medium having processor-readable information thereon, such that the processor-readable information can control an apparatus for detecting respiratory flow limitation. The processor-readable information may comprise control instructions for determining a measure of respiratory flow, determining a shape index indicative of a pattern of flow limitation from the measure of respiratory flow, determining a ventilation measure and/or breath duty cycle measure from the measure of respiratory flow, and deriving a flow limitation measure as a function of the determined shape index and either or both of the determined ventilation measure and breath duty cycle measure. The processor-readable information may further comprise instructions for calculating a pressure request as a function of the flow limitation measure and making adjustments to pressure as described herein.

Another aspect of the present technology involves the generation of pressure or flow control information or signals that are derived proportionally as a function of a measure of flow limitation. For example, a controller or processor may be configured to control or determine a pressure setting or flow rate setting for a respiratory treatment device. Based on a measure of respiratory flow, an obstruction measure or a shape index representing a degree of obstruction or flow limitation may be determined or calculated by the apparatus. The apparatus may further optionally determine a ventilation measure representing a degree of change in ventilation from the measure of respiratory flow. The treatment pressure setting or flow rate setting may be derived by the apparatus as a proportional function of either or both of (1) the degree of obstruction or flow limitation and (2) the degree of change in ventilation.

Further embodiments of the technology will be apparent from the following disclosure.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Patients with OSA have recurrent apnoeas or hypopnoeas during sleep that are only terminated by the patient arousing. These recurrent events cause sleep fragmentation and stimulation of the sympathetic nervous system. This can have severe consequences for the patient including day-time sleepiness (with the attendant possibility of motor-vehicle accidents), poor mentation, memory problems, depression and hypertension. Patients with OSA are also likely to snore loudly, thus also disturbing their partner's sleep. The best form of treatment for patients with OSA is constant positive airway pressure (CPAP) applied by a blower (compressor) via a connecting hose and mask. The positive pressure prevents collapse of the patient's airway during inspiration, thus preventing recurrent apnoeas or hypopnoeas and their sequelae.

Ordinarily a patient will undergo two sleep studies where they are monitored using many sensors, the recording of which is known as a polysomnogram. The first study (without therapy) confirms the diagnosis of OSA, while the second is used to titrate the patient to the correct therapy pressure.

Pressure requirements vary throughout the night because of changes in position, posture and sleep state. The physician will recommend a pressure (the titration pressure) likely to cover any eventuality. An alternative to this is an automatic machine that adjusts the pressure to the patient's needs; this therapy is known as automatic positive airway pressure or APAP. An advantage of APAP therapy is that it is adaptable to pressure requirements that may change over many time scales. For example, pressure requirements change during the night with posture and sleep state, perhaps over the weekend with alcohol consumption, over months because of the beneficial effect of the therapy itself and over the course of years because of weight loss or gain. Also, because an APAP machine typically raises the pressure when it is needed, the patient can go to sleep with a comfortable pressure much lower than any therapeutic maximum. Finally, because APAP machines work at potentially lower pressures, the effects of mask leaks tend to be ameliorated somewhat.

Figure 1:
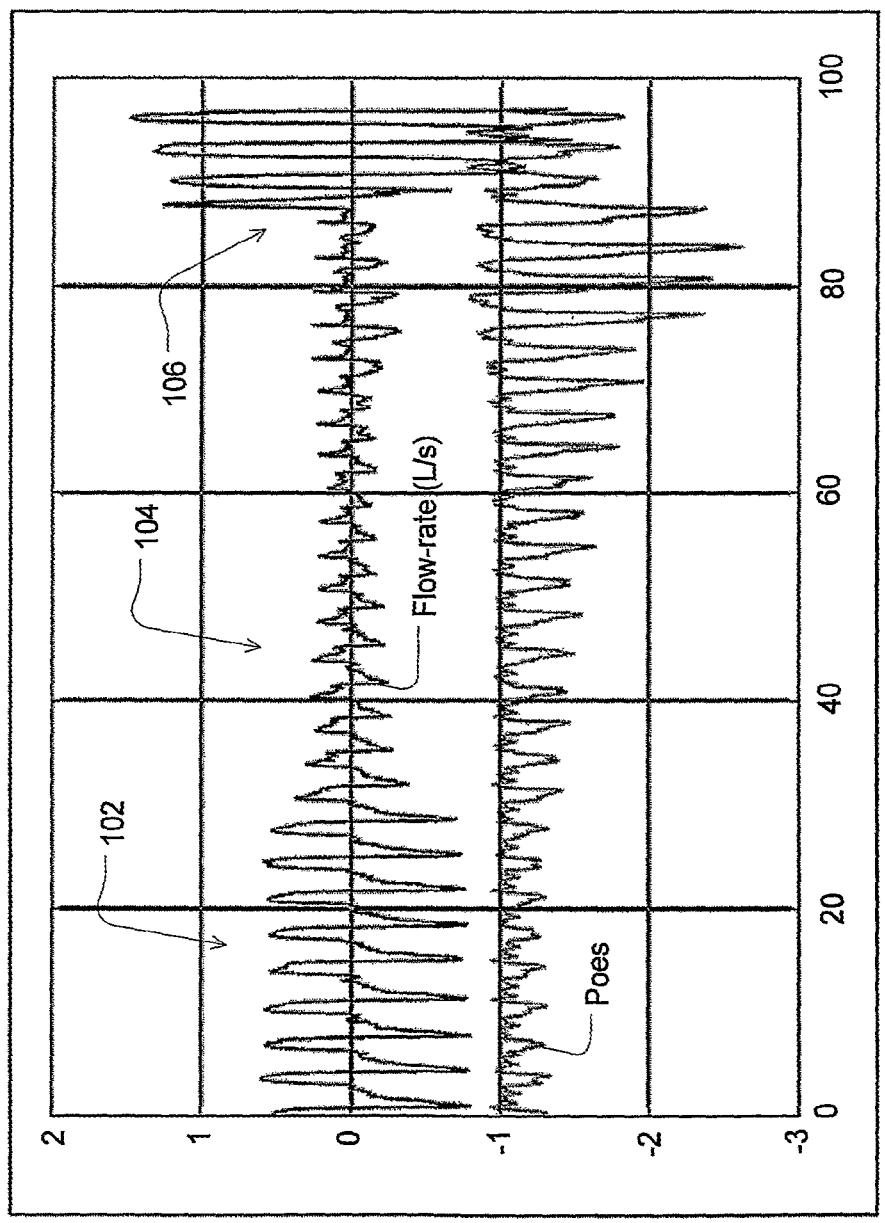
FIG. 1 shows air flow of a patient first breathing normally, then experiencing airway collapse and finally arousing.

A known algorithm that is used to automatically set patient pressure in APAP machines is called ResMed AutoSet. All in all, the AutoSet device, and its algorithm, is excellent for treating OSA patients. The ResMed AutoSet algorithm responds to three things: flow limitation, snore (audible noise) and apnoea. Setting automatic pressure is also described in U.S. Pat. No. 5,704,345, the contents of which are hereby expressly incorporated herein by cross-reference. Flow-limitation is a fluid dynamic property of so called "collapsible tubes" conveying a fluid flow. The pharynx in patients with OSA is an example of a collapsible tube (albeit a muscular one rather than a simple passive tube being studied on a bench top). In essence, flow-limitation is a condition in a collapsed tube conveying a flow where (given that the upstream pressure is held constant) the flow is no longer increased by decreasing the downstream pressure (i.e., an increase in the flow-driving differential pressure). In patients with a collapsed upper airway this equates to a situation where the patient is no longer receiving adequate ventilation and yet increases in breathing effort no longer increase the inspiratory flow-rate. FIG. 1 shows an example of such a patient first breathing normally at 102, then experiencing airway collapse at 104 and, despite more negative excursions in oesophageal pressure (a measure of breathing effort), not managing to increase tidal volume or flow-rate. Eventually the patient arouses at 106 in order to open the airway and takes a few big breaths to restore blood-gas homeostasis.

The ResMed AutoSet algorithm monitors patient flow and raises pressure when it detects flow limitation or snore. Because apnoeas are normally preceded by periods of flow limitation (also called partial obstruction) or snoring, apnoeas are rarely encountered. As a backup measure, pressure is also raised if an apnoea is detected. In the absence of any measured flow disturbance, the pressure is allowed to decay slowly and hopefully an equilibrium pressure will be achieved that allows the patient to sleep arousal-free. The AutoSet algorithm responds proportionally and so a metric is used for each condition to which it responds. The metrics used are: a flattening index for flow-limitation, a calibrated RMS measure of sound averaged over an inspiration for snore and the length of any apnoea detected.

A flattening index is a non-dimensional feature (e.g., a real number) calculated using a patient's inspiration waveform. It attempts to measure essentially how flat-topped the waveform is. A feature of flow limitation is that while the downstream pressure is sufficiently low to keep the tube collapsed the flow-rate will be more or less maintained at a constant value, regardless of changes to the driving pressure. In a patient with flow-limited breathing this equates to an inspiratory waveform with a flat top (i.e., a constant inspiratory flow-rate.)

For example, depending on the chosen scale of the index, normal breathing can produce a flattening index of around 0.2 while a severely flattened waveform can produce a flattening index of about 0.1 or less. For APAP therapy a limit is typically established (e.g., 0.19 in some machines) and the pressure is raised in proportion to how far the flattening index is below the threshold. In order to reduce the effects of noise and increase specificity, a typical pressure setting algorithm may also use a five breath point-wise moving average. A possible disadvantage of the five breath average is that it slows down the detection of flow-limitation because five abnormal breaths need to be averaged before flattening may fall to its final nadir. Three heuristic weightings can be applied to the threshold at which flattening will cause the pressure to rise, such that greater reductions in flattening are required: as the leak increases, as the therapy pressure rises and as evidence of valve-like breathing increases. These heuristics serve to prevent potential pressure runaway in the face of degraded information (flow signal).

Figure 2:
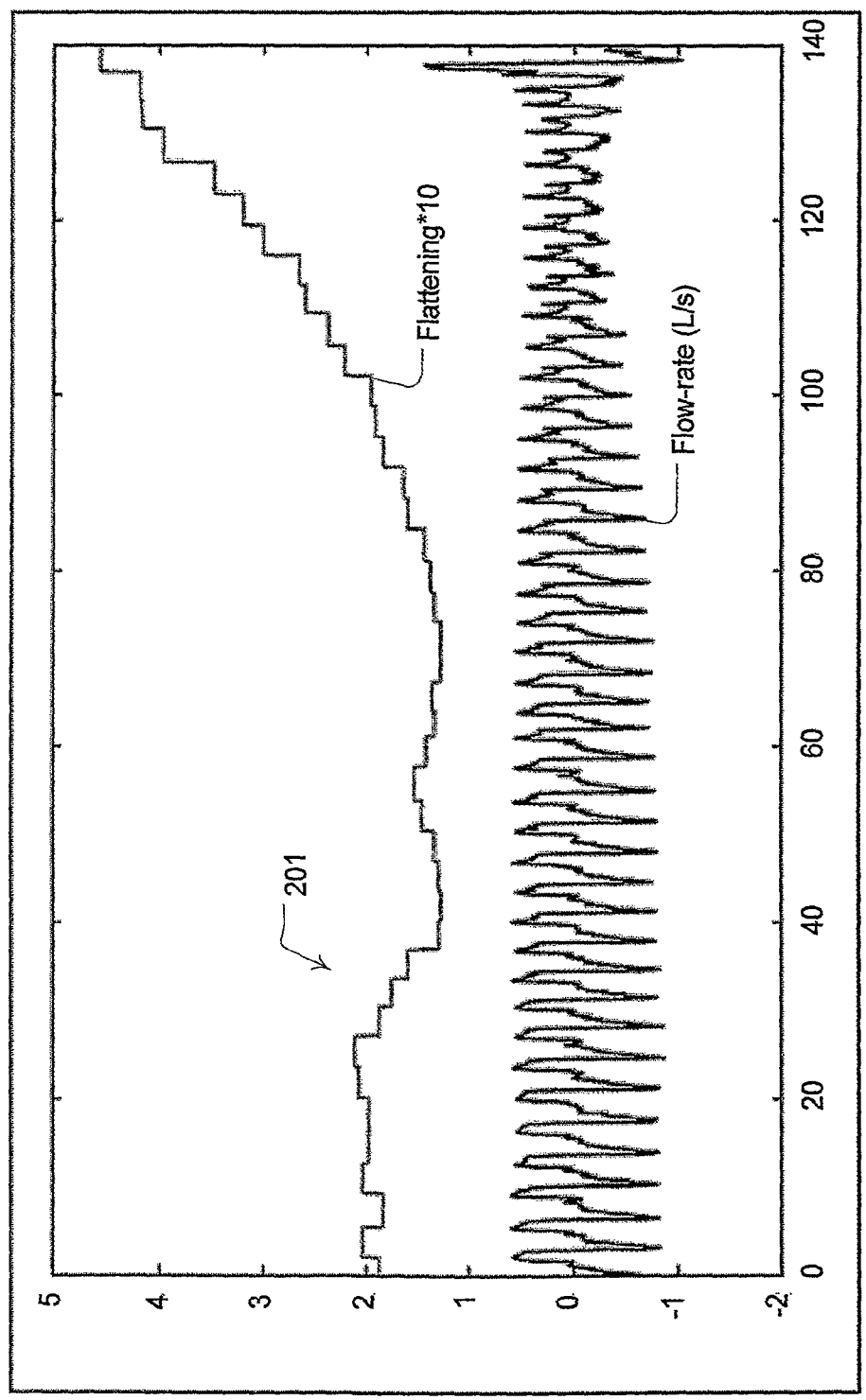
FIG. 2 shows a flattening index in reference to a patient experiencing obstruction indicated by an "M" shape breathing pattern.

While a flattening index is an excellent measure of flow-limitation, it is designed to detect certain situations. However, in some particular implementations it has been observed not to address some rare situations. The following lists areas where we have made such observations:

1. A five-breath moving average slows down the detection of flow-limitation. This is illustrated in FIG. 2. In FIG. 2, the top trace shows a plot of a traditional five-breath moving-average flattening index. The bottom trace shows a measure of respiratory flow. The patient begins to obstruct mildly and the flattening trace descends in staircase fashion at 202 due to the five-breath average. To the right of the graph the obstruction becomes more severe and progressively more "M" in shape. As shown, the flattening index eventually starts to reverse direction and increase rather than decrease with worsening obstruction.

Figure 3:
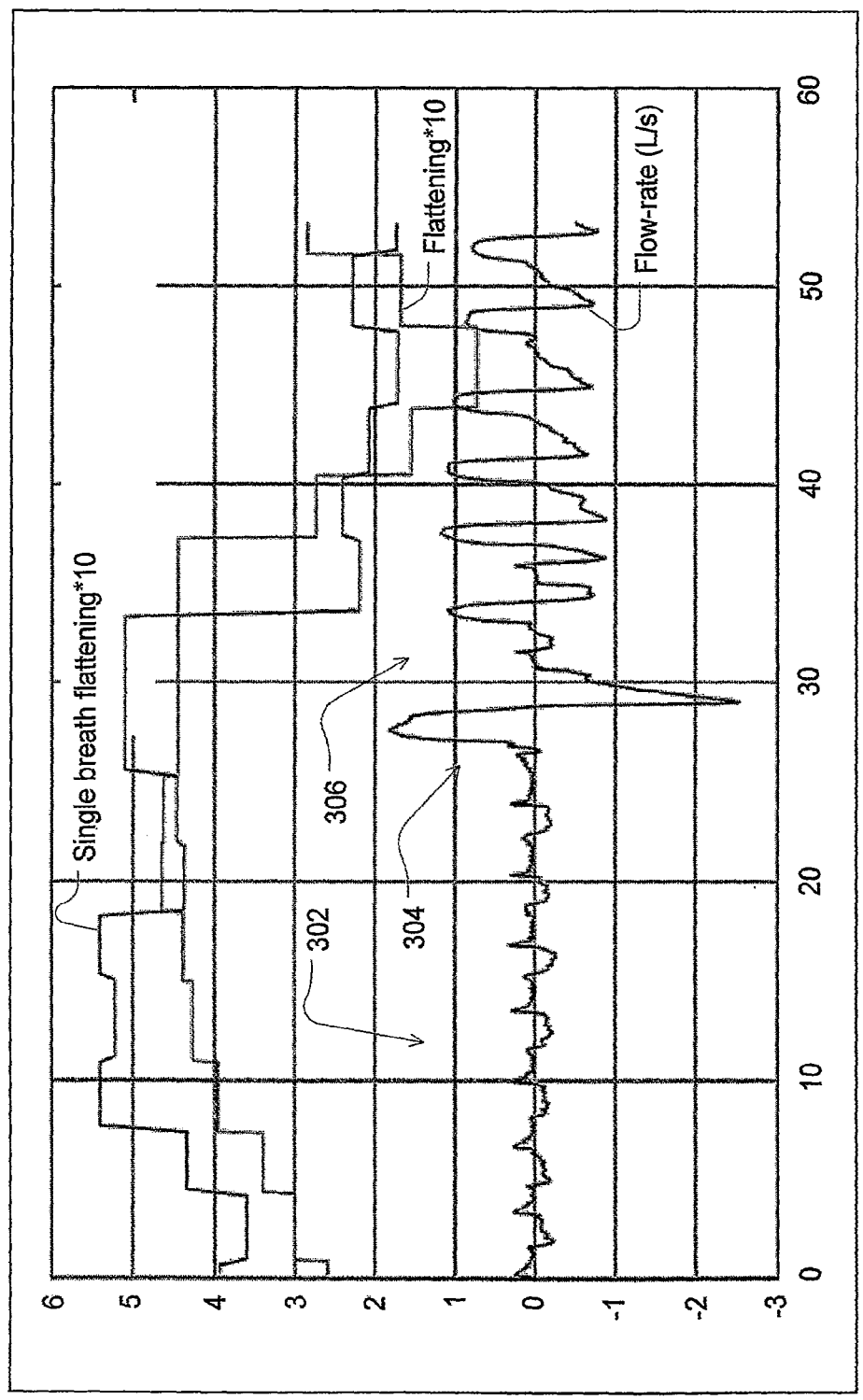
FIG. 3 shows flattening indices with and without multi-breath averaging in reference to a patient experiencing obstruction indicated by an "M" shape breathing pattern leading to a breathing pattern indicative of the patient's arousal from sleep.

2. Because different inspiratory shapes can average to give a completely new shape, the five breath moving average can have consequences. This is illustrated in FIG. 3. FIG. 3 shows a sequence of so called, M-shaped obstructed breaths at 302 ending in an arousal at 304 followed by some reasonably normal recovery breaths at 306. As shown in the graph, both single-breath flattening and traditional flattening are high at the end of the sequence of M-breaths (the former getting to the maximum value quicker) and that after the arousal, traditional flattening actually falls below 0.1, not because the breaths are flattened, rather because the M-breaths averaged with the normal breaths to produce a pseudo-flat shape.

3. The flattening index is not designed to detect M breaths. In fact, the flattening index goes high when M-shaped breaths occur. This is illustrated in FIGS. 2 and 3.

4. The flattening index can cause a pressure increase regardless of current ventilation or sleep state of the patient-user of the device.

5. The heuristics applied to de-weight flattening might also result in under-treatment in some patients.

6. The flattening index is subject to normal random variations that have consequences for the sensitivity and specificity of any algorithm that uses it to detect flow-limitation.

Although M-shaped breaths may be rare, it may still be desirable to develop further methods and devices for detecting flow-limitation and/or improve existing methods and devices.

Figure 4:
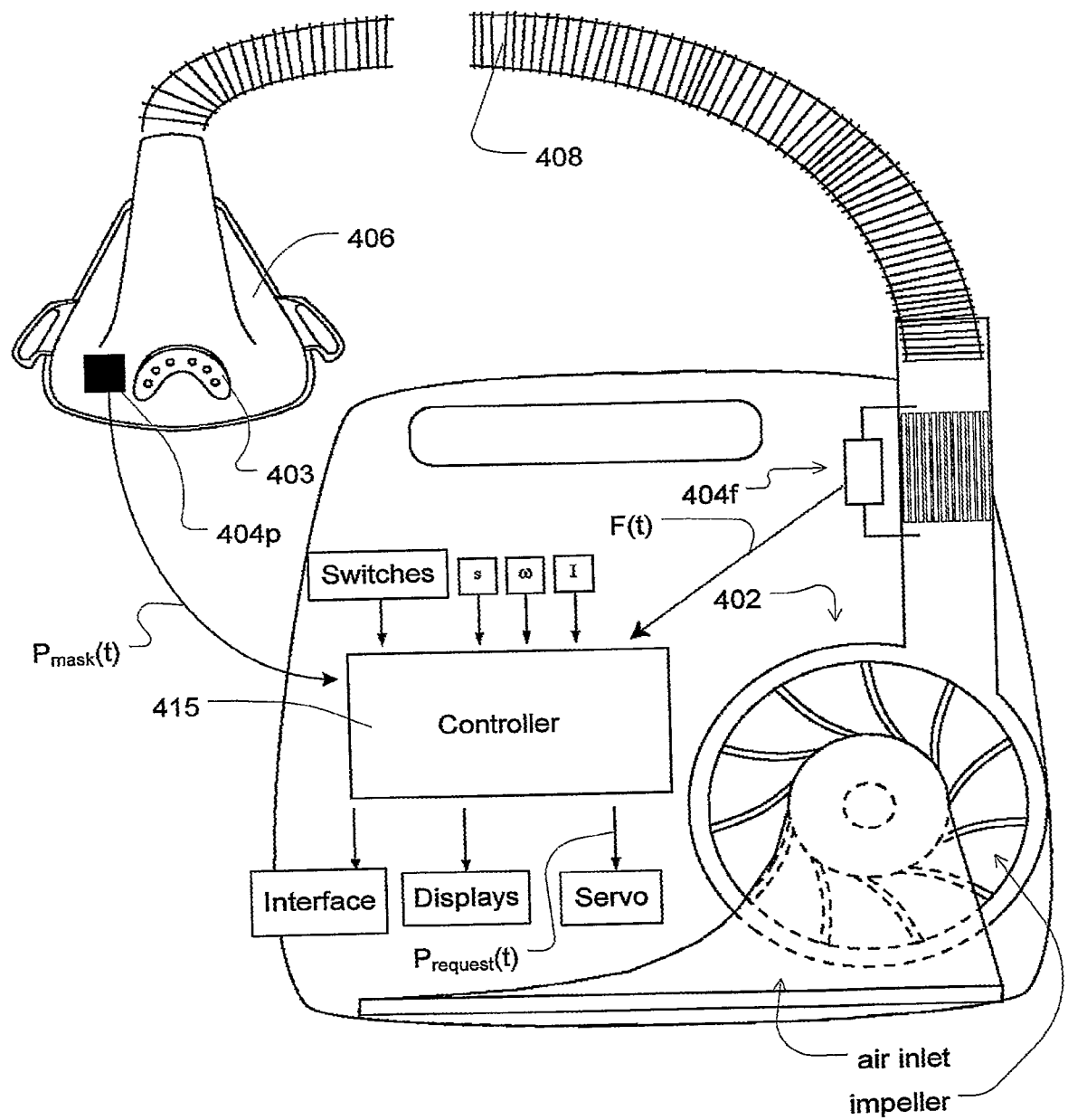
FIG. 4 shows example components of an apparatus for detection and/or treatment of flow limitation or partial obstruction.

In reference to FIG. 4, the present technology involves a pressure delivery and/or flow limitation detection device that may include a flow generator such as a servo-controlled blower 402. The device will typically also include a patient interface such as a mask 406 and an air delivery conduit 408 to carry a flow of air or breathable gas to and/or from a patient. The blower 402 may be coupled with the air delivery conduit 408 and the mask 406. Exhaust gas can be vented via exhaust 413. Optionally, a flow sensor 404*f* and/or pressure sensor 404*p* may also be utilized. For example, mask flow may be measured using a pneumotachograph and differential pressure transducer or similar device such as one employing a bundle of tubes or ducts to derive a flow signal F(t). Also mask pressure may be measured at a pressure tap using a pressure transducer to derive a pressure signal $P_{mask}(t)$. The pressure sensor 404*f* and flow sensor 404*p* have only been shown symbolically in FIG. 4 since it is understood that other configurations and other devices may be implemented to measure flow and pressure. The flow F(t) and pressure $P_{mask}(t)$ signals may be sent to a controller or microprocessor 415 via one or more analog-to-digital (A/D) converters/samplers (not shown) to derive a pressure request signal $P_{request}(t)$.

Alternatively, a flow signal f(t) and/or pressure signal $P_{mask}(t)$ may be estimated or calculated in relation to the blower motor by monitoring current (I) supplied to the motor, the speed (S) and/or revolutions (w) of the motor with or without the provision of flow and pressure sensors as described above. Optionally, the blower motor speed may be held generally constant and pressure changes in the mask may be implemented by controlling an opening of a servo-valve that may variably divert/vent or deliver airflow to the mask. Furthermore, other types of patient interface may be used in place of the mask and the flow and/or pressure sensors may measure flow and pressure in alternative locations with respect to the patient interface.

The controller or processor 415 is configured and adapted to implement the methodology or algorithms described in more detail herein and may include integrated chips, a memory and/or other control instruction, data or information storage medium. For example, programmed instructions with the control methodology may be coded on integrated chips in the memory of the device or such instructions may be loaded as software or firmware using an appropriate medium.

With such a controller, the apparatus can be used for many different pressure treatment therapies by adjusting the pressure delivery equation that is used to set the speed of the blower or to manipulate the venting with the release valve and may be based on detection methodologies involved in the pressure delivery equation as illustrated in the example embodiments detailed herein. Alternatively, they may be implemented in a device without the pressure treatment components such that the device may be used to diagnose, detect and/or quantify the existence of flow limitation.

The methodologies or algorithms presented herein for detecting and/or treating breathing patterns indicative of partial obstruction can be implemented with the controller as a fuzzy logic control system. Generally, fuzzy logic is a way for transforming ideas for system behavior into computer code that is based on real numbers for the parameters of a control system. However, the problem at hand is basically one of statistical pattern recognition and may be implemented using other techniques such as the alternatives discussed in more detail herein. Therefore, while the following technology is presented in terms of a fuzzy logic control system, it is understood that there are other ways of implementing the methodologies into a control system based on the desired control inputs and the exemplary output functions.

To this end, an embodiment of the control system of the present technology can be implemented according to the following general approach using a partial obstruction or flow limitation measure such as a Fuzzy Flow-Limitation (FFL) measure. Using such a measure is an approach that may remedy some of the observations previously described with respect to the use of traditional flattening indices as a system control variable. The flow limitation measure FFL uses multiple feature pattern recognition to improve the sensitivity and specificity of the algorithm's response to flow-limitation (or more properly: partial upper-airway obstruction). In an embodiment, the general approach with the flow limitation measure FFL may include some or all of the following steps:

1. Monitor the patient's respiratory flow.
2. Extract inspiratory and expiratory waveforms from the flow signal.
3. Calculate features from each component of the waveform or, where appropriate, from the combined waveform. Multiple features may be considered to constitute a pattern.
4. Calculate fuzzy input variables from the raw variables. This step constitutes a mapping of an input variable to a new space. Data mining of a suitable cohort of patients allows good estimation of the parameter space.
5. Combine the derived fuzzy variables using fuzzy logic to produce fuzzy outputs. This step can be formulated using a matrix that allows intuitive understanding by the layperson.
6. De-fuzzify the fuzzy outputs to produce a crisp value (real number) to be used by the pressure control algorithm.
7. Combine fuzzy outputs from multiple sources.
8. Adjust treatment pressure based on the FFL result.

In accordance with this methodology, an example system maps input parameters that vary widely in range to variables that can be readily interpreted with fuzzy logic principles. For example, a shape index such as a flattening index may be mapped to the fuzzy variables such as HIGH_FLATTENING, NORMAL_FLATTENING and LOW_FLATTENING, etc. Each of these variables would take a value between zero and one, depending on the value of the flattening index as determined by mathematical functions associated with the variables and based on the input data associated with a flattening determination such as respiratory airflow. Similarly, other fuzzy variables can map a ventilation measure such as HIGH_VENTILATION, NORMAL_VENTILATION and LOW_VENTILATION, etc., based on appropriate mathematical functions and input data associated with determining ventilation. Still other fuzzy variables can also map a respiratory duty cycle measure (e.g., a ratio of time of inspiration ($T_i$) to the total time of a breathing cycle ($T_{tot}$)) such as $T_i$-on-$T_{tot}$_LOW, $T_i$-on-$T_{tot}$_NORMAL, or $T_i$-on-$T_{tot}$_HIGH, etc. These variables may be further mapped to fuzzy outputs that in turn may be used to generate control variables. Fuzzy outputs associated with a flow limitation measure may be, for example, MILD, MODERATE and SEVERE and may be based on other fuzzy variables such as the previously mentioned examples. For example, the fuzzy logic controller may implement the conditions represented by example statements such as:

(a) IF (LOW_FLATTENING & LOW_VENTILATION) then flow-limitation is SEVERE.
(b) IF (HIGH_FLATTENING & $T_i$-on-$T_{tot}$_HIGH) then flow-limitation is MILD.

The de-fuzzified output, which can be used as a flow limitation measure, can be implemented to range between zero (no flow-limitation) and one (severe). With such a system, the input space can be classified in a non-linear sense using readily interpretable rules without any loss of real-number precision.

Indeed, with the precision of such a flow limitation measure, which represents a degree of obstruction over a continuous range from 0 to 1, the measure can be implemented proportionally to derive a response pressure or flow control setting well suited to treat the condition detected with the measure. For example, without needing to utilize a threshold that would otherwise be compared to such a measure to determine whether or not a pressure adjustment should be made, the measure may be more directly implemented in the setting of a respiratory treatment apparatus or determining of a treatment setting for such a device. For example, the obstruction measure may serve as a proportional function that may be directly applied to a pressure adjustment quantity or flow rate adjustment quantity (e.g., measure*adjustment quantity). The resultant adjustment quantity could then be applied to a treatment setting of a respiratory treatment apparatus. As discussed with respect to the technology described in more detail herein, an "FFL" measure may be implemented to serve as such a proportional treatment setting function.

Figure 5:
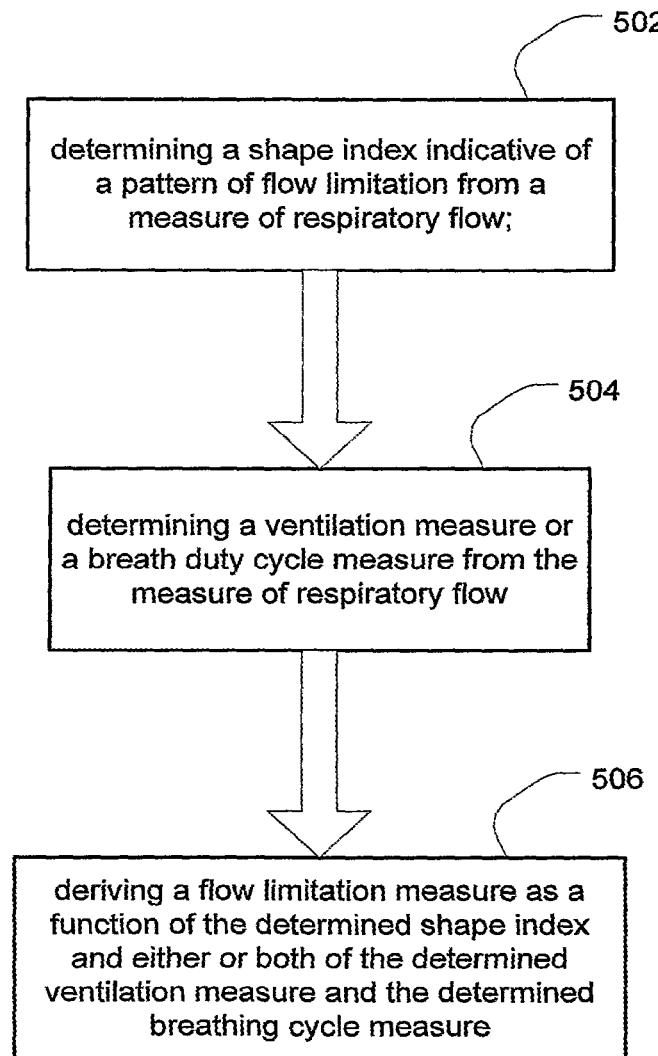
FIG. 5 illustrates suitable steps for a detection or treatment device in detecting flow limitation or partial obstruction.

As further illustrated in FIG. 5, in such a system flow limitation may be detected and/or quantized by a method that includes (a) determining a shape index indicative of a pattern of flow limitation from the measure of respiratory flow shown in step 502; (b) determining a ventilation measure or a breath duty cycle measure from the measure of respiratory flow shown in step 504; and (c) deriving a flow limitation measure as a function of the determined shape index and either or both of the determined ventilation measure or the determined breathing cycle measure shown in step 506. With such a method, sophisticated adjustments to the treatment pressure may be made. For example, increases to treat flow limitation may be based on a condition such that a pressure change can occur if it is determined that both (a) a shape index is indicative of the presence of an M shape breath or flattened breath in the respiratory airflow and (b) the ventilation measure is decreasing sufficiently to be indicative of less than normal ventilation. Additional increases to treat flow limitation may be based on another condition such that a pressure change can occur if it is determined that both (a) the shape index is indicative of the presence of an M shape breath in the respiratory airflow and (b) an increase of the duty cycle measure is detected. With such conditions, a suitable treatment response may be provided without an unnecessary treatment change that could otherwise occur when the shape index, ventilation measure or breathing duty cycle measure taken alone do not accurately predict a level of flow limitation.

Accordingly, in one embodiment, the system may be characterized by the use of a plurality of input features (e.g., 4) for deriving the flow limitation measure FFL. The input features may include (1) a single-breath flattening (SBF) shape index, (2) an M shape index (MS), (3) a ventilation measure such as a ventilation-ratio (VR) and/or (4) a respiratory duty cycle measure such as the ratio of inspiratory time to the total breath time ($T_i$-on-$T_{tot}$).

An embodiment of a shape index implemented as a single breath flattening index SBF may be calculated similar to the approach disclosed in U.S. Pat. No. 5,704,345 except that it is preferably performed without using a five-breath moving-average. The details of an implementation of a single breath flattening shape index determination are disclosed in section A herein.

An exemplary implementation of a determination of an M-shape shape index is described in section B herein. The illustrated calculation of the M-shape feature can vary in the range from zero (i.e., the inspiratory flow waveform is not M-shaped) to one (i.e., the inspiratory flow waveform is definitively M-shaped). The M-shape index may optionally be augmented by another shape index such as a simple "chair-shape" index. An exemplary determination of the chair-shape index (e.g., Fuzzy "Chairness") is also detailed in section B.

An embodiment of a determination of a suitable ventilation measure may be based on a tidal volume calculation. For example, the ventilation measure may be a ratio including a current tidal volume and a prior tidal volume such that the measure can be indicative of changes in ventilation or tidal volume. In one suitable embodiment, the measure may be a ventilation ratio VR that can be calculated as follows:

1. Take the absolute value of the respiratory flow and filter it with a simple low-pass filter (time-constant=three minutes).
2. Divide the filter output by two to give "3 minute ventilation."
3. Calculate the respiratory tidal volume (essentially the mean of the inspired and expired volumes).
4. Divide the tidal volume by the length of the breath—giving mean breath flow-rate—and then divide this value by the 3 minute ventilation giving a measure of how this breath compares to recent ventilation.

Ordinarily, the VR will oscillate over a small range of about one. In the event of severe upper-airway obstruction, it will descend to values much less than one and can descend to zero for total obstruction. Big breaths (recovery breaths on arousal) will have a VR much greater than one (e.g., 1.5-2). Further details for a calculation of the particular ventilation ratio VR are included in Section G herein.

As previously mentioned, the system can optionally utilize a respiratory duty cycle measure in the derivation of flow limit measure FFL. The measure may be based on a ratio of a current and prior duty cycle so that it can be indicative of changes in the respiratory duty cycle. Exemplary details for the calculation of a respiratory duty cycle ratio TTR are further described in Section G herein. For example, a suitable breath duty cycle measure can be based on the calculation of a $T_i$-on-$T_{tot}$ variable. The chosen variable has the (implausible) limits of zero (no inspiration) and one (no expiration). Because the base $T_i$-on-$T_{tot}$ can vary from patient to patient, a ratio of $T_i$-on-$T_{tot}$ to its recent mean value is calculated which has been designated herein a $T_i$-on-$T_{tot}$ ratio. The recent mean value of $T_i$-on-$T_{tot}$ can be calculated by feeding each $T_i$-on-$T_{tot}$ value calculated into a simple low-pass filter. When $T_i$-on-$T_{tot}$ is increasing relative to recent history, the TTR will exceed one. $T_i$-on-$T_{tot}$ has values around 0.4 while TTR will be one ordinarily and greater than one when patients are trying to "compensate", i.e., increase their tidal volume in the face of an obstructed upper airway.

Figure 6:
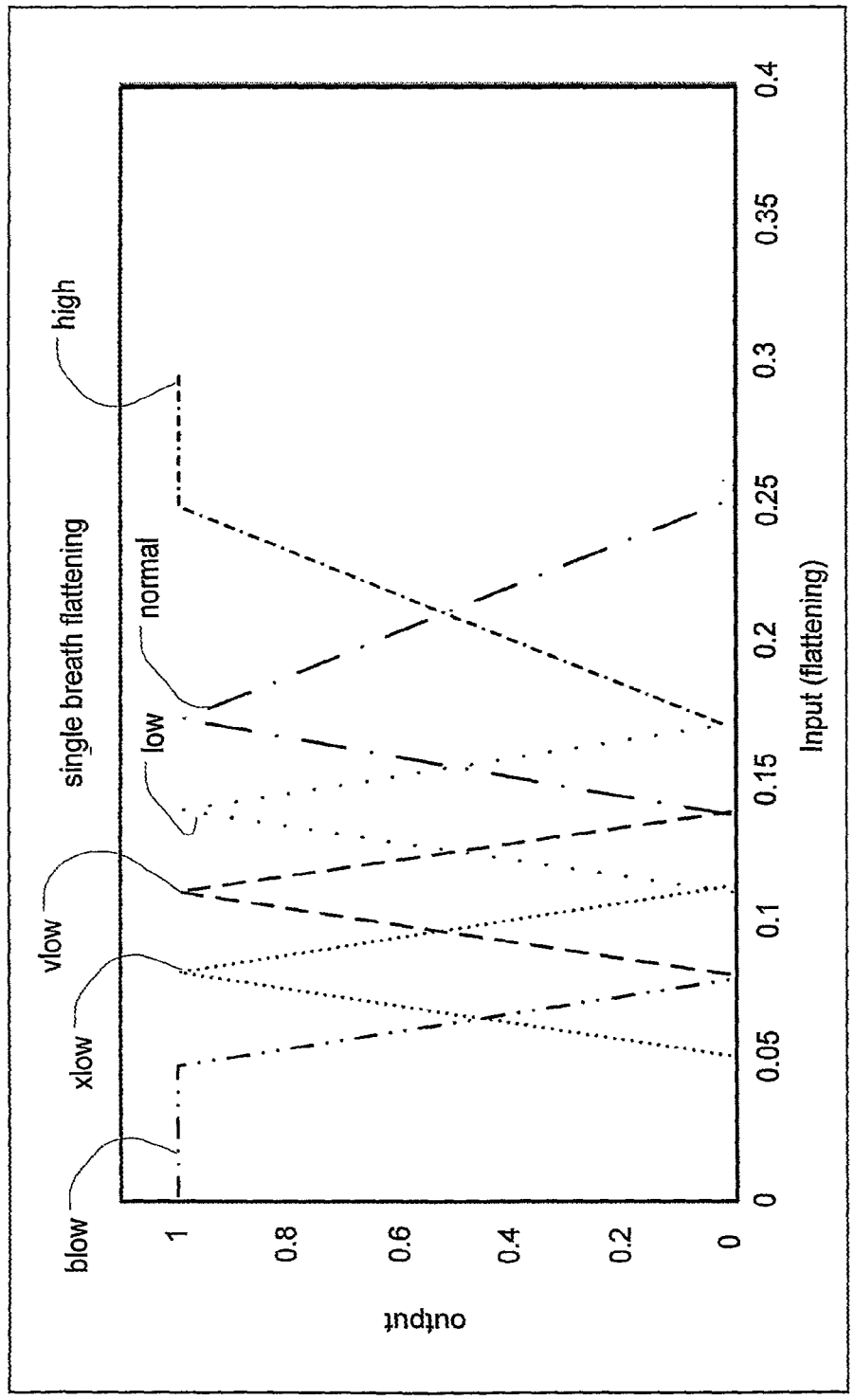
FIG. 6 shows example fuzzy membership functions for variables based on a single breath flattening shape index.

As previously mentioned, these input features are mapped by mathematical functions into several variables. Thus, the shape index SBF can be mapped into, for example, six fuzzy variables: B_LOW_FLATTENING, EXTRA_LOW_FLATTENING, VERY_LOW_FLATTENING, LOW_FLATTENING, NORMAL_FLATTENING and HIGH_FLATTENING. These fuzzy memberships are shown by the sample functions that have been graphed in FIG. 6 and have been presented in the order from left to right in conjunction with each variable listed respectively above. As an example application of the membership functions, if shape index SBF is computed and results in a value of 0.05, when applied to each of the membership functions, the variable B_LOW_FLATTENING would result in a value of 1.0 and a value of zero for all of the other fuzzy variables in the graph of FIG. 6. Other suitable functions and variables may be selected as desired.

Figure 7:
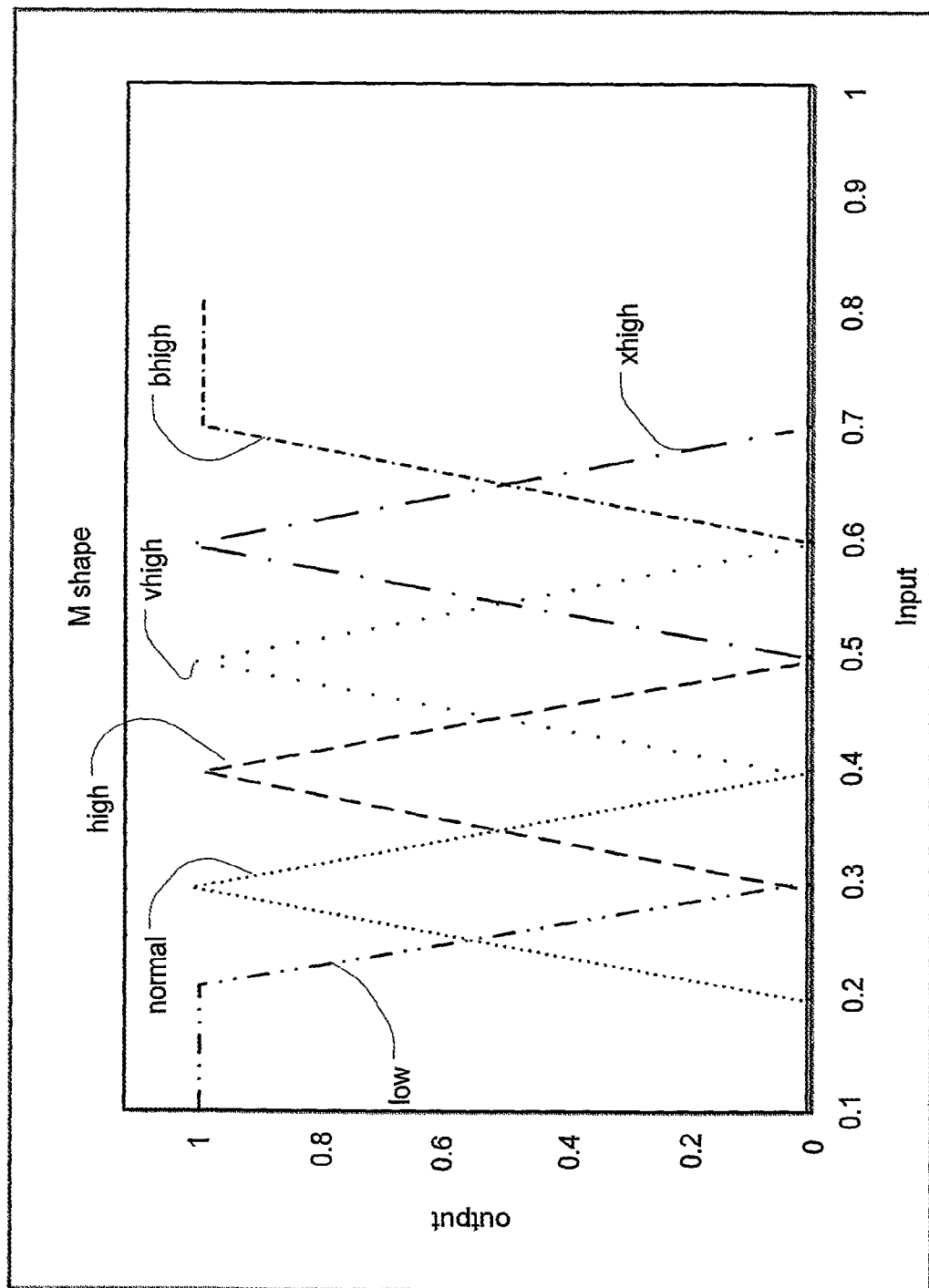
FIG. 7 shows example fuzzy membership functions for variables based on an m-shape breath shape index.
Figure 8:
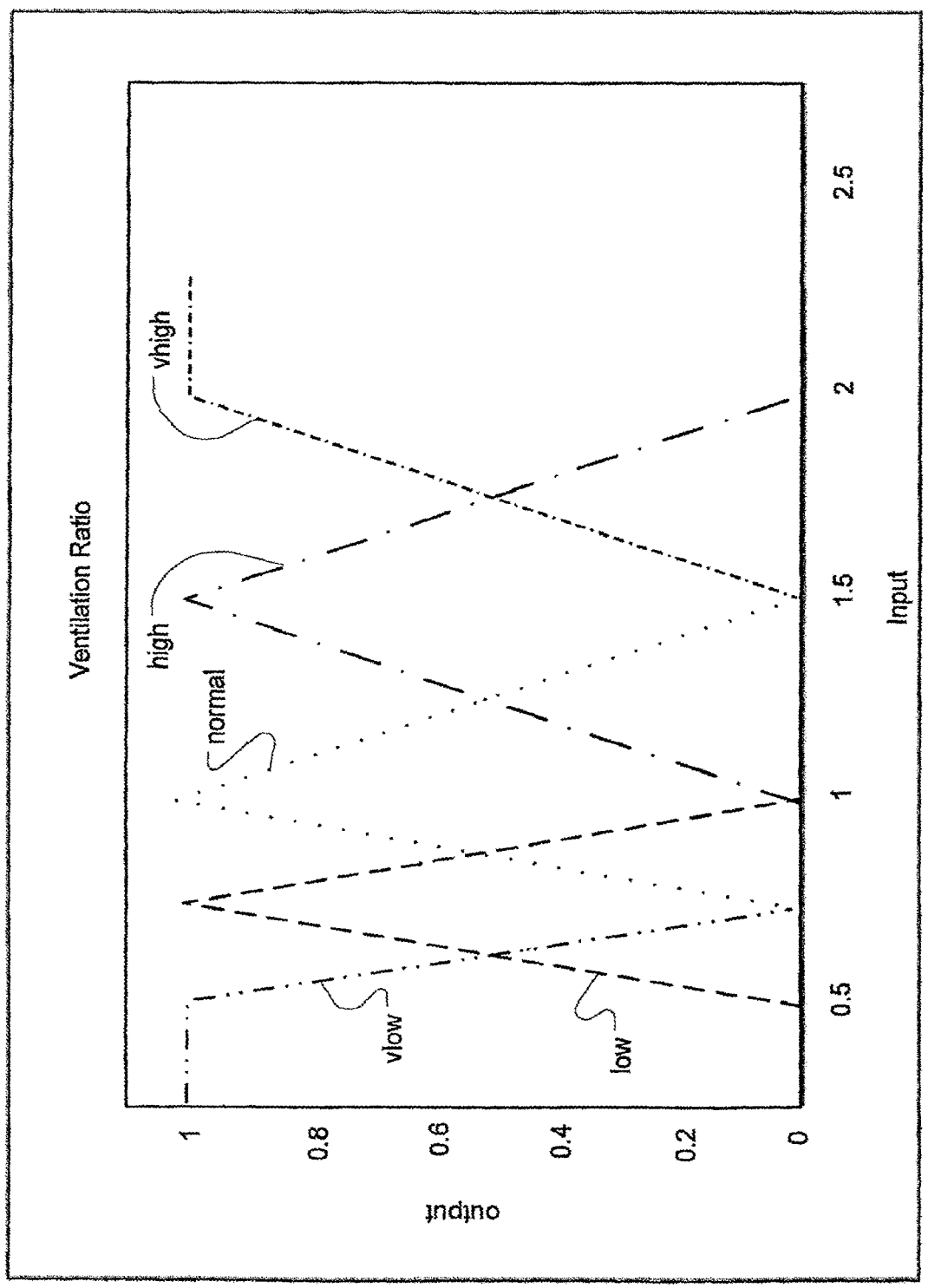
FIG. 8 shows example fuzzy membership functions for variables based on a ventilation ratio index.
Figure 9:
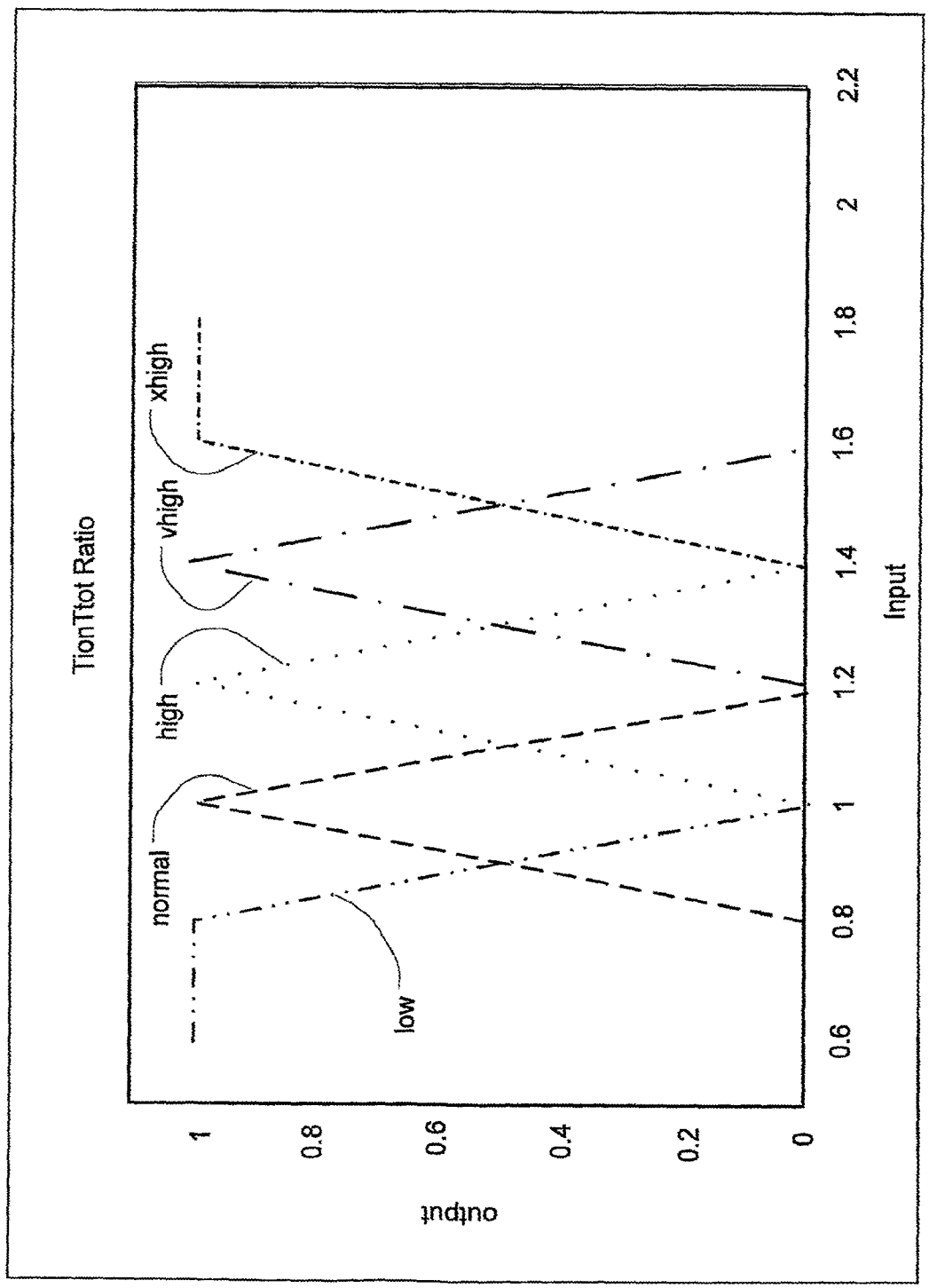
FIG. 9 shows example fuzzy membership functions for variables based on a breath duty cycle ratio.

Similarly, example membership functions and variables based on the computation of the M-shape shape index are shown in FIG. 7. This graph presents suitable functions for LOW_M-SHAPE, NORMAL_M-SHAPE, HIGH_M-SHAPE, VERY_HIGH_M-SHAPE and B_HIGH_M-SHAPE. Example membership functions and variables based on the computation of the ventilation ratio index are shown in FIG. 8. This graph presents suitable functions for VERY_LOW_VENTILATION, LOW_VENTILATION, NORMAL_VENTILATION, HIGH_VENTILATION and VERY_HIGH_VENTILATION. Finally, example membership functions and variables based on the computation of the breath duty cycle ratio are shown in FIG. 9. This graph presents suitable functions for $T_i$-on-$T_{tot}$_LOW, $T_i$-on-$T_{tot}$_NORMAL, $T_i$-on-$T_{tot}$_HIGH and $T_i$-on-$T_{tot}$_VERY_HIGH and $T_i$-on-$T_{tot}$_EXTRA_HIGH.

Based on some or all of these mapped variables, a system may then apply or evaluate rules based on combinations of the variables in the derivation of the flow limitation measure FFL. For example, fuzzy rules have been illustrated in the tables below based on the prior identified fuzzy variables. These matrices also express an idea of what may constitute partial obstruction in natural language.

TABLE A

Flattening and Ventilation Measure

| | | Flattening measure (low = good, high = bad) | | | | | |
|---|---|---|---|---|---|---|---|
| | | Low | Normal | High | Very High | Extra High | B High |
| Ventilation | Very High | Zero | Negative | Zero | Zero | Zero | Zero |
| Ratio | High | Zero | Negative | Zero | Zero | Zero | Zero |
| Measure | Normal | Zero | Zero | Zero | Zero | Mild | M to M |
| (high = | Low | Zero | Zero | Mild | M to M | Moderate | M to S |
| good) | Very Low | Zero | Zero | M to M | Moderate | M to S | Severe |

Table A summarizes a set of fuzzy rules that may be applied with the fuzzy variables associated with the single breath flattening shape index and the ventilation ratio measure. For example, the rule in bold ("M to M", i.e., Mild to Moderate) in the "Very High" column with respect to flattening shape index's fuzzy variables and the "low" row with respect to the ventilation ratio measure's fuzzy variable represents the fuzzy rule:

if (VERY_HIGH_FLATTENING AND LOW_VENTILATION) then FFL is "Mild-to-Moderate".

This and the other rules represented in the table can be evaluated, where the "AND" is a fuzzy-and. Common output results for each output response (e.g., "Mild-to-Moderate") may then be fuzzy-or-ed together. For example, the two rules with "moderate" outputs (e.g., a measure of a moderate flow limitation) would be fuzzy-or-ed to give the final "moderate" output. This is the equivalent of the following equation:

moderate=(VERY_HIGH_FLATTENING AND
  VERY_LOW_VENTILATION) OR (EXTRA_
  HIGH_FLATTENING AND LOW_VENTILA-
  TION)

Based on the application of these rules in the derivation of the flow limitation measure at least three things are evident in its implementation: 1) as flattening severity increases (e.g., the shape index decreases) the FFL measure increases, 2) where flattening is occurring and ventilation is decreasing, the FFL measure is even more severe, and 3) where ventilation is high (e.g., recovery (big) breaths etc. are occurring) the response to flattening shape index is tempered.

There are cases where flow-limitation (at least initially) does not involve a reduction in tidal volume (e.g., the ventilation ratio). In these cases a patient maintains his or her tidal volume by increasing the duty cycle, i.e. by stretching the inspiration time as a percentage of the overall inspiration-expiration time. This trend can be measured or determined using a duty cycle measure (e.g., TTR) which in this embodiment will increase above one as the inspiration time lengthens.

The system may further combine flattening shape index information with a breath duty cycle measure (e.g., TTR) in a similar manner as it had been combined with a ventilation measure (e.g., VR) using the rules represented by the following table B.

TABLE B

Flattening and Breath Duty Cycle Measure

| | | Flattening measure (low = good, high = bad) | | | | | |
|---|---|---|---|---|---|---|---|
| | | Low | Normal | High | Very High | Extra High | B High |
| Ti-on-Ttot | Low | Zero | Negative | Zero | Zero | Zero | Zero |
| Ratio | Normal | Zero | Negative | Zero | Zero | Zero | Zero |
| Measure | High | Zero | Zero | Mild | M to M | Moderate | M to S |
| (high = | Very High | Zero | Zero | M to M | Moderate | M to S | Severe |
| bad) | Extra High | Zero | Zero | Moderate | M to S | Severe | Severe |

Like table A, table B represents fuzzy rules as well as a corresponding natural language description of flow obstruction based on the measure of breath duty cycle and the flattening shape index. For example, the rule in bold ("M to S", i.e., Moderate to Severe) in the "Extra High" column and the "Very High" row is the fuzzy rule:

if (EXTRA_HIGH_FLATTENING AND $T_i$-on-$T_{tot\_}$VERY_HIGH) then FFL is Moderate-to-Severe.

This rule represents a consideration that if the wave shape of the inspiratory breathing pattern is tending to severely-flat and the inspiration is moderately stretched by consideration of the duty cycle measure then the flow limitation measure FFL is Moderate-to-Severe. As mentioned with respect to table A, the result of the rules for common output functions of this table can be combined using the fuzzy-or operation.

In a manner similar to the way that the flow limitation measure is derived using the flattening shape index information and either or both of a ventilation measure and a breath duty cycle measure, the flow limitation may also be derived by using both M-shaping and/or Augmented M-shaping detection indices and either or both of the ventilation or breath duty cycle measures. Aspects of this derivation are illustrated in tables C and D.

TABLE C

M-Shaping or Augmented M-Shaping and Ventilation Measure

|  |  | M-shaping or Aug. M-shaping (low = good, high = bad) | | | | | |
|---|---|---|---|---|---|---|---|
|  |  | Low | Normal | High | Very High | Extra High | B High |
| Ventilation | Very High | Zero | Negative | Zero | Zero | Zero | Zero |
| Ratio | High | Zero | Negative | Zero | Zero | Zero | Zero |
| Measure | Normal | Zero | Zero | Zero | Zero | Mild | M to M |
| (high = | Low | Zero | Zero | Mild | M to M | Moderate | M to S |
| good) | Very Low | Zero | Zero | M to M | Moderate | M to S | Severe |

Table C represents rules like the rules of the prior charts except that they relate to the fuzzy variables based on the M-shaping shape index and/or the chair-shape index. As evident from the nature of the selection of output functions in the table, the rules in part are intended to prevent a response to a detected M-shape breathing pattern where the patient has a normal or above average ventilation. Thus, the flow limitation measure is derived so that the system will not respond to certain types of arousal breaths and "behavioral" M-shape breathing patterns such as those that can occur during REM sleep but are not indicative of a current flow limitation. For example, the rule represented by the entry in the top row of the last column of table C indicates that the output function is "zero" for a bad "B High" M-shape index related measure when there is a good ventilation measure (e.g., "Very High").

Furthermore, most M-shaped breaths represent moderate-to-severe obstruction and will exhibit a ventilation decrease. Thus, other rules of table C permit a detection of flow limitation for a pressure change of the system to address this situation of a detected M-shape breath and a low ventilation measure such as a decrease in ventilation.

As mentioned with respect to table A, the result of the rules for common output functions of this table can be combined using the fuzzy-or operation.

Table D presents rules involving the breath duty cycle measure.

As mentioned with respect to table A, the result of the rules for common output functions of this table can be combined using the fuzzy-or operation.

Figure 10:
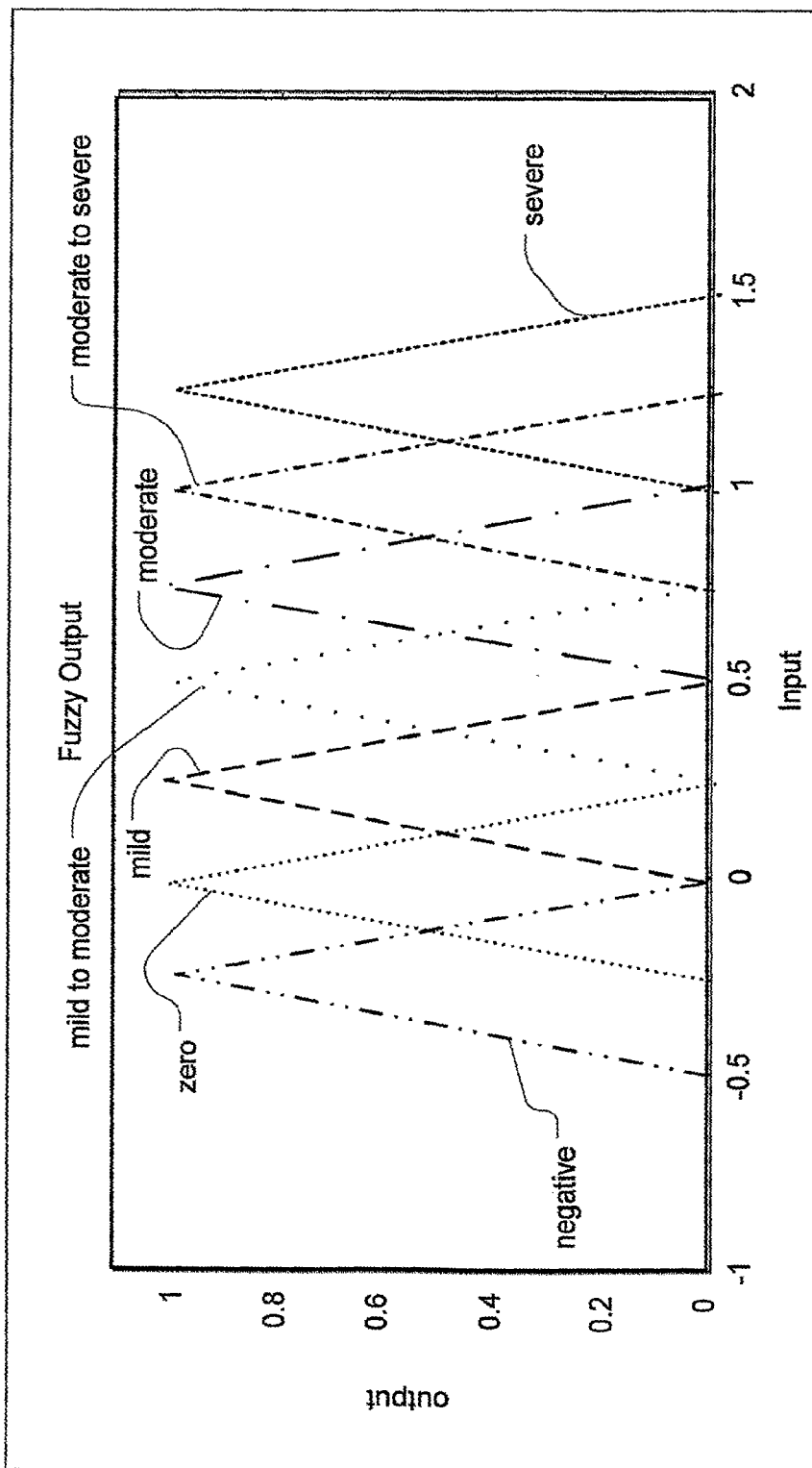
FIG. 10 shows example output membership functions for a flow limitation measurement.

Results of the rules applied based on tables A, B, C and D may thereafter be applied to output functions. FIG. 10 shows suitable fuzzy output membership functions that may be applied with the results. The output membership functions include NEGATIVE, ZERO, MILD, MILD_TO_MODERATE, MODERATE, MODERATE_TO_SEVERE and SEVERE.

As an example, consider table D. Once the individual fuzzy rules in the table have been calculated (e.g., if (EXTRA_HIGH_MSHAPE AND $T_i$-on-$T_{tot}$_VERY_HIGH) then FFL is Moderate-to-Severe), the outputs are collected and fuzzy-Or-ed together. For example, there are three Moderate-to-Severe outputs in table D that would need to be fuzzy-Or-ed. Once this is done for all the outputs, they are supplied to the defuzzification functions in FIG. 10 and the centroid method may be used to provide a crisp output as per FIG. 11. This results in a real number between 0 and 1.25. Once the individual outputs from all the tables are available, the maximum output may be used for the value of FFL.

In determining a single "crisp" measure in a de-fuzzification step as just mentioned, a centroid method or other such de-fuzzification operation may be performed. In the centroid method, the crisp value of the output variable is determined by finding a value associated with the center of

TABLE D

M-Shaping or Augmented M-Shaping and Duty Cycle Measure

|  |  | M-shaping or Aug. M-shaping (low = good, high = bad) | | | | | |
|---|---|---|---|---|---|---|---|
|  |  | Low | Normal | High | Very High | Extra High | B High |
| Ti-on-Ttot | Low | Zero | Negative | Zero | Zero | Zero | Zero |
| Ratio | Normal | Zero | Negative | Zero | Zero | Zero | Zero |
| Measure | High | Zero | Zero | Mild | M to M | Moderate | M to S |
| (high = | Very High | Zero | Zero | M to M | Moderate | M to S | Severe |
| bad) | Extra High | Zero | Zero | Moderate | M to S | Severe | Severe |

Figure 11:
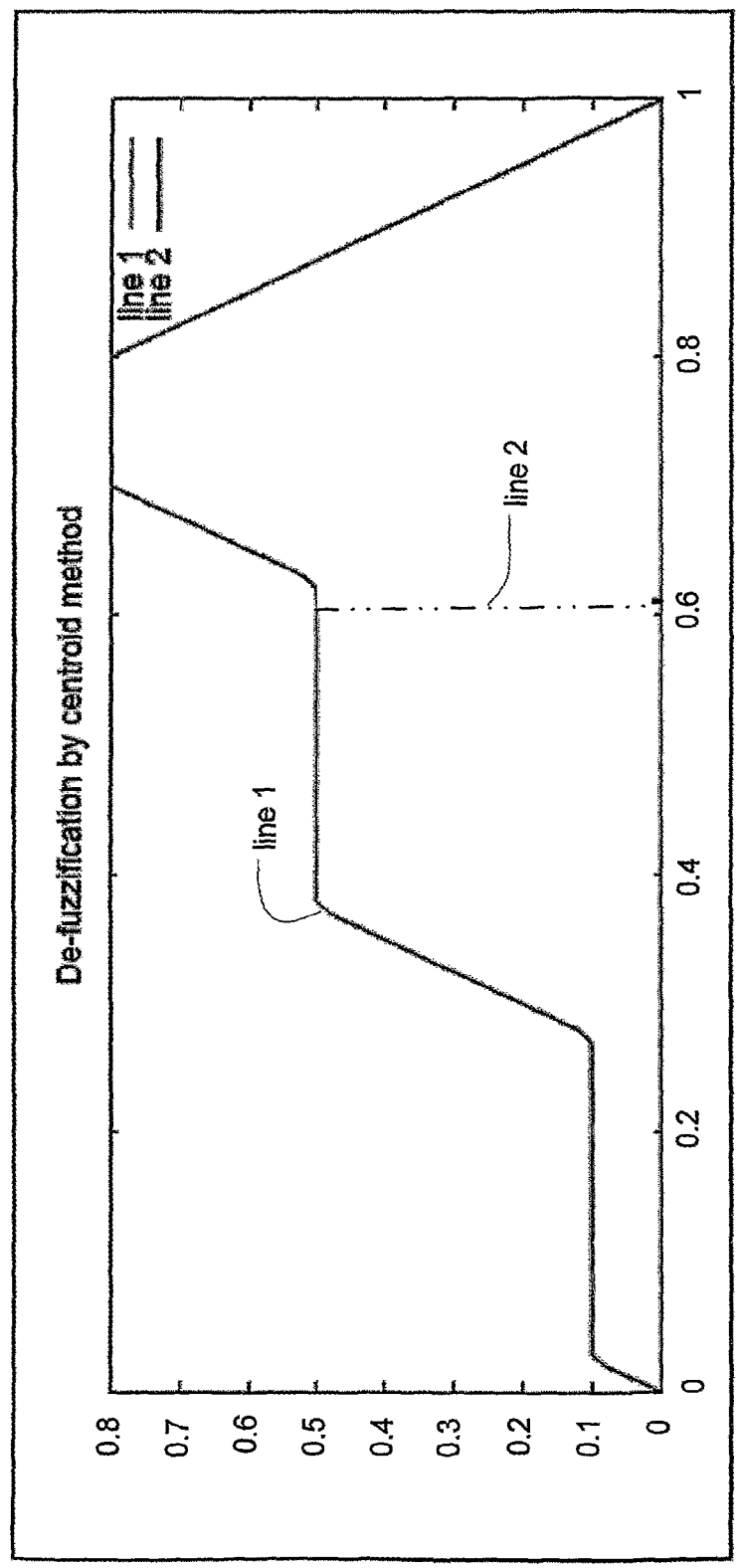
FIG. 11 shows and example de-fuzzification operation in the determination of a flow limitation or partial obstruction measure using a centroid method.

Table D represents particular fuzzy rules as well as a corresponding natural language description of flow obstruction or measures of flow limitation derived from the measure of breath duty cycle and the M-shaping and/or the augmented M-shaping determinations. In this example, the matrix "combines" the M-shape information with the $T_i$-on-$T_{tot}$ Ratio (rather than ventilation ratio). The matrix may be considered to relate to breaths that exhibit M-ness, or a degree of the existence of an M-shape pattern, in the presence of a trend of increasing breath duty cycle. This combination identifies flow limitation in breaths where the patient's ventilation is about "normal" and the patient is "compensating" by taking longer inspirations.

gravity of the values for the output functions. An example of such a method is illustrated in FIG. 11. FIG. 11 illustrates an application of the centroid method calculated for fuzzy inputs where MILD=0.1, MILD_TO_MODERATE=0.5, MODERATE=0.8. The calculated result is 0.61064. Those skilled in the art will understand other ways to calculate the crisp measure in view of the present description.

Figure 12:
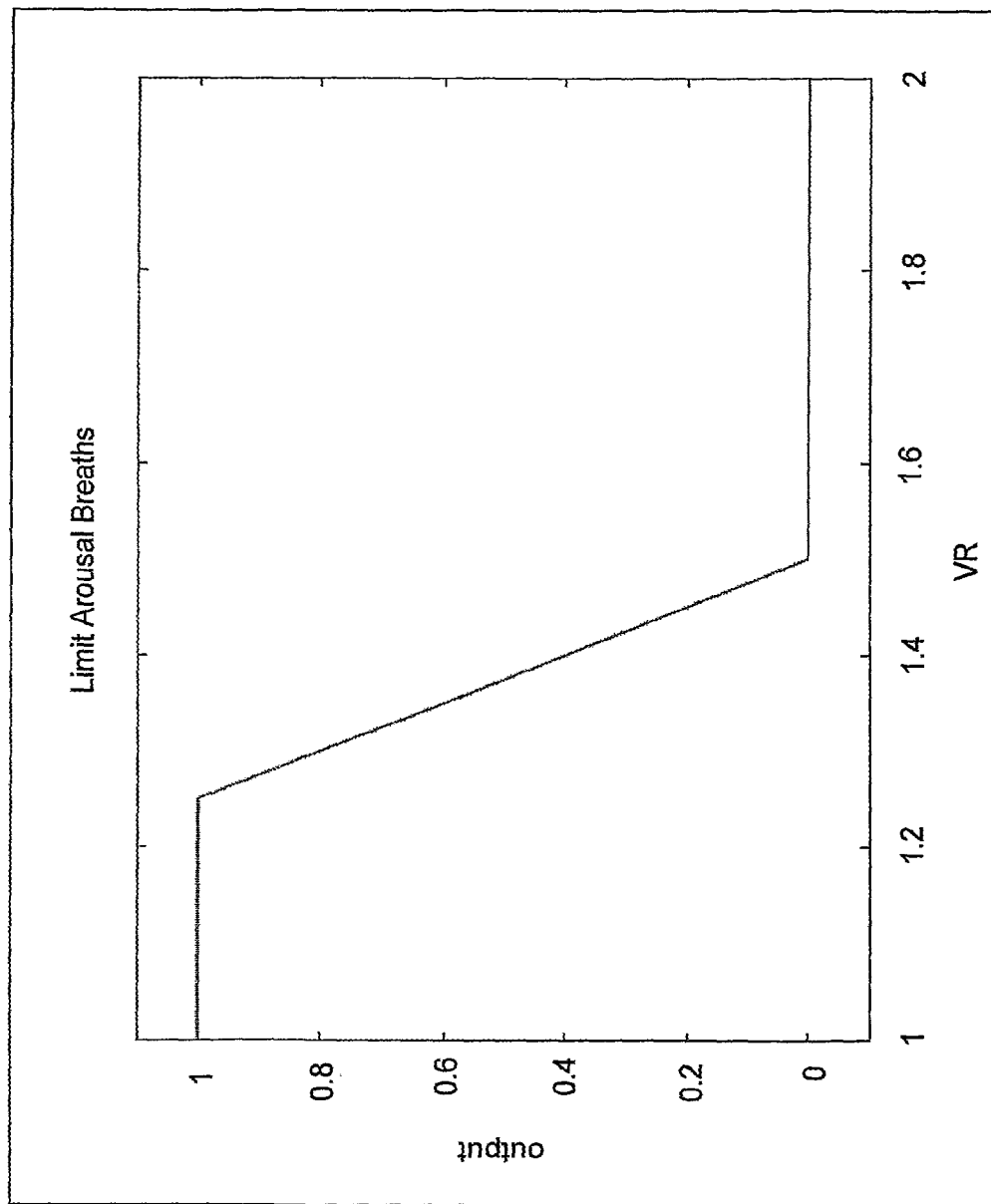
FIG. 12 shows an example function for modifying the detection capability of the flow limitation or partial obstruction measure based on a measure of ventilation.

In one embodiment of the system, the flow limitation measure may be derived so as to avoid treatment of other potential detected conditions. For example, it is possible for an arousal breath to be flat in shape or M-shaped, thus potentially indicative of a flow limitation based on a determination with the shape indices, but the breath actually may be of a stretched inspiratory time and thus not indicative of actual flow limitation in the patient. Thus, the flow limitation measure may be derived so as not to treat such a breath as flow limited. One manner of doing so is to modify the fuzzy outputs of the fuzzy rules from tables A, B, C, and D so as to adjust the combinations that use the breath duty cycle measure TTR with the function illustrated in FIG. 12. Essentially, the fuzzy outputs resulting from the rules based on a combination of the duty cycle measure TTR (e.g., the rules of tables B and D) are multiplied by the output of the function of FIG. 12 before defuzzification. Thus, if the ventilation ratio is approximately one or less, the result of each particular rule is left unchanged. As the ventilation ratio measure VR increases, which indicates an increasing likelihood of an arousal breath, the output of the rules of tables B and D are progressively de-weighted according to the example function of FIG. 12 and by the multiplication operation until the ventilation ratio measure VR approaches 1.5. At that point, the result of the multiplication operation will render the output of the affected rules to be zero.

Based on the foundation of the foregoing building blocks (e.g., shape indices, fuzzy membership functions and variables, fuzzy rules etc.) a calculation of an embodiment of the flow limitation measure FFL in a flow limitation detection system can be further summarized with the following exemplary steps:

1. Breaths may be framed up from the patient flow signal in a typically way so as to distinguish and extract data representing inspiratory and expiratory waveforms from a flow signal.

2. The inspiration waveform may optionally be trimmed of any leading pause using a trimming method that allows for particular M-shapes. Such a method is described in section F herein.

3. The M-Shape and Fuzzy-Chairness determinations may be made based on the exemplary calculations illustrated in section B.

4. An augmented M-shape may optionally be calculated as the Fuzzy-OR of the M-shape shape index and the chair shape index (e.g., Fuzzy-Chairness).

5. A filtered single-breath flattening (SBF) shape index may be determined based on the exemplary calculations illustrated in section A.

6. Ventilation ratio (VR) and $T_i$-on-$T_{tot}$ ratio (TTR) may be determined based on the exemplary calculations illustrated in section G.

7. SBF, VR, TTR & augmented M-shape may fuzzified into variables as per the exemplary membership functions previously described.

8. Fuzzy rules may then be applied according to the matrices of tables A, B, C, and/or D as previously described.

9. Fuzzy rules from tables B and D that use the breath duty cycle measure TTR may be optionally modified by the "Limit Arousal Breaths" function previously described with respect to FIG. 12.

10. Each fuzzy rule matrix is collected and defuzzified as detailed above separately.

11. This results in the following fuzzy outputs that are all fuzzy-OR-ed to give a flow limitation measure FFL such as:

$$FFL=\text{fuzzy-OR}(SBF\text{-}VR, SBF\text{-}TTR, M\text{-shape-}VR, M\text{-shape-}TTR)$$

Where:
SBF-VR is the deffuzzified result based on the rules of table A;
SBF-TTR is the deffuzzified result based on the rules of table B;
M-shape-VR is the deffuzzified result based on the rules of table C; and
M-shape-TTR is the deffuzzified result based on the rules of table D;

12. Next a Fuzzy Persistent Flattening measure (FPF) may optionally be calculated and fuzzy-OR-ed with flow limitation measure FFL by the following equation. Exemplary calculations of the measure FPF is described in section C herein. The adjustment of the FFL measure can be made by the following equation:

$$FFL=\text{fuzzy-OR}(FFL, FPF)$$

13. FFL is now modified according to the extent that the breath framing (e.g., the detection of inspiration or expiration waveforms) might be false such as utilizing the calculations described in section D herein. The resulting incorrect breath framing factor may be multiplied by the FFL by the following equation:

$$FFL=FFL*\text{Bad-breath-framing-factor}$$

14. This final FFL value may optionally be used in a ring buffer of a length, such as three, and the value of FFL that is ultimately used by a pressure setting algorithm can be based on a running average of the most recent FFL values of the buffer. A suitable equation for this operation may be:

$$FFL=\left(\sum_{i=1}^{3} FFL_i\right)/3$$

Figure 13:
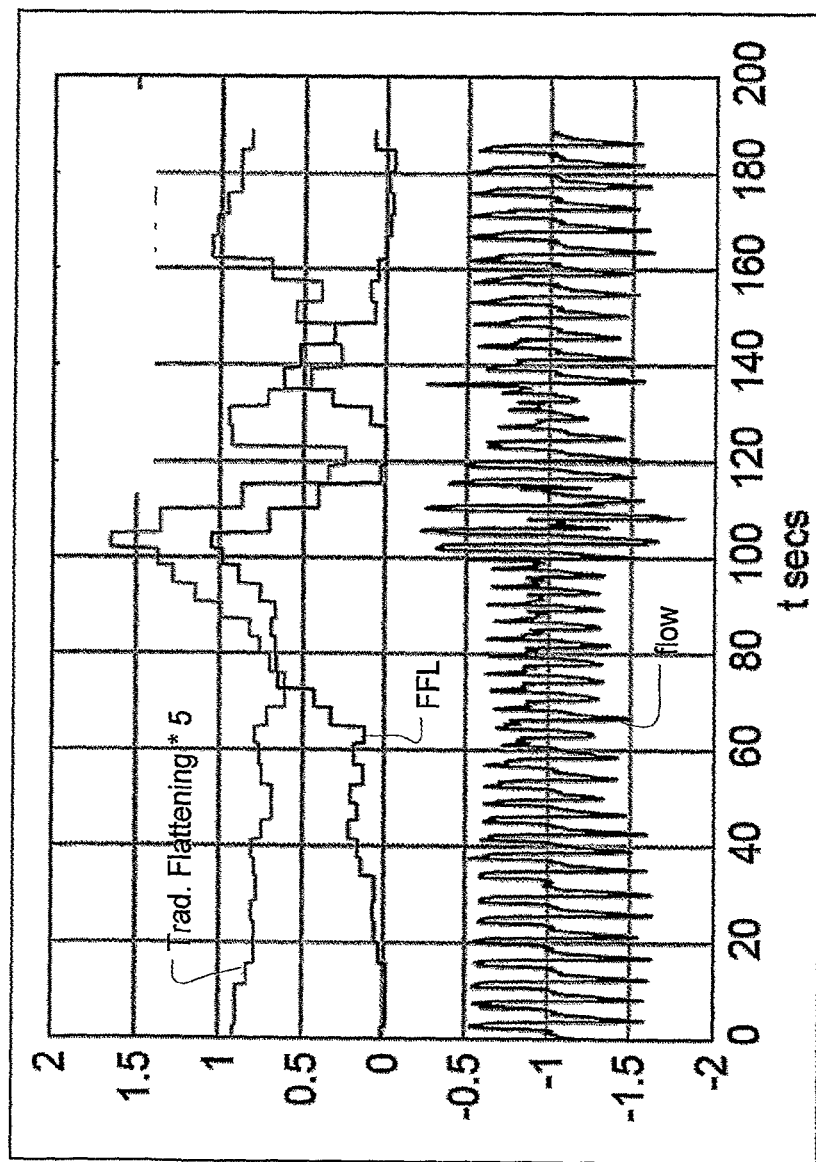
FIG. 13 is a graphical comparison of a traditional flattening index with a calculated flow limitation measure FFL of the technology described herein determined from the same flow signal.

FIG. 13 provides a graphic comparison between a traditional flattening index and a derived flow limitation measure FFL in accordance with steps of the above summary. The index and measure are based on the same flow signal shown in the bottom trace. The bottom trace flow signal includes a sequence of obstructed breaths ending in an arousal followed by some reasonably normal recovery breaths, and then some more obstruction. The breaths are initially "flat" and then progressively more M-shaped. In the top trace, the traditional flattening index initially falls then rises and finally falls sharply during the recovery breaths. The flow limitation measure FFL of the middle trace rises steadily both due to flattening and the M-ness shape of the breaths and then falls to zero when breathing in the flow signal becomes more normal.

The flow limitation measure may also be implemented in the control of a pressure treatment device. In one such embodiment, the measure may be implemented with any one or more of the following as follows:

1. Measure flow-rate at the flow generator (FG).
2. Measure pressure at the FG.
3. Using the flow-rate in step 1 calculate the pressure drop between the FG and the mask.
4. Calculate the pressure at the mask as the pressure at the FG minus the pressure drop calculated in step 3.
5. Using the pressure at the mask, calculate the flow through the vent in the mask (sometimes called intentional leak).
6. Subtract the vent flow from the flow measured at the FG to give the sum of patient flow (respiratory flow) plus any unintentional (mask or mouth) leak.
7. Filter the signal from step 6 to extract the DC (unintentional leak) component.
8. Subtract the DC component calculated in the last step from the flow calculated in step 6 to give patient flow (respiratory flow).

9. Filter patient flow lightly to remove unwanted higher frequencies such as by the method illustrated in section H herein.

10. Frame up breaths using patient flow in the usual way.

11. Any leading pause is trimmed from the front of the inspiration such as by the method illustrated in section F herein.

12. Once a complete breath has been framed (inspiration+expiration) calculate the following features:
 a. Length of any apnoea preceding the breath
 b. The inspiratory snore index (e.g., the mean of a snore signal over the course of the currently analyzed inspiration).
 c. The value of the filtered single-breath flattening index (SBF) for the currently analyzed breath such as by the method illustrated in section A herein).
 d. The value of the M-shape index for the current inspiration and the value of fuzzy-chairness for the current inspiration such as by the method described in section B herein. The values of M-shape and fuzzy-chairness are fuzzy-OR-ed to give the augmented M shape feature.
 e. The value of the ventilation ratio (VR) and the $T_i$-on-$T_{tot}$ ratio (TTR) for the currently analyzed breath such as by the method described in section G herein.
 f. Using SBF, VR, TTR & augmented M calculate FFL as detailed above.
 g. Using the currently analyzed expiration, calculate valve-like leak ratio.
 h. Measure the unintentional leak at the end of the currently analyzed expiration.
 i. Lookup the current setting for mask pressure, (i.e., the EPAP).
 j. Using the currently analyzed expiration, calculate the normalized expiratory peak location NEPL such as by the method described in section K herein.
 k. Look up the value of recent peak jamming.

13. The de-weighting factor is calculated as per the following pseudocode.

Section J describes example individual de-weighting functions that may be utilized.
 a. deweight=1.0
 b. deweight*=FFL_function_of_Leak (leak)
 c. valve-like leak*=valve_like_leak_function_of_leak (leak)
 d. deweight*=FFL_function_of_valve_like_leak (valve-like leak)
 e. deweight*=FFL_function_of_pressure (EPAP)
 f. deweight*=FFL_function_of_NEPL (NEPL)
 g. deweight*=FFL_function_of_Jamming (jamming)

14. The current threshold required for a pressure rise (current_crit_FFL) is then calculated using:

Current_crit_FFL=1.0−deweight*(1.0−crit_FFL);

15. The standard value of the unmodified crit_FFL is 0.05. So if, after all de-weightings are applied, deweight=1.0 then current_crit_FFL=0.05. Alternatively, if deweight=0.0 then current_crit_FFL=1.0.

16. The value of the pressure rise associated with FFL (the FFL "module") can now be calculated and "prescribed":

```
a. dp = 1.0 * (FFL − current_crit_FFL)
b. if (dp > 0.0) then
{
    max_dp = (EPAP-range-max − EPAP)
    if (dp > max_dp) then dp = max_dp
    if (dp > 0.0) then FFL-prescription += dp
}
```

```
else
    FFL_prescription = decay (FFL_prescription, Ti+Te, 20)
```

The last step simply decays the pressure exponentially over the time of the breath with a time-constant of preferably about 20 minutes.

17. Now the pressure rise due to snore may be calculated and "prescribed" and may utilize individual de-weighting functions as illustrated in section J herein:

```
a. Current_crit_snore = Snore_function_of_Pressure (EPAP)
b. Insp_snore *= Snore_function_of_VR (VR)
c. if (Insp_snore > Current_crit_snore) then
{
    dp = 1.5 * (Insp_snore − Current_crit_snore)
    max_dp1 = ttot * 0.2
    if (dp > max_dp1) then dp = max_dp1
    max_dp2 = ( EPAP_range_max − EPAP )
    if (dp > max_dp2) then dp = max_dp2
    if (dp > 0.0) then snore_prescription += dp
}
else snore_prescription = decay (snore_prescription,Ti+Te, 20)
```

18. Now the pressure rise due to apnoea may be calculated:

```
if ((apnoea_airway_closed && (apnoea_duration > 10)) then
{
    Head_room = (Max_Pressure_Apnoea − EPAP)
    if (head-room > 0.0) then
    {
        new_epap = Max_Pressure_Apnoea −
            head_room * exp(-ExpRiseTimeApnoea *
            apnoea_duration)
        if (new_epap > EPAP_range_max) then
            new_epap = EPAP_range_max
        apnoea_prescription += (new_epap − EPAP)
    }
}
else apnoea_prescription = decay (apnoea_prescription, Ti+Te, 20)
```

19. The new EPAP setting may then be calculated:
 a. EPAP=EPAP_range_min+apnoea_prescription+snore_prescription+FFL-prescription
 b. The new EPAP setting may then be achieved by raising the FG pressure in such a way that the mask pressure approaches the new EPAP value at a maximum slew-rate of 1.0 cmH$_2$O per second. Also, the treatment pressure is preferably only raised while the patient is in inspiration.

In still another embodiment of the technology, the flow limitation measure FFL may optionally be implemented as part of a respiratory effort related arousal (RERA) detector. In 1999 the AASM Task Force defined RERAs as:

"A sequence of breaths characterized by increasing respiratory effort leading to an arousal from sleep, but which does not meet criteria for an apnea or hypopnoea. These events must fulfill both of the following criteria:

1. Pattern of progressively more negative esophageal pressure, terminated by a sudden change in pressure to a less negative level and an arousal
2. The event lasts 10 seconds or longer."

In 2000, the study "Non-Invasive Detection of Respiratory Effort-Related Arousals (RERAs) by a Nasal Cannula/Pressure Transducer System" done at NYU School of Medicine and published in Sleep, vol. 23, No. 6, p/763-771, demonstrated that a Nasal Cannula/Pressure Transducer System was adequate and reliable in the detection of RERAs.

By utilizing the technology described herein, a RERA detector may be based on a real flow signal derived from a flow-generator. For example, a flow limitation measure by any of the methods previously described may be determined based on a flow signal. A measure of arousal may then be derived as a function of the flow limitation measure and a further function of a measure of an increase in ventilation.

Thus, in one embodiment, the RERA detector may be based on the following methodology:

if there has been flow limitation recently (e.g., FFL is greater than (>) 0) followed by a ventilation step change (e.g., a big breath) then a RERA is detected.

Preferably, the measure is implemented as a continuous variable so that adjustments to a threshold based on experimental data can be made. This may be an alternative to a Boolean threshold on each input parameter which results in lost information). The following algorithm may be used:

1. Keep track of the three most recent FFL values in a rolling buffer.
2. Keep track of the three most recent ventilation ratios (VR is the ratio of the mean tidal volume to the current three minute ventilation).
3. Sum the three most recent FFL values and limit the result to the range [0.0:1.0].
4. Calculate the two most recent VR differences (i.e., $VR_n-VR_{n-1}$ and $VR_n-VR_{n-2}$).
5. Take the maximum of step 4 while limiting it to a value greater than or equal to zero.
6. Multiply the result of step 3 by the result of step 5 to give the RERA result.
7. The result of step six may be normalised by taking the square root of the result.
8. A threshold could be set where, if the result of step seven exceeds the threshold, a RERA is scored.
9. There should be breath(s) with a RERA score below the threshold between breaths which are scored as RERAs.
10. The buffer size is chosen as three because in extreme cases of UARS there are only three detectable breaths between arousals.

Figure 14:
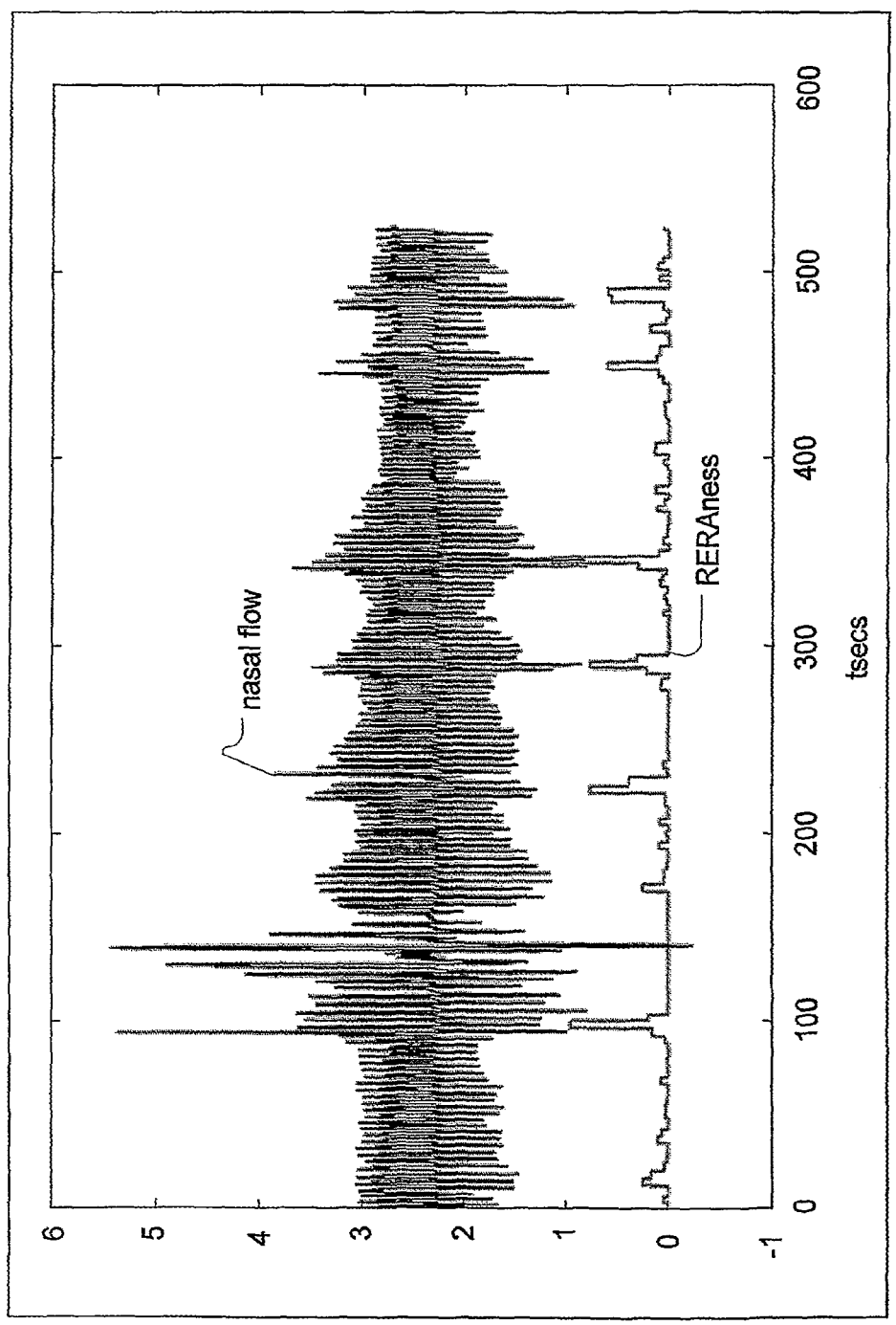
FIG. 14 shows a flow signal derived from nasal flow and the output measure of a continuous RERA detector quantifying the likelihood of a respiratory arousal.

As shown in FIG. 14, the bottom signal represents a continuous RERA Detector measure based on this methodology. The bottom trace show a detection of a respiratory effort related arousals based on the arousals of the top trace showing a flow signal.

The RERA Detector may be further implemented as part of a respiratory disturbance index. The RERA detector could be further used to calculate an RDI (Respiratory Disturbance Index in a diagnosis mode such as by the equation:

RDI=RERAs+Apnoeas+Hypopnoeas per hour

Alternatively, RERAs could be reported by a therapy device as an indication of the effectiveness of the therapy. Finally, the RERA index described herein could be used as input into a therapy algorithm. For example, the RERA index could be determined over a certain time frame, such as per hour, and the result may be used in an "outer loop controller" to set the threshold (or gain) for flow-limitation indices raising pressure. An example of an outer loop controller is described in WO 2005/051470 (PCT/AU2004/001652) assigned to ResMed Ltd., the disclosure of which is hereby incorporated herein by reference.

Figure 15:
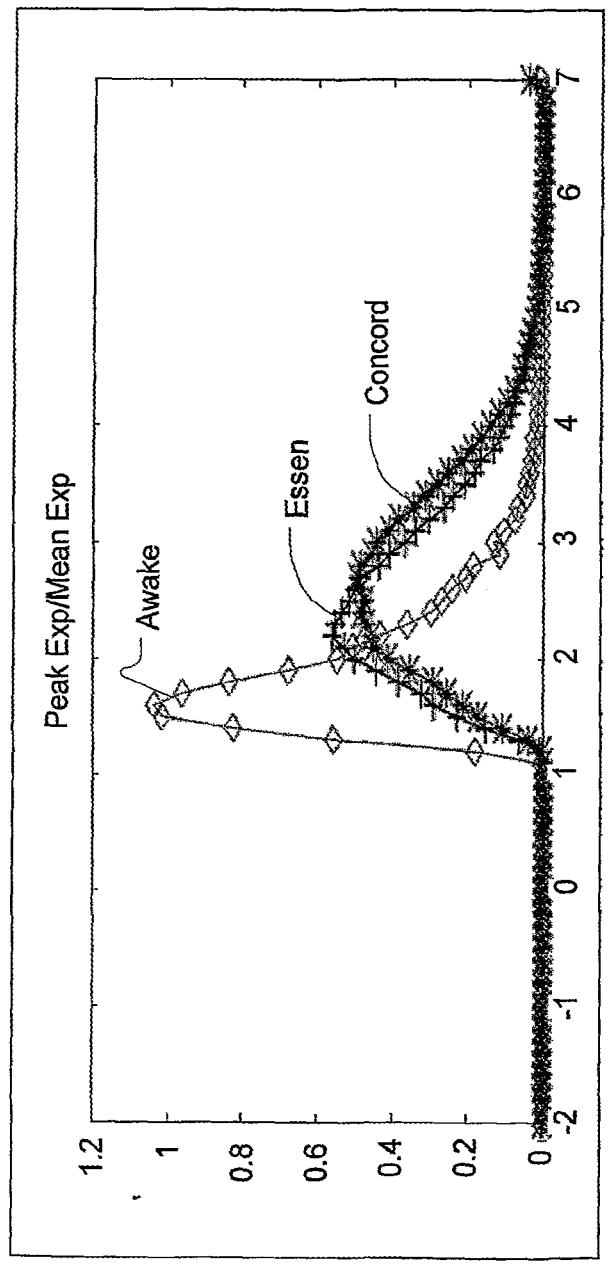
FIG. 15 illustrates a ratio of peak to mean expiratory flow that may be an index of sleep-wake-arousal detection.

A ratio of peak to mean expiratory flow may be used as another type of index of sleep-wake-arousal detection. The ratio of peak expiratory flow to mean expiratory flow may be part of the sleep-wake/arousal detection. FIG. 15 includes a histogram comparing awake normals with two sleep datasets. Awake breaths tend to be "flatter", i.e., the peak is closer in value to the mean. By comparing a threshold, such as 0.5, with the ratio, a RERA may be considered to be detected.

Section A—Single Breath Flattening

One embodiment of a single breath flattening index may be calculated by the following method as follows:

1. Frame up breaths.
2. Extract the inspiration part of the breath.
3. Trim any trailing or leading pause as required.
4. Interpolate the resulting inspiration over a standard grid of N points (normally N=65).
5. Divide the point y values by a factor such that the breath area is normalized to one with unity base length.
6. Calculate the rms value of the difference of the middle half of the points from one.

The flow signal that is used to calculate flattening may be called (amongst other things) "patient flow". This flow signal can be the result of filtering a raw flow signal with a filter such as a "10 Hz" filter although filter types may vary. The filter preferably reduces unwanted signal content such as that caused by turbulent flow and snore. The filter may also attenuate cardiogenic content slightly. The filter is a trade off between accurately detecting zero crossing points on the one hand and rejecting unwanted signal on the other. For example, if the filter were made more aggressive to reject all cardiogenic oscillations, breath detection could be rendered inaccurate. However, once breath detection is complete, further filtering may occur as desired.

Optionally, a filtered single breath flattening may be determined by the following:

1. Raw flow is filtered in the normal way to give patient flow.
2. Patient flow is used to frame breaths as usual.
3. Patient flow is continuously fed to an FIR filter that further attenuates unwanted signal components.
4. Because the FIR filter will have constant phase delay with frequency, we can pick the points required for the flattening calculation by simply accounting for the filter's delay.
5. Calculate flattening in the normal way.

Figure 16:
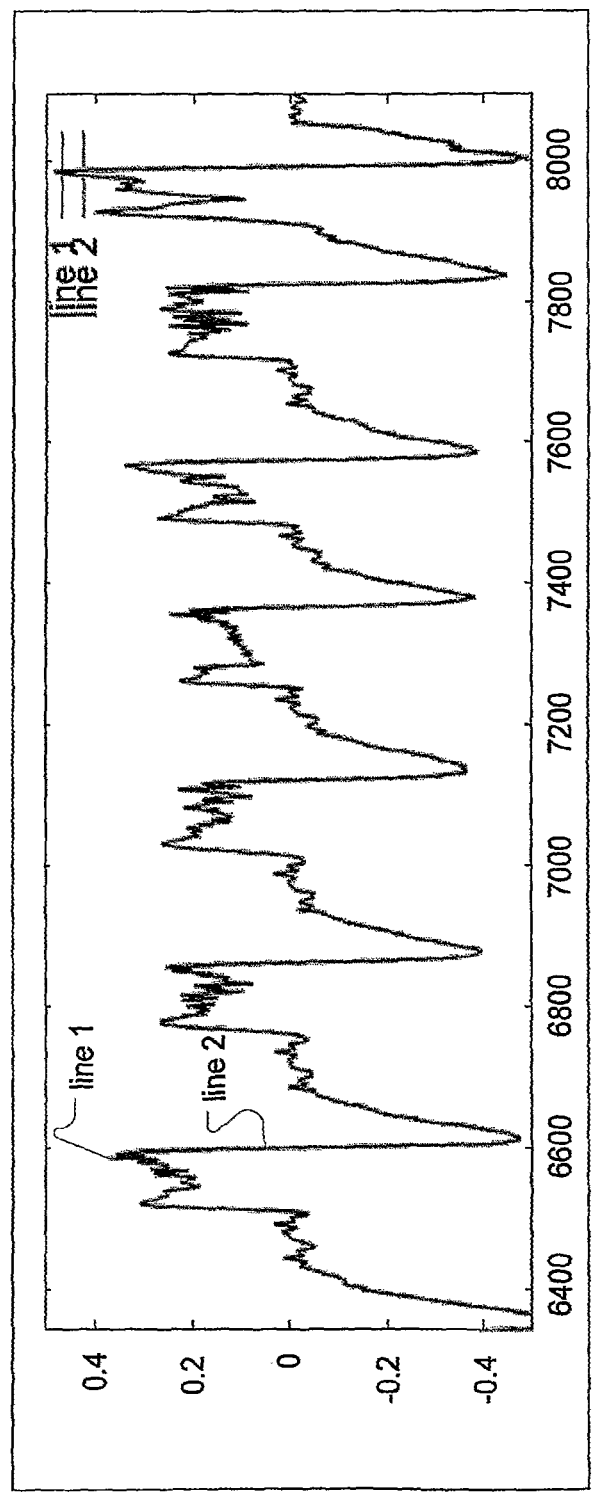
FIG. 16 is two superimposed filtered and unfiltered flow signals recording a sequence of obstructive breaths in the presence of a low-frequency snore.

FIG. 16 shows two superimposed flow signals recording a sequence of obstructive breaths where the normal calculation of flattening might be corrupted by (in this case) low-frequency snore. One of the signals has been filtered (and delay compensated) such that the snore is not evident. The filtered signal will give appropriately lower values of flattening calculated on a signal breath basis when compared to a calculation based on the other signal in which the snore is evident.

In the illustrated signals of FIG. 16, the last breath has traditional flattening values calculated as: 0.21 (based on the unfiltered signal) and 0.13 (based on the filtered signal). The latter value is indicative of a required pressure rise while the former is not indicative of a pressure rise. As an alternative to such filtering, a traditional five-breath point-wise averaging may also achieve this filtered result but at the expense of significant response delay.

Figure 17:
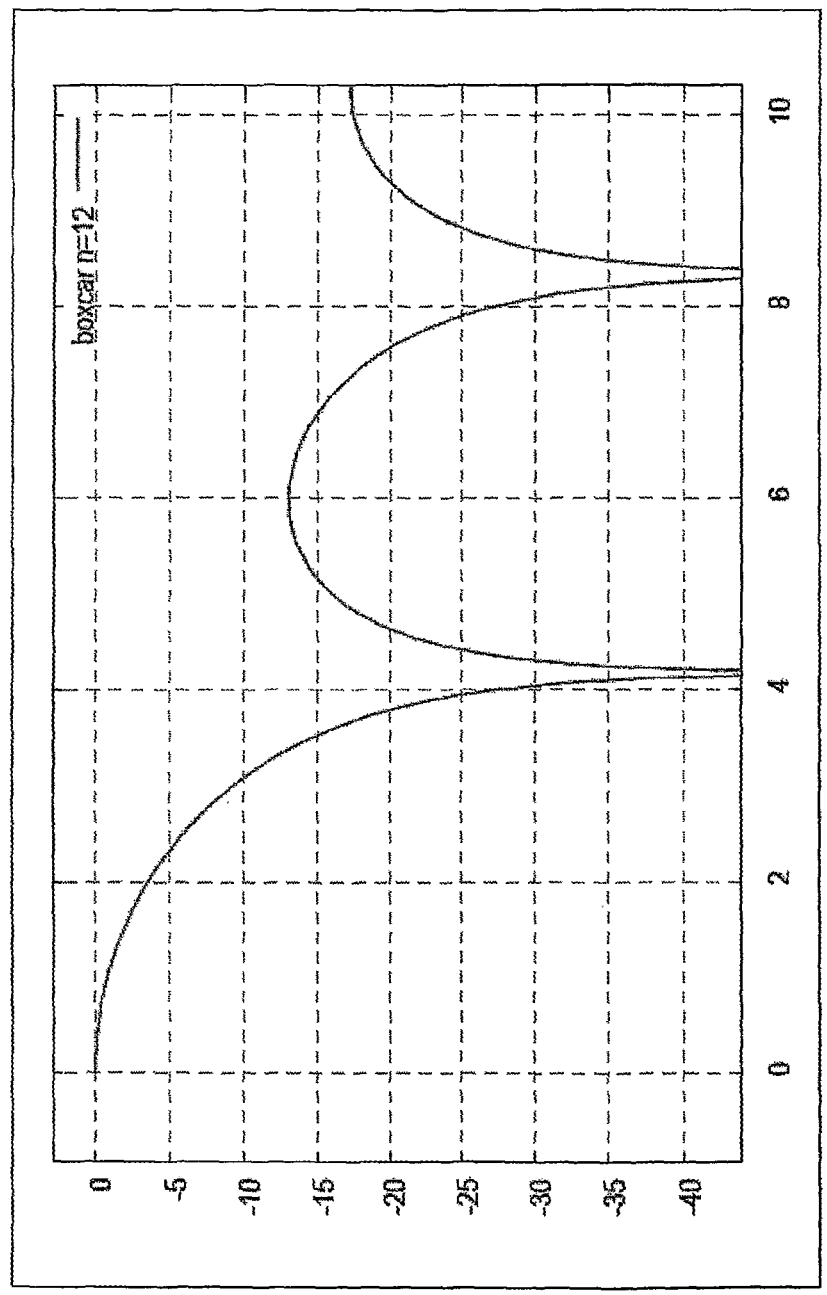
FIG. 17 illustrates a response of an example FIR filter useful for filtering an airflow signal.

A typical (and non-computationally-intensive) filter to use is a boxcar FIR filter. A boxcar filter of length 12 has a response illustrated in FIG. 17 at a sampling frequency of 50 Hz. The impulse response of the filter is not critical if there is a concern primarily with the signal of the middle half of each inspiration.

Section B—M-Shape Index and Augmented M-Shape

A suitable method for determining an obstruction measure such as an M-Shape index may be accomplished with the following algorithm. The index detects the presence of "M"

shaped breath patterns. Such an index may also be commonly considered an indicator of "u" shaped breath patterns. The obstruction measure may also be augmented or modified by an additional obstruction measure. For example, as will be described in more detail herein, an index of obstruction may be derived as a function of a first obstruction measure, such as an "M" shape index, and a second obstruction measure, such as an "h" or chair shape index.

For example, in some embodiments, each inspiration can be interpolated over a grid of N points, such as N=65. In this embodiment, two basis functions are calculated as:

$t=i/(N-1)$ where $i$ goes from 0 to $N-1$.

$B1=\sin(\pi t)$ $B2=\sin(3\pi t)$

These basis functions can then be stored for use with all subsequent calculations of the M-shaped index.

Each inspiration is then extracted and interpolated over a grid of N points. Two factors are then calculated as:

$F1=\text{sum}(B1 \cdot fs)$ $F2=\text{sum}(B2 \cdot fs)$

Where fs represents the interpolated inspiration points and · is the dot-product operator.

The final shape value is obtained by normalizing as:

$$\text{shape index} = \frac{F_2}{\sqrt{F_1^2 + F_2^2}}$$

Figure 18:
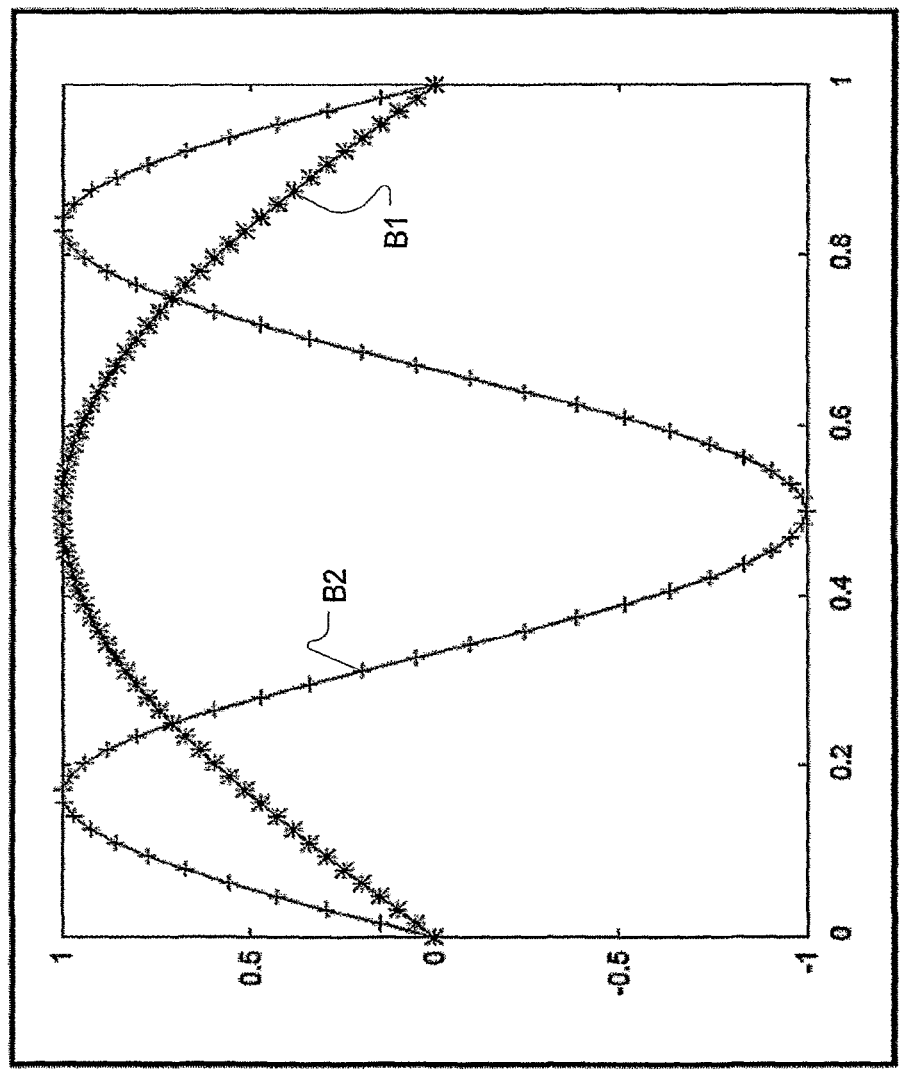
FIG. 18 plots example functions to serve as basis vectors B1 & B2 for detecting M-shape breathing.

This shape factor is then limited to vary between zero (purely sinusoidal) to one (very M-shaped). FIG. 18 plots suitable functions to serve as basis vectors B1 & B2.

Figure 19:
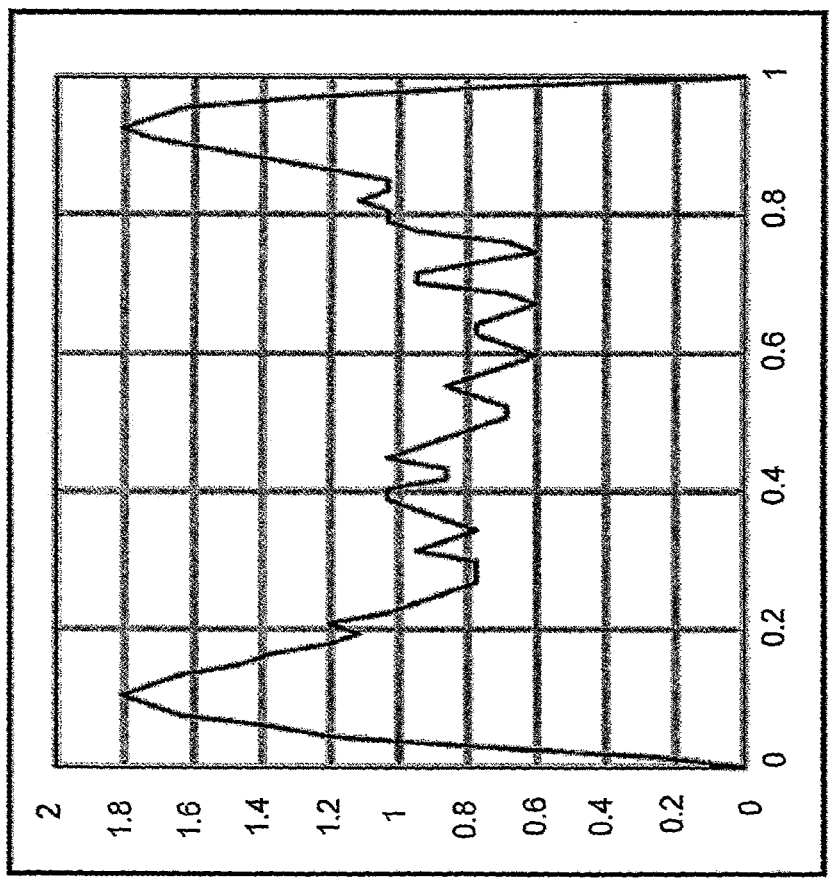
FIG. 19 is a graph of the flow signal for a typical M-shaped breath.

The flow signal for a typical M-shaped breath is plotted in the graph of FIG. 19. Based on the above methodology, calculations for the plotted breath are as follows:

F1=4.6082
F2=2.6538
Shape index=0.50

A typical non-flow-limited breath can have an M-shape index of only about 0.2.

Figure 20:
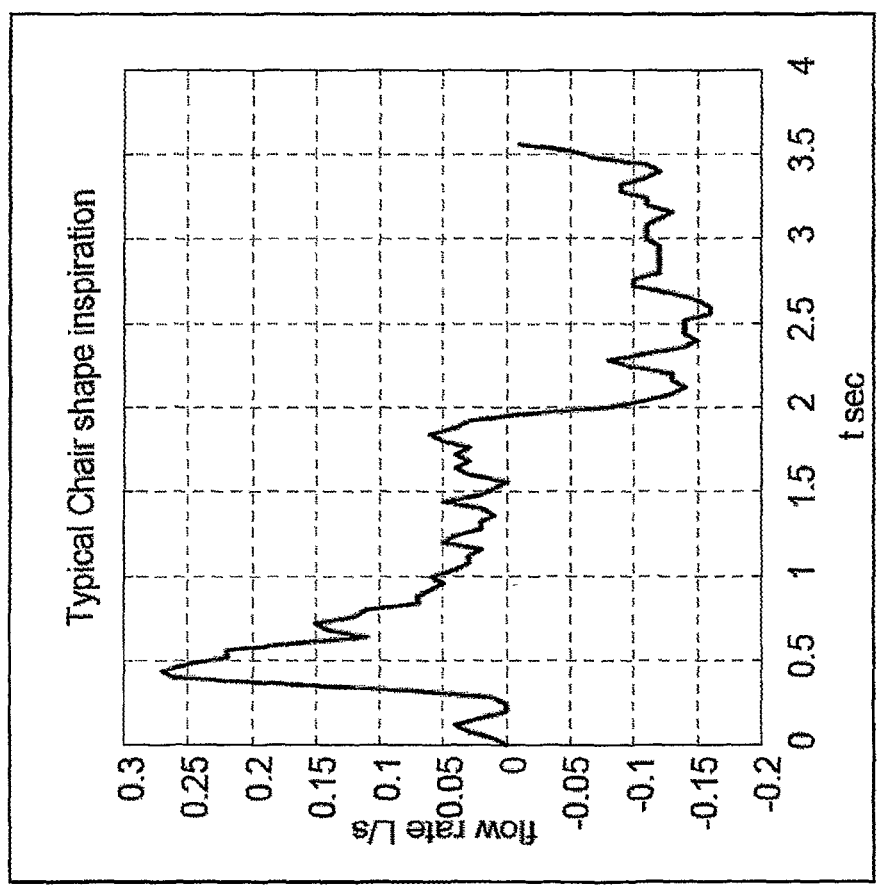
FIG. 20 is a graph of a flow signal showing an M-shape breath augmented by a simple chair shaping.

As previously described, an M-shape breath may be augmented by a simple chair shaping. This is illustrated in FIG. 20, which plots a flow signal having flow limitation that produces the augmented shape. The flow-limited inspiration shown in FIG. 20 (from t=0 to approximately t=2 seconds) has a typical "chair" shape. Such inspirations can be characterized by two features: 1) a high ratio of peak to mean inspiratory flow and 2) a normalized peak location close to either 0 (a left-backed chair as illustrated in FIG. 20) or 1 (a right-backed chair not shown)). In one embodiment, these indices can be are calculated as follows: Normalized Inspiratory Peak location (NormPeakLoc):

$$\text{NormPeakLoc} = \frac{(t_{peak} - t_0)}{(t_{end} - t_0)}$$

Where:
$t_0$ is the time at the start of inspiration;
$t_{end}$ is the time at end inspiration; and
$t_{peak}$ is the time at the peak inspiratory flow rate.
Ratio of Peak to Mean Inspiratory Flow (RPMIF):

$\text{RPMIF}=Q_{peak}/Q'$

Where:
$Q_{peak}$ is the maximum flow rate during the inspiration; and
$Q'$ is the mean flow rate over the inspiration.

Figure 21:
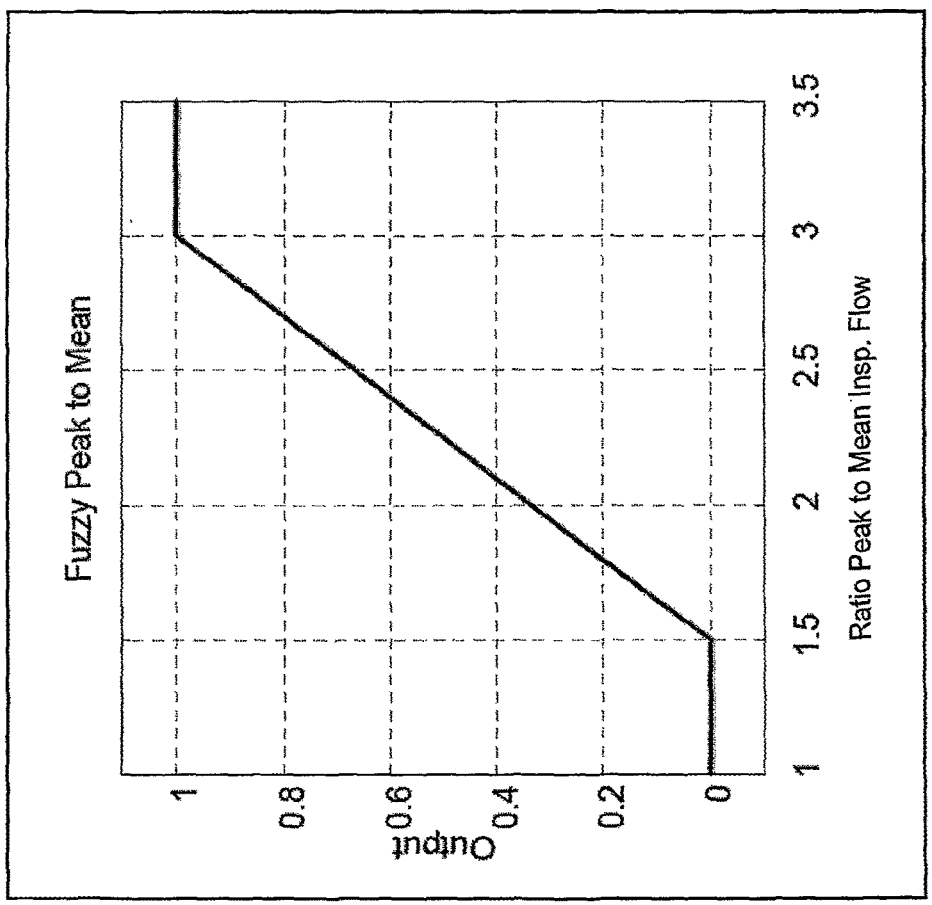
FIG. 21 is a graph of a membership function for a variable based on a ratio of peak to mean inspiratory flow useful for detecting M-shape breaths having a chair shape.
Figure 22:
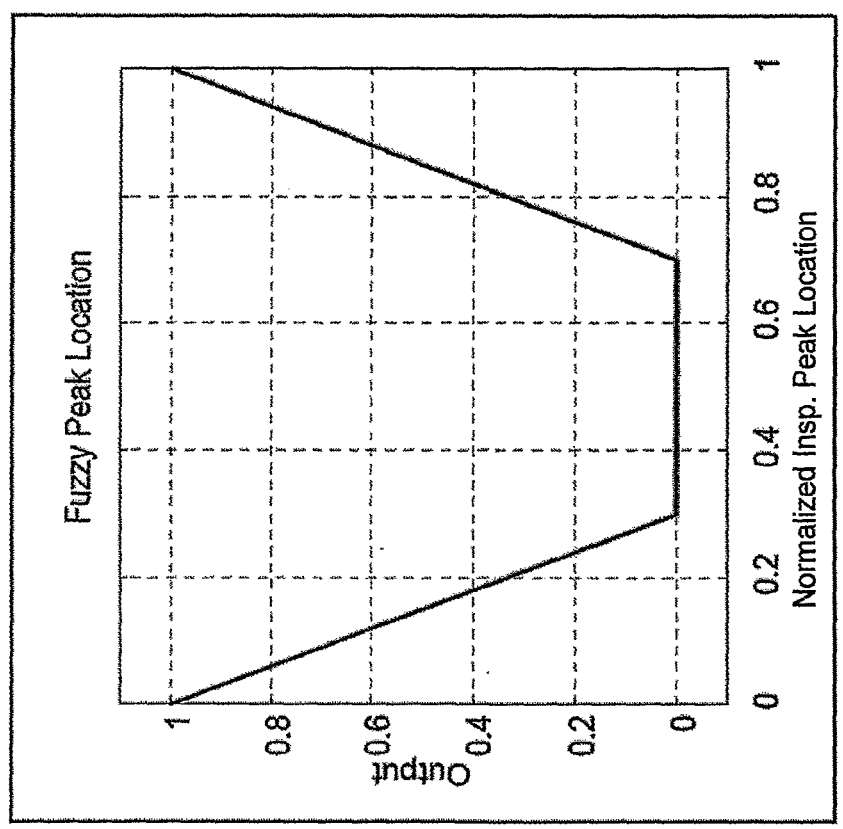
FIG. 22 is a graph of a membership function for a variable based on an inspiratory peak location useful for detecting M-shape breaths having a chair shape.

During quiet sleep a normal inspiration will have a normalized peak location of approximately 0.5 and a ratio of peak to mean inspiratory flow of 1.35. To measure "chairness", fuzzified versions of these features are utilized based on the graphs of FIGS. 21 and 22. The results of the above equations are applied to the mathematical functions of the respective graphs.

Once these fuzzy variables have been calculated, the final Fuzzy Chairness index is calculated as the fuzzy and of the results as follows:

Fuzzy_Chairness=Fuzzy-AND(Fuzzy_Peak_to_Mean,Fuzzy_Peak_Loc).

Figure 23:
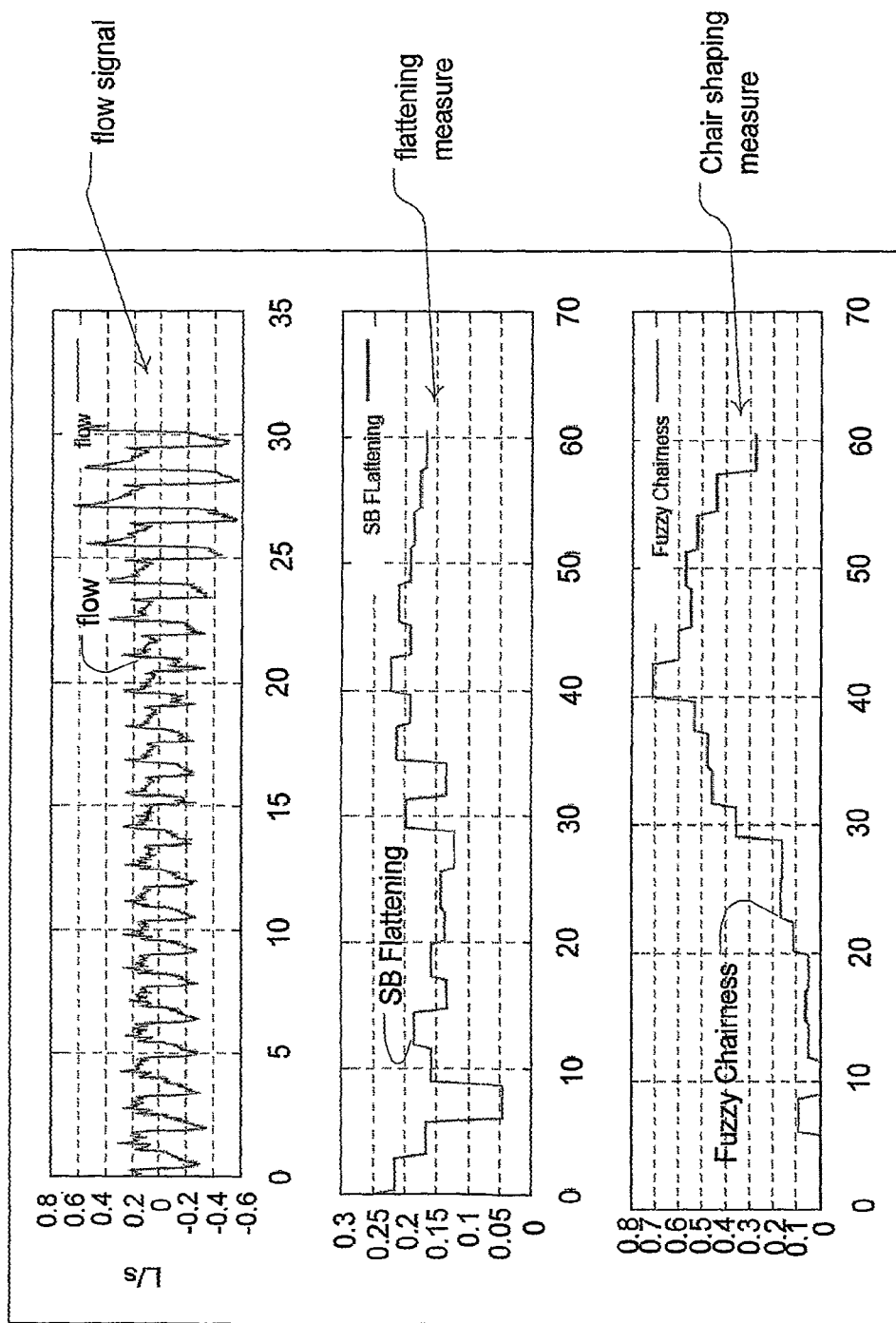
FIG. 23 shows a graph of a flow signal, a graph of a determined measure of flatness and a graph of a determined measure of chair shaping.

Based on this determination, the inspiration of FIG. 20 has a fuzzy chairness of 0.82. The scaling of the fuzzy chairness feature is such that it can be fuzzy OR-ed directly with the M-shape feature for a combined shape index. A fuzzy chairness of approximately greater than 0.3 implies flow-limitation. Fuzzy chairness can be described in English as: "if the ratio of the peak of inspiration to the mean of inspiration is high AND the location of peak inspiratory flow is near the beginning or end of inspiration THEN the inspiration is chair shaped." In FIG. 23, a typical flow sequence is shown where the inspiratory shape is initially flat such that an SBF index is approximately less than 0.2. However, the shape turns chair-shaped such that the SBF index (SB flattening) is approximately greater than 0.2 but the Fuzzy Chairness or the chair-shape index is approximately greater than 0.3.

Section C—Persistent Flattening

Figure 24:
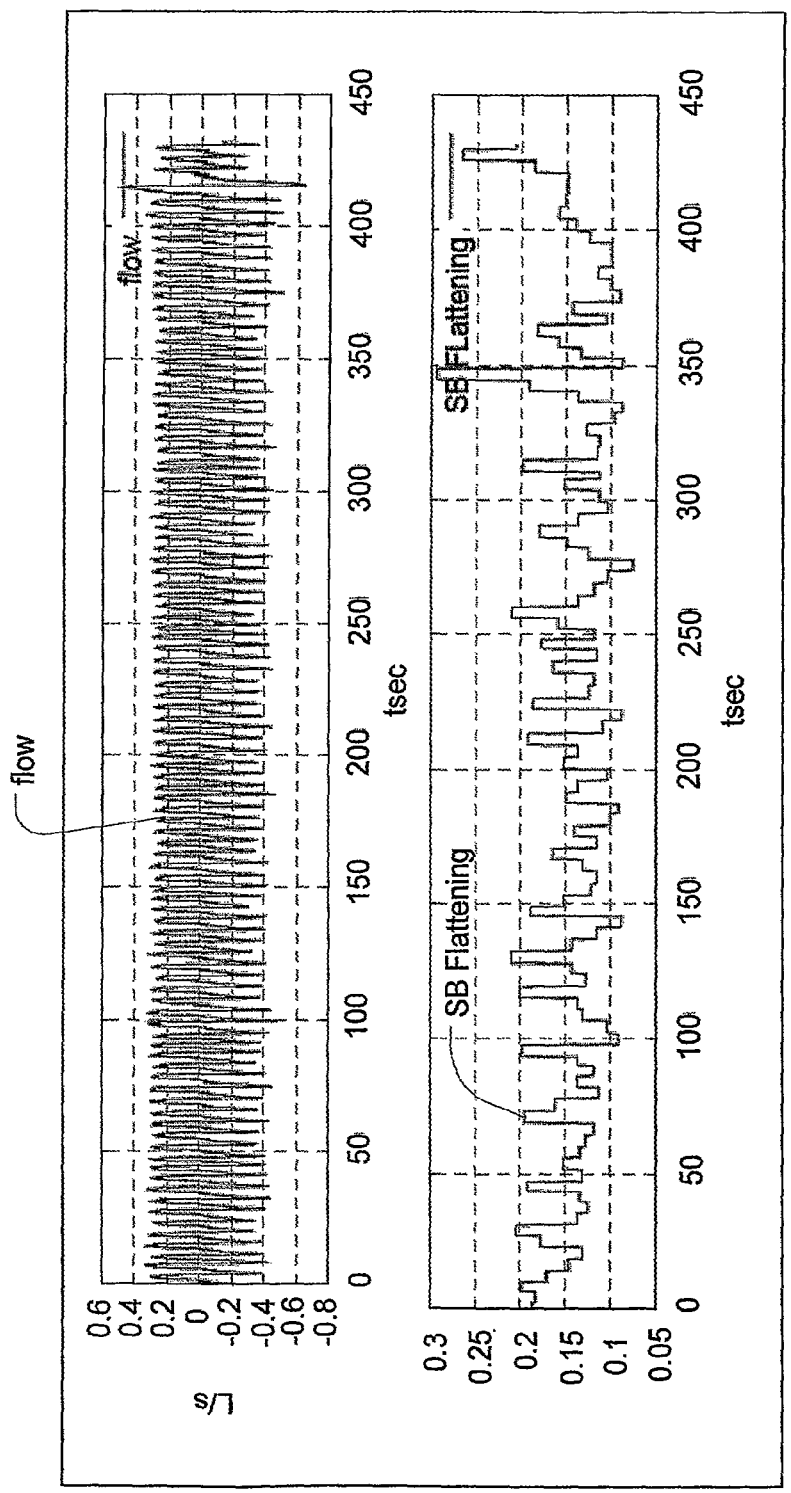
FIG. 24 shows a graph of a flow signal of a patient experiencing upper airway resistance with increasing breathing effort terminating in sleep arousal at t=420 and a corresponding graph of a single breath flattening index.

While the example flow-limitation measure FFL outlined above is designed to react to flow-limitation with both high sensitivity and specificity in a timely fashion, there are cases where it potentially fails to prevent arousal due to increased upper airway resistance. Consider the traces shown in FIG. 24 of a patient experiencing upper airway resistance with increasing breathing effort terminating in arousal from sleep at t=420 (big breath in upper panel). The lower panel of FIG. 24 shows a single-breath flattening index.

Figure 25:
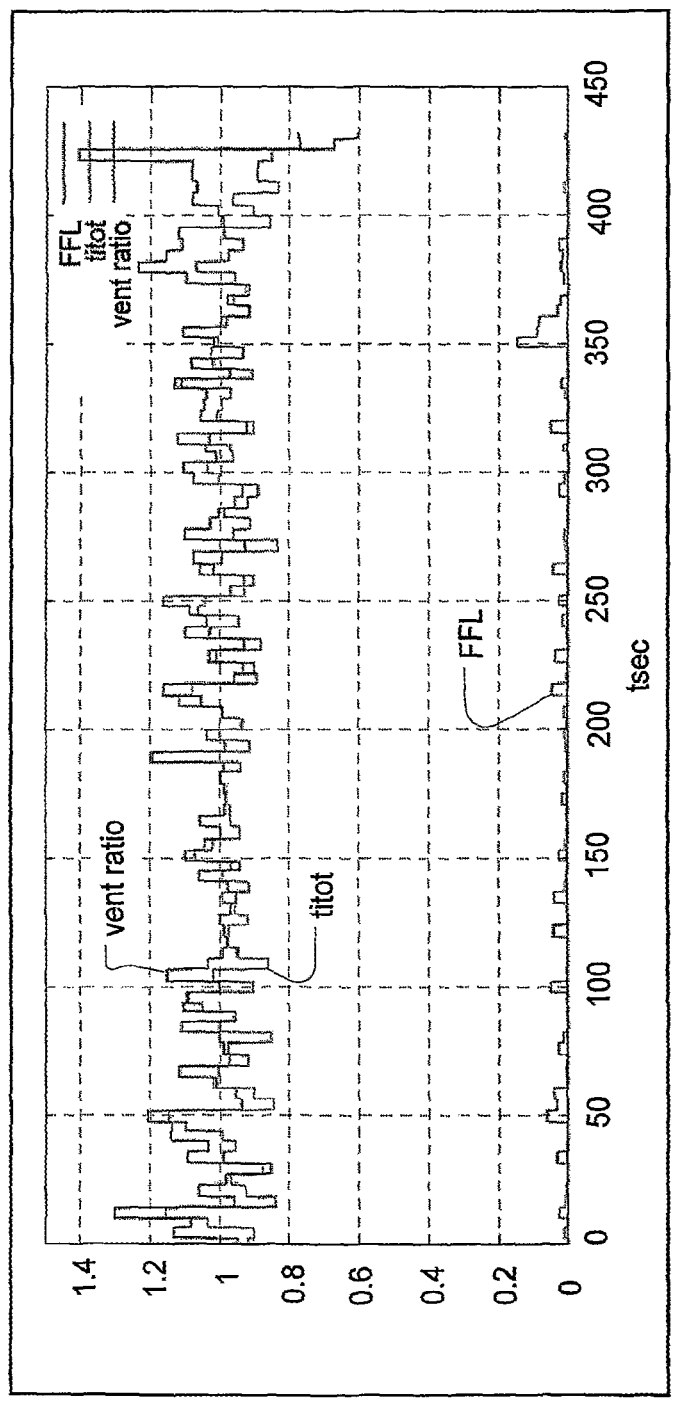
FIG. 25 shows a graph of an example flow-limitation measure, ventilation measure and duty cycle measure based on the flow signal of FIG. 24.

FIG. 25 shows why the FFL flow-limitation measure did not cause the pressure to rise in this sequence. The patient is maintaining their tidal volume (e.g., VR approximately 1) without stretching their inspiratory time as a function of total breath time (e.g., TTR approximately 1). Hence, despite a single-breath flattening index attaining low values, an FFL flow limitation measure fails to reach levels needed to raise the pressure adequately.

In order to deal with this situation, the system may optionally implement another obstruction measure. For example, a first obstruction measure may be derived from filtering a second obstruction measure such as a flattening index. This can provide an apparatus with some historic value associated with past obstruction. Optionally, the historic value may be reset if normal breathing is achieved (e.g., no obstruction) so that the history or filtered obstruction measure is an indicator of continuous or persistent past obstruction.

For example, a "fuzzy persistent flattening" may be implemented. As the name suggests, this fuzzy persistent flattening measure responds essentially to consistently low values of the flattening index. The measure is also implemented to respond slowly relative to the FFL flow limitation measure so that it does not interfere with the flow limitation measure FFL and over-treat the patient. Thus, the system preferably filters a single-breath flattening index in the following way:

A simple first order auto-regressive digital filter can be used such as one of the form:

$$Y_n = y_{n-1} + G(x_n - y_{n-1})$$

Where:

G is the gain of the filter.

A time constant twice as fast as five breaths in length may be established. So, for example, initially if a breath is considered 4 seconds long:

$$\text{Time Constant} = \tau = \frac{5 \times 4}{2} = 10$$

In order to allow for the fact that breaths might not be four seconds in length, a breath detection algorithm may be used to get the current respiration rate (RR, breaths per minute) which can be determined as an average of the five most recent breaths detected. This can be implemented as an adaptive time constant given by:

$$\tau = \frac{5 \times 60}{2RR}$$

So, if RR is 15 breaths per minute, which can be a common RR, the time constant would calculate to be 10 as before.

A suitable gain of the filter is given simply by:

$$G = \frac{1}{\tau}$$

The value to be filtered is a (filtered) single-breath flattening index. In order to prevent spurious values from corrupting the filtering process the system may optionally "head-limit" the incoming values. Thus, the values may be determined as a head limited flattening (HLF) index as follows:

---
if (SBF index > 0.3) then
    HLF = 0.3
else HLF = SBF index.
---

The output of the filter is a Persistent Flattening index (PF), and it can be initialized to an arbitrarily high value so that initially it has no effect on treatment such as: PF=1

Another feature of the filter is that a different gain is used for inputs that are less then the current value of PF than for values that are greater then the current value of PF as follows:

---
if HLF < PF then
    PF = PF + G(HLF − PF)
else
    PF = PF + 3 * G(HLF − PF)
---

This non-symmetry means that the filter will descend slowly to any persistently low inputs but will reset relatively quickly. This helps improve the noise threshold such that only consistently low values of flattening are responded to in a time frame shorter than the flow limitation measure FFL.

Next the value of PF is prevented from wandering away from a reasonable value with the following:

---
if (PF > 0.2) then
    PF = 0.2
else PF = PF
---

Finally, PF may be mapped to a fuzzy variable—fuzzy persistent flattening (FPF) such as by using the following equation:

$$FPF = \left( PF > 0.19 \text{ then } 0.0 \text{ else} \frac{0.19 - PF}{0.19 - 0.05} \right)$$

Figure 26:
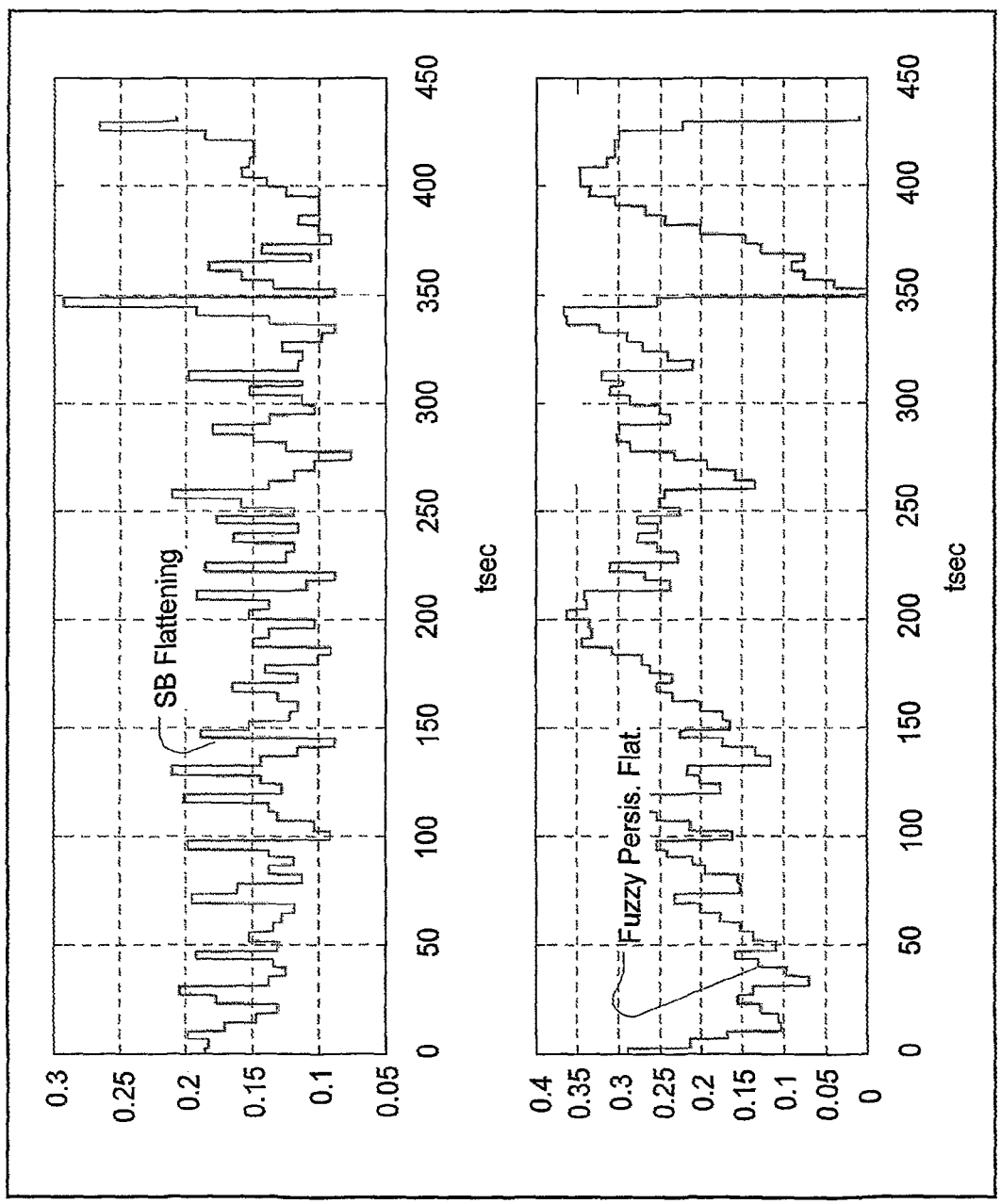
FIG. 26 is a graph of a persistent obstruction measure or persistent flattening measure based on the sequence of breaths shown in the flow signal of FIG. 24.

FIG. 26 illustrates the response of FPF to the same sequence of breaths shown in FIG. 24.

Section D—Bad Breath Framing

Figure 27:
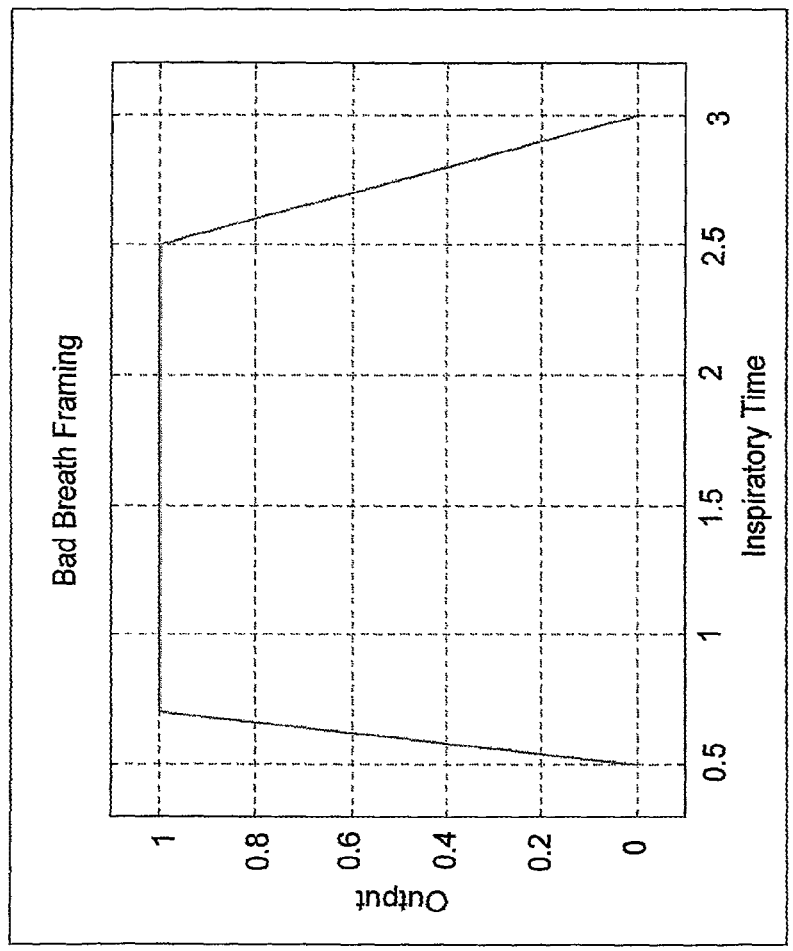
FIG. 27 illustrates a function for a de-weighting factor that can be utilized for modification of a flow limitation measure.

Occasionally a breath detection algorithm can frame up breaths incorrectly or a patient will cough or swallow causing a breath that provides little information about the current state of the airway. An optional heuristic may be used to de-weight breaths that are unlikely to be relevant based on the inspiratory time. Thus, a derived obstruction measure may be adjusted if a breath pattern that indicative of an inaccurately framed breath is detected. For example, FIG. 27 illustrates a function for a de-weighting factor that can be multiplied by a flow limitation measure (e.g., FFL). Breaths which are determined to be unrealistically long ($T_i > 2.5$ sec) or short ($T_i < 0.7$ sec) are progressively de-weighted.

Section E—Snore Entropy

Figure 28:
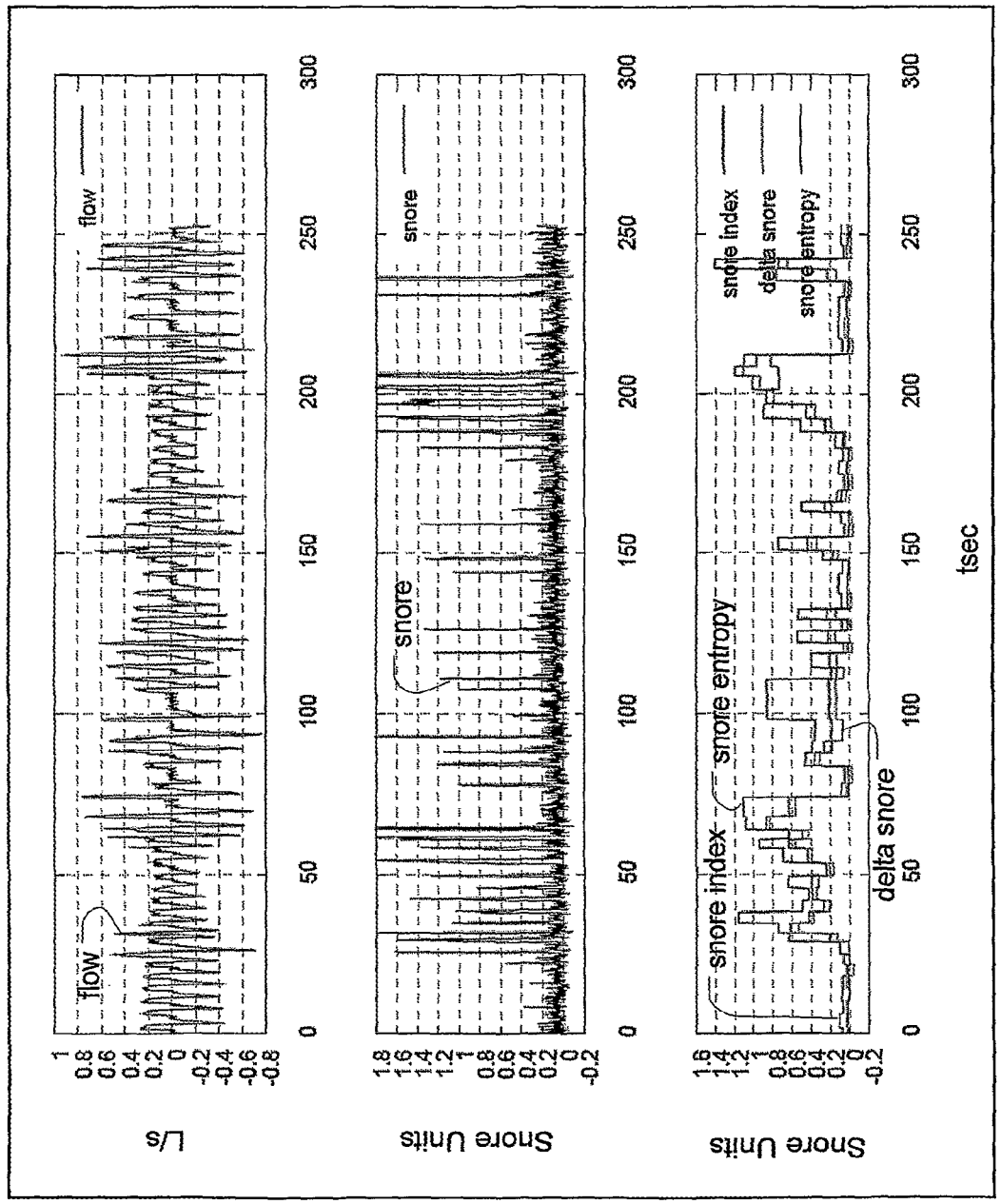
FIG. 28 presents a graph of a respiratory flow signal, a graph of an instantaneous snore signal and a graph of three snore indices.

Traditionally snore has been measured using the calibrated inspiratory snore index, which may be considered a measure of obstruction. FIG. 28 shows a typical sequence of snores captured while a patient was asleep. The upper panel shows respiratory flow-rate, the middle panel instantaneous snore (e.g., a measure of the acoustical power in the frequency range of interest) and the lower panel shows three snore indices. The calibrated inspiratory snore index (labeled "snore index" in FIG. 28) is calculated as follows:

the inspirations are framed up using the respiratory flow signal the instantaneous snore signal is adjusted to allow for background noise due to current conditions (e.g., set pressure, turbine speed etc.)

the snore index is calculated as the mean of the instantaneous snore signal over the course of each inspiration (i.e., approximately the mean acoustical power for each inspiration).

This technique is reliable when used to treat snore by raising the mask pressure in proportion to the measured snore index. However, the technique requires that calibration constants be measured for each flow-generator-mask combination and stored in non-volatile memory of the apparatus. Such calibrations are time-consuming and hence costly and may be subject to change with time.

Matthew Alder et al. teach in PCT Application number PCT/AU2007/000002 an alternative, labeled delta snore in FIG. 28. Delta snore is calculated as the difference between the mean of the instantaneous snore signal during inspiration minus the mean of the instantaneous snore signal during expiration. This is in essence a self calibration measure that assumes the background noise sources will vary little between inspiration and expiration. However, this is not always true.

In another alternative method, an inspiratory snore entropy method is implemented. In one example, this measure of obstruction is determined by filtering a measure of respiratory flow in a frequency range associated with snoring (e.g., 30 to 300 Hz). The magnitude of the power or energy of the filtered signal in the frequency range is then examined as a function of time to assess whether the power signal is indicative of some inspiratory shape or whether it is simply random noise. For example, a Shannon entropy function may be used. If the function indicates that the energy signal is merely random information or noise, then the snore index may be adjusted or de-weighted since real snoring may not be occurring.

Such a method uses the information contained in the instantaneous snore signal during inspiration. Such an index also does not require calibration, For example, the obstruction measure may be calculated as follows:

assemble a vector S of length n containing the instantaneous snore values for the inspiration in question if n<2 or n>an arbitrarily large value, give up and return zero subtract the floor of the snore vector and add one:

$S = S - \min(S) + 1$ calculate the area A:

$$A = \frac{\sum_{i=1}^{n} S_i}{n}$$

if A is <an arbitrarily very small value give up and return zero normalize the snore vector:

$$S = \frac{S}{A}$$

calculate the Shannon entropy (se) of the normalized snore vector:

$$se = \frac{1}{\ln(2)} \frac{\sum_{i=1}^{n} S_i \ln(S_i)}{n}, S_i > 0$$

optionally, the result may be scaled to approximate the inspiratory snore index as:

inspiratory snore entropy=10.0*se

Figure 29:
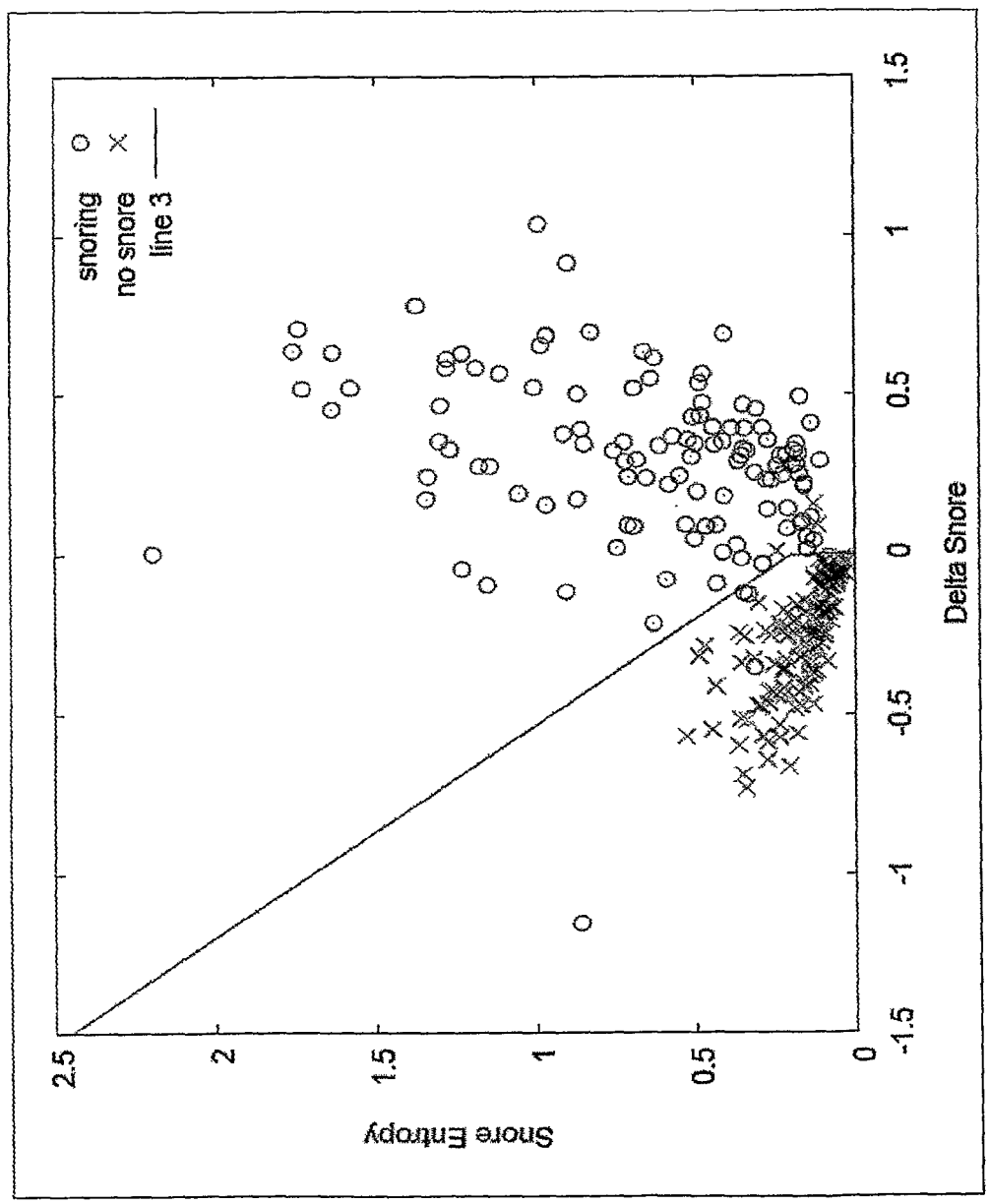
FIG. 29 shows a classifier for treating snore based on multiple snore indices.

Both delta snore and snore entropy are plotted in the lower panel of FIG. 28. As illustrated, the "snore entropy" trace tends to pick up spiky snores that have a low mean snore value (t=100). A judicious combination of both delta snore and snore entropy was found to correctly classify snores in nearly all cases. The graph of FIG. 29 shows one such arrangement. The classifier denoted by the plotted line can be stated as: "if delta snore is positive then treat, else if delta snore is negative then require progressively higher snore entropy with negative delta snore to treat."

Section F—Improved Trim Leading Pause

Figure 30:
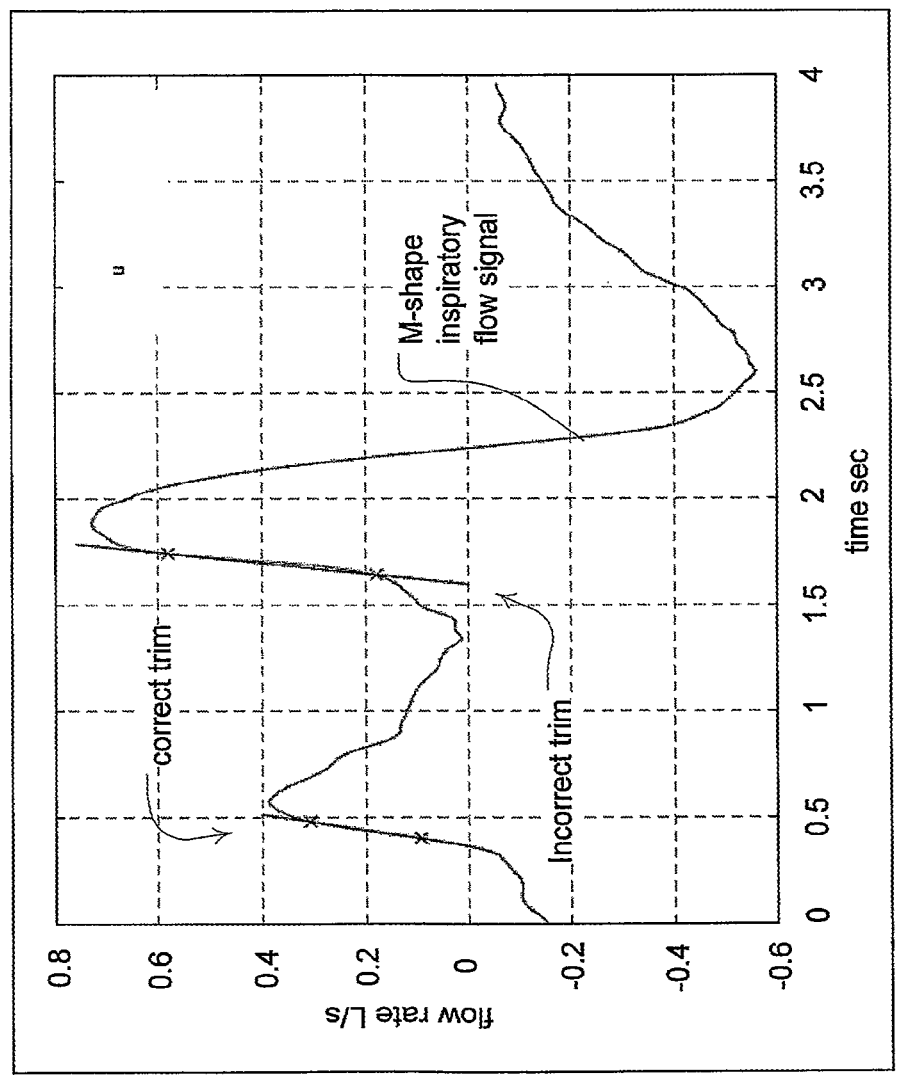
FIG. 30 is a graph of an M-shape breath with correct and incorrect trim results indicated thereon.

Some pressure treatment devices contain a function known as "trim_leading_pause". This function was designed to trim the front of the currently framed inspiration so as to remove any dangling expiratory pause from the previous expiration by detecting a peak and extrapolating backwards to an appropriate zero crossing that would be indicative of a beginning of inspiration. This function can fail on M-shaped breaths as illustrated in FIG. 30. FIG. 30 shows an incorrect trim (on the second peak) and a correct trim (on the leading peak).

The method can be modified such that it sets a boundary on where the peak of inspiration can be found that can assist with M-shape breaths. Thus, in case of an M shaped breath, the beginning of inspiration is determined by extrapolation from a first peak rather than a second peak of the inspiratory portion of the breath based on a boundary within inspiration. For example, this boundary may be calculated as follows:

1. Find the sum of the inspiration:

$\text{vol} = \Sigma_{t_0}^{t_1} Q(t) dt$

2. Find the point in the inspiration $t_{lim}$ such that:

$\Sigma_{t_0}^{t_{lim}} Q(t) dt > 0.4 \times \text{vol}$

3. Find the peak of the inspiration within $[t_0 : t_{lim}]$

4. Proceed with the current trim_leading_pause algorithm.

Figure 31:
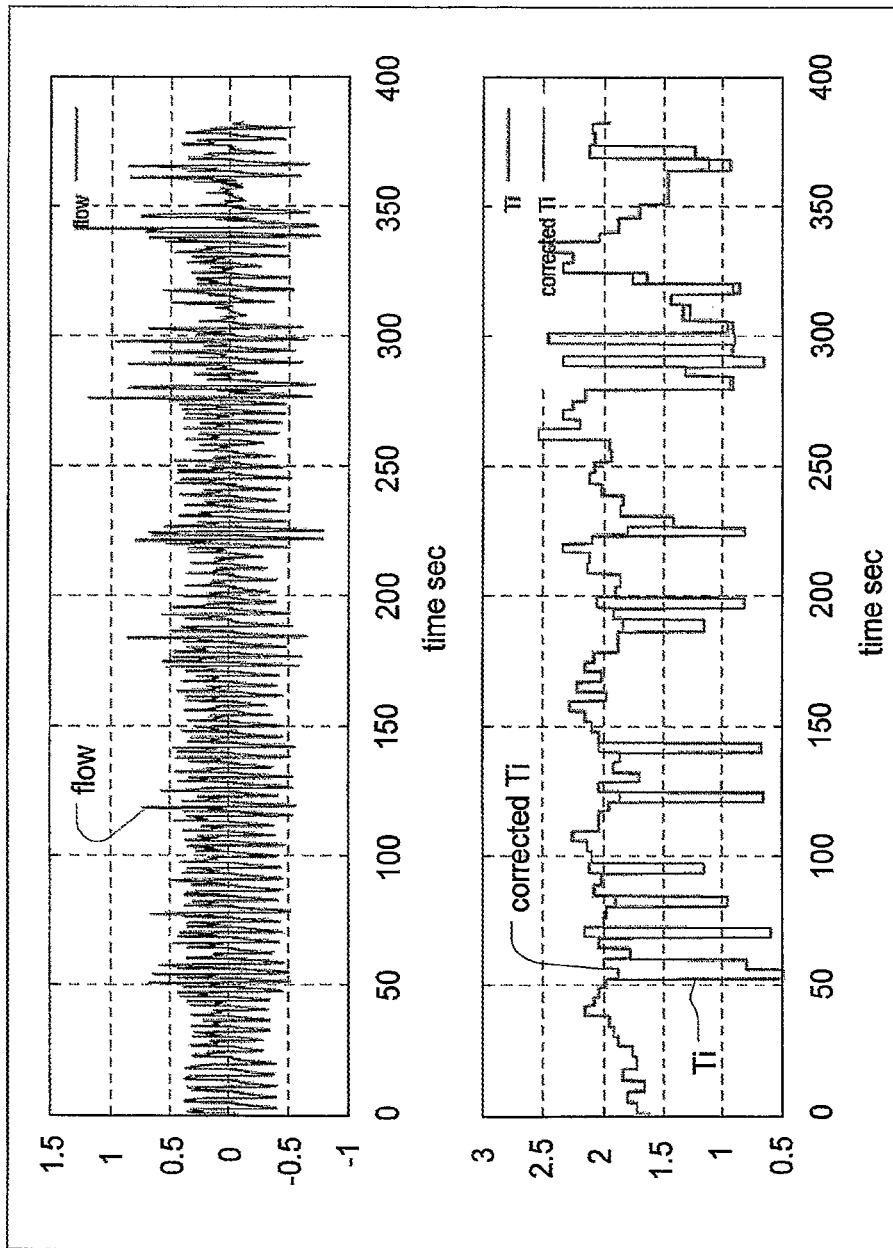
FIG. 31 includes a graph of a flow signal verses time including m-shape breaths and a graph of determined inspiratory time made by two methods.

The plot of FIG. 31 shows a sequence of flow-limited breathing in a flow signal with a number of breaths similar to that shown in FIG. 30. The top panel of FIG. 31 shows flow-rate plotted vs. time, the bottom panel shows the calculated inspiratory time ($T_i$) with trim_leading_pause applied. Both the current algorithm and the new algorithm ("corrected" $T_i$) results are shown. It can be seen that the current algorithm cuts some breaths in half resulting in artificially and incorrectly low values of $T_i$. The new algorithm implements "trim_leading_pause" in a consistent fashion.

Section G—Ventilation and Duty Cycle Measures (1) Calculation of Ventilation Ratio (VR)

A ventilation measure, such as the Ventilation Ratio (VR), may be determined as the ratio of the current breath-wise ventilation to the recent medium-term ventilation ($V_3$). In this example, medium-term can be a ventilation measure filtered using a filter with a three minute time constant τ. However, other time constants may be suitable. The filter used may be a simple first-order auto-regressive filter. Because the time constant of the filter is reasonably large, the filter will take some time to rise from zero. The measure will thus transition slowly between the reasonable ventilation value and the filter output during the time $[t_0 : 3 \times \tau]$. VR can be calculated as follows:

1. Set the gain of the filter to:

$$G = \frac{1}{f_s \tau}$$

Where:

$f_s$ is the sampling frequency;

τ is the time constant in seconds of the filter.

For example, if the sampling frequency is 50 hz and the time constant is 3 minutes then the G is calculated by:

$$G = \frac{1}{50 \times 180}$$

2. Initialize the filter to a reasonable ventilation value such as 0.2 liter/second.

3. Calculate patient respiratory flow ($Q_p$), that is total flow minus vent flow minus any mask leak, filtered appropriately.

4. Calculate medium-term ventilation:

$$V_3 = V_3 + G(Q_p - V_3)$$

5. During the transition period $0 < t \le 3\tau$:

$$V_3 = \frac{3\tau - t}{3\tau} \times 0.2 + \frac{t}{3\tau} \times V_3$$

6. Frame up the breaths in the usual way.
7. Once inspiration is confirmed, calculate the following:
inspired volume: $V_i$
inspiratory time: $T_i$
mean inspiratory flow-rate:

$$\overline{Q}_i = V_i / T_i$$

inspiratory component of ventilation ratio:

$$VR_i = \overline{Q}_i / V_3$$

8. Once expiration is confirmed, calculate the following:
expired volume: $V_e$
expiratory time: $T_e$
mean expiratory flow-rate:

$$\overline{Q}_e = V_e / T_e$$

expiratory component of ventilation ratio:

$$VR_e = \overline{Q}_e / V_3$$

9. Calculate VR as follows:

$$VR = \frac{VR_i T_i + VR_e T_e}{T_j + T_e}$$

(2) Calculation of a Duty Cycle Measure (e.g. TTR)

A duty cycle measure may be implemented for deriving a measure of obstruction as previously discussed. For example, from a measure of respiratory flow second ratio of duration of an inspiratory portion of a respiration cycle to duration of the respiration cycle as a function of the measure of respiratory flow. Similarly, a second such measure may be determined which may be subsequent in time to the first measure. The measure of obstruction may then be derived as a function of the first ratio and the second ratio.

A suitable duty cycle measure such as the $T_i$-on-$T_{tot}$ ratio (TTR) may be determined as the ratio of the current (breath) $T_i$-on-$T_{tot}$ value to the recent medium-term $T_i$-on-$T_{tot}$ value. Medium-term can be determined by filtering with a five minute time constant or other suitable time constant. The filter can be a simple first-order auto-regressive filter. TTR may be calculated as follows:

1. Set the gain of the filter to:

$$G = \frac{1}{f_s \tau}$$

Where:
$f_s$ is the sampling frequency;
$\tau$ is the time constant in seconds of the filter.
For example, if the sampling frequency is 0.25 hz (the approximate breath frequency) and the time constant is 5 minutes then the G is calculated by:

$$G = \frac{1}{\frac{1}{4} \times 300}$$

2. Initialize the filter to a reasonable value such as 0.4.
3. Calculate patient respiratory flow ($Q_p$), that is total flow minus vent flow minus any mask leak, filtered appropriately.
4. Calculate medium-term $T_i$-on-$T_{tot}$ as follows:

$$T_i T_{tot(5)} = T_i T_{tot(5)} + G(T_i T_{tot} - T_i T_{tot(5)})$$

5. Calculate TTR as follows:

$$TTR = \frac{TiTtot}{TiTtot_5}$$

Section H—De-Weighting Functions

Figure 32:
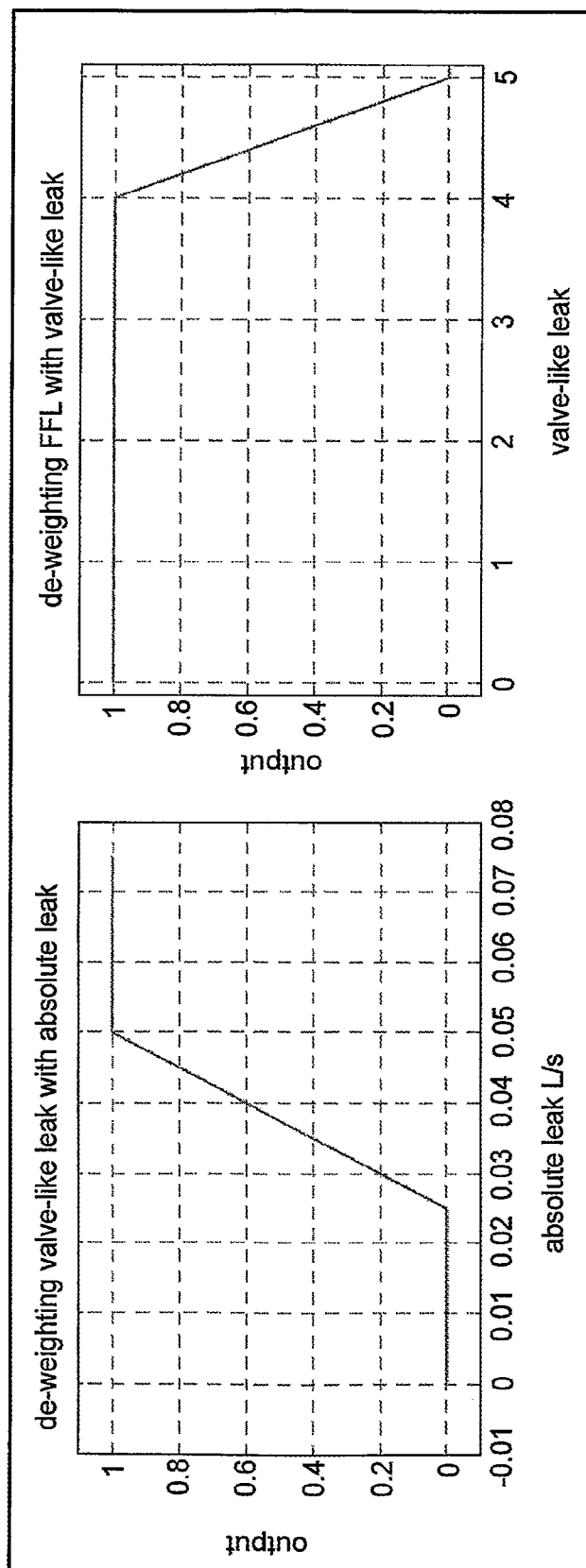
FIG. 32 shows graphs of functions useful for de-weighting a measure of flow limitation depending on leak conditions.
Figure 33:
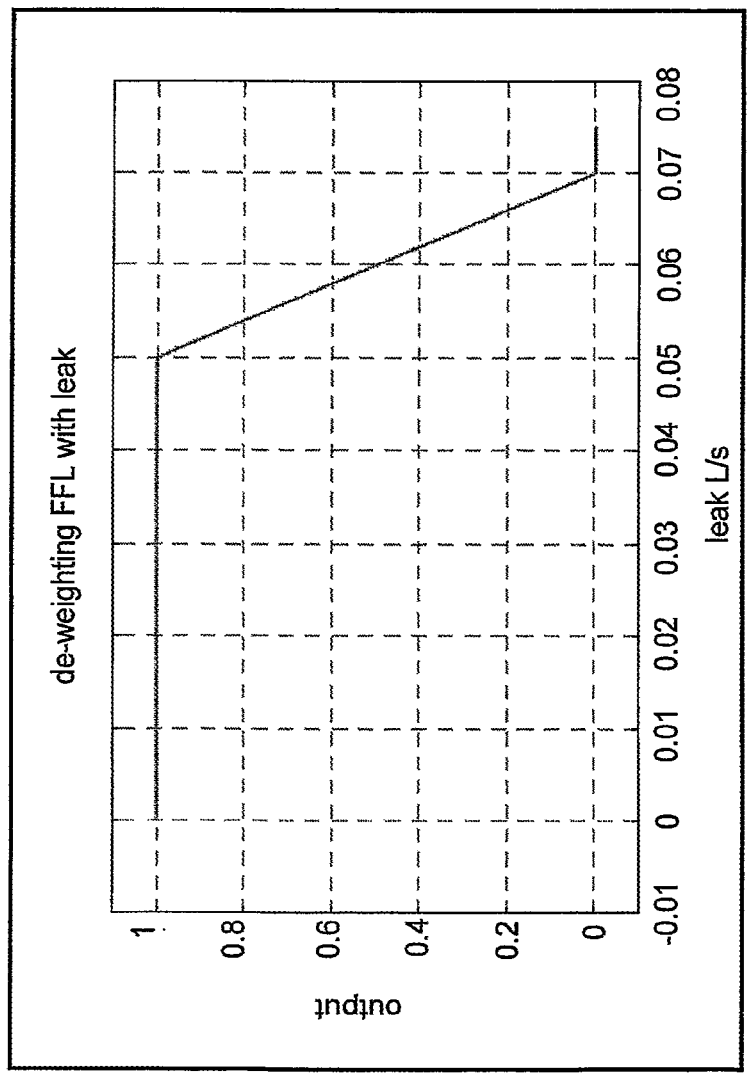
FIG. 33 is a further function useful for de-weighting the flow limitation measure or partial obstruction measure (e.g., FFL) based on leak conditions.

The functions graphed in FIGS. 32 and 33 can be used to de-weight the effect of a measure of flow limitation (e.g., FFL) or a measure of snore. The function can be applied to increase the threshold of the measures (e.g., FFL or snore) that needs to be exceeded for a pressure rise to occur. For example, a de-weighting function may involve a valve-like leak ratio. A valve-like leak measure can be calculated in a customary way such that its value varies between 0 and 5. In order to prevent spurious valve-like leak from preventing pressure rise when there is in-fact no leak occurring, the system may be implemented to de-weight a valve-like leak value to the extent that there is no absolute leak present. So the algorithm for determining de-weighting due to valve-like leak is as follows:

1. Calculate valve-like leak from the latest inspiration.
2. Determine the absolute value of the leak (the value at end expiration).
3. Multiply the value of valve-like leak by the output of a function of absolute leak such as the function illustrated by the graph at the left side of FIG. 32. For example, if the absolute leak is less than (<) 0.025 valve-like leak is set to zero. Alternatively if the absolute leak is greater than (>) 0.05 the value of valve-like leak remains unchanged and in the interval between 0.025 and 0.05 the value of valve-like leak is linearly diminished.
4. Use the value of valve-like leak with a function of leak such as the function illustrated in the graph at the right side of FIG. 32 to output a de-weighting factor. For example, for values less than (<) 4 the output is 1 and for values greater than (>) 5 the output is zero. In the interval between 4 and 5 the output decreases linearly from one to zero.

The de-weighting of the flow limitation measure (e.g., FFL) based on leak (e.g., L/s) can be done using the function shown in the graph of FIG. 33. For values of leak less than (<) 0.5 there is no de-weighting and the output is 1. For values of leak greater than (>) 0.7 there is complete de-weighting and the output is zero. There is a linear decrease in output from 1 to 0 for value of leak between 0.5 and 0.6.

Figure 34:
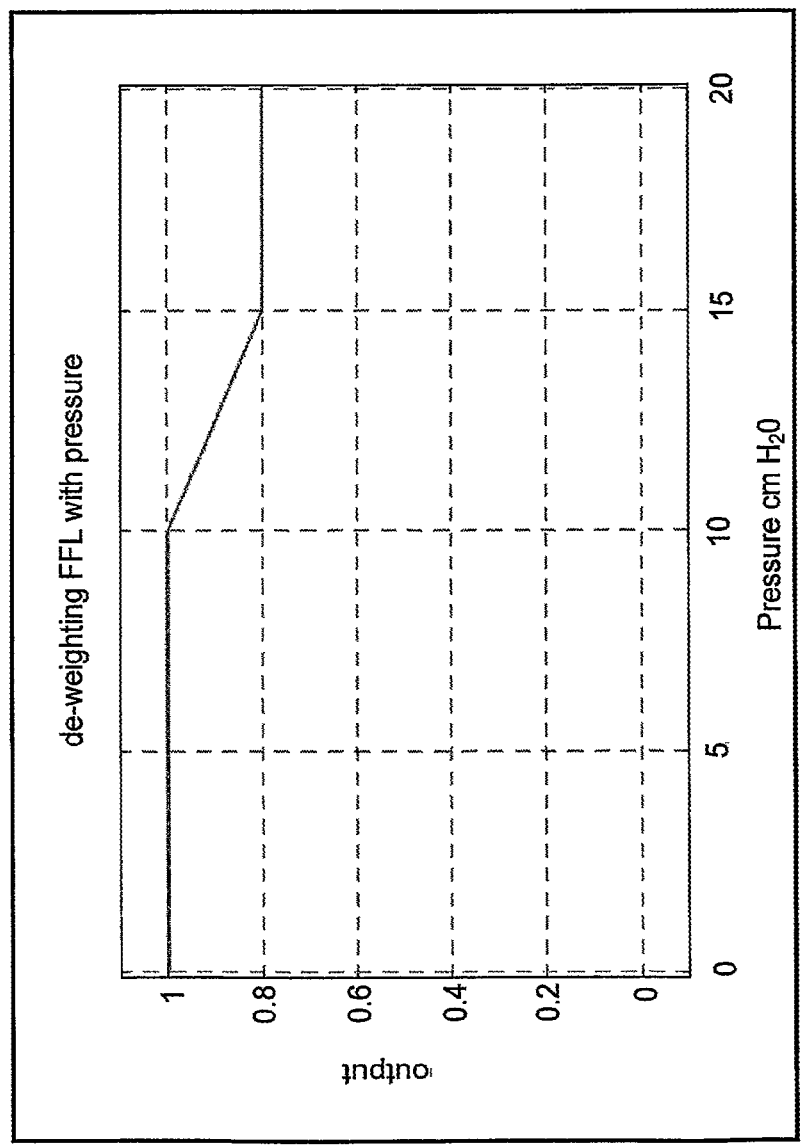
FIG. 34 is a graph of a function suitable for de-weighting a flow limitation or partial obstruction measure by a level of mask pressure.

The de-weighting of the flow limitation measure by pressure, such as the level of mask CPAP in cm $H_2O$, may also be accomplished using a function such as the example graphed in FIG. 34. In the example, for pressure levels less than 10 cm $H_2O$ there is no de-weighting and for pressures greater than 15 cm $H_2O$ there is partial de-weighting and the output is 0.8. For pressures between 10 and 15 there is a linear decrease of the output from one to 0.8. The output may then be multiplied by the measure of flow limitation.

Figure 35:
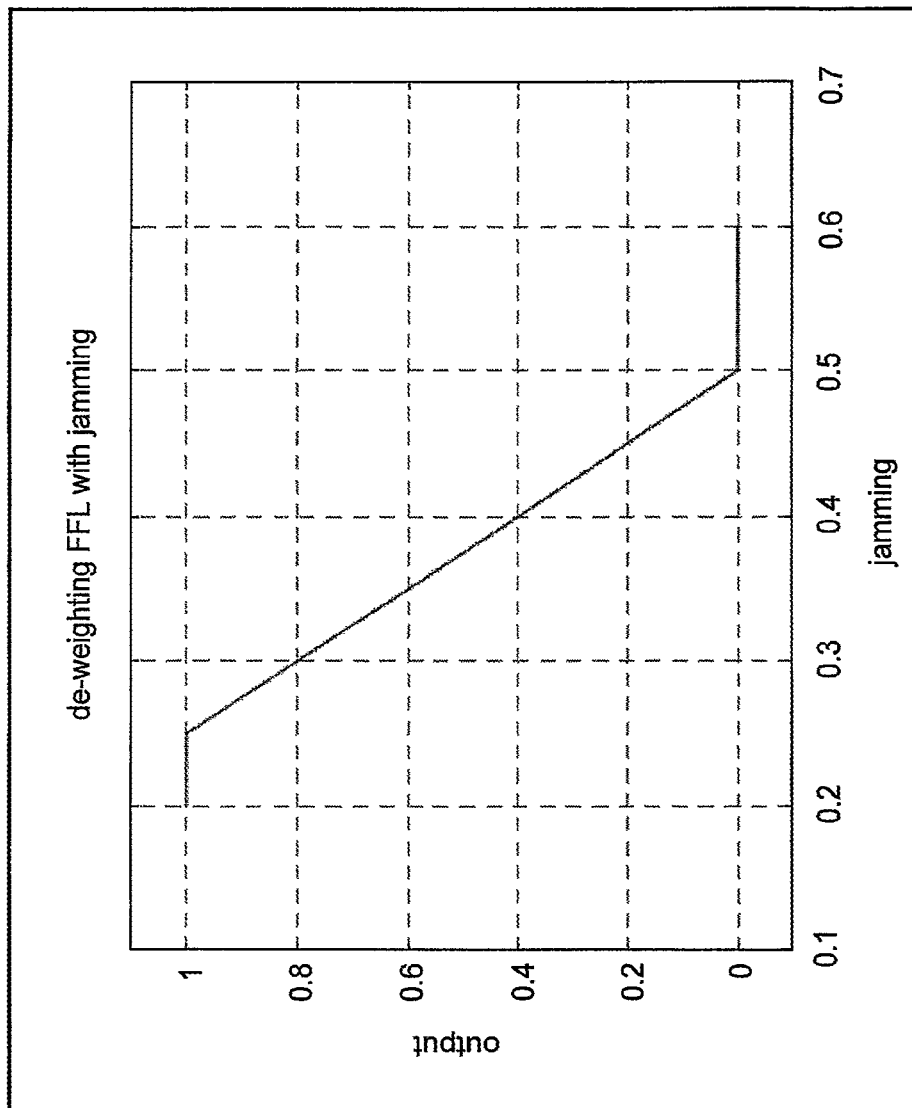
FIG. 35 is a graph of a function suitable for de-weighting a flow limitation or partial obstruction measure by a measure of jamming.

Finally, the effect of the measure of flow limitation or obstruction can be de-weighted with increasing Jamming. Jamming is a measure such as the fuzzy extent to which the current inspiration or expiration have been going on for too long. For example, Jamming may be determined by the methodology described in U.S. Pat. No. 6,484,719, the disclosure of which is incorporated herein by reference. High jamming is indicative of a transient change in the leak, for example, when a patient opens there mouth or when they shift in bed and change their mask position on the face. At high levels of jamming it is likely that the flow estimate is not accurate and that the leak constant is being reduced to help improve the flow estimate. While this is happening it is prudent to prevent pressure rises until things have calmed down. This can be accomplished by the example function of FIG. 35. When jamming reaches 0.25 the system can begin de-weighting until the measure is completely de-weighted at a jamming level of 0.5. The output of the function may be multiplied by the measure of flow limitation to effect the de-weighting.

Figure 36:
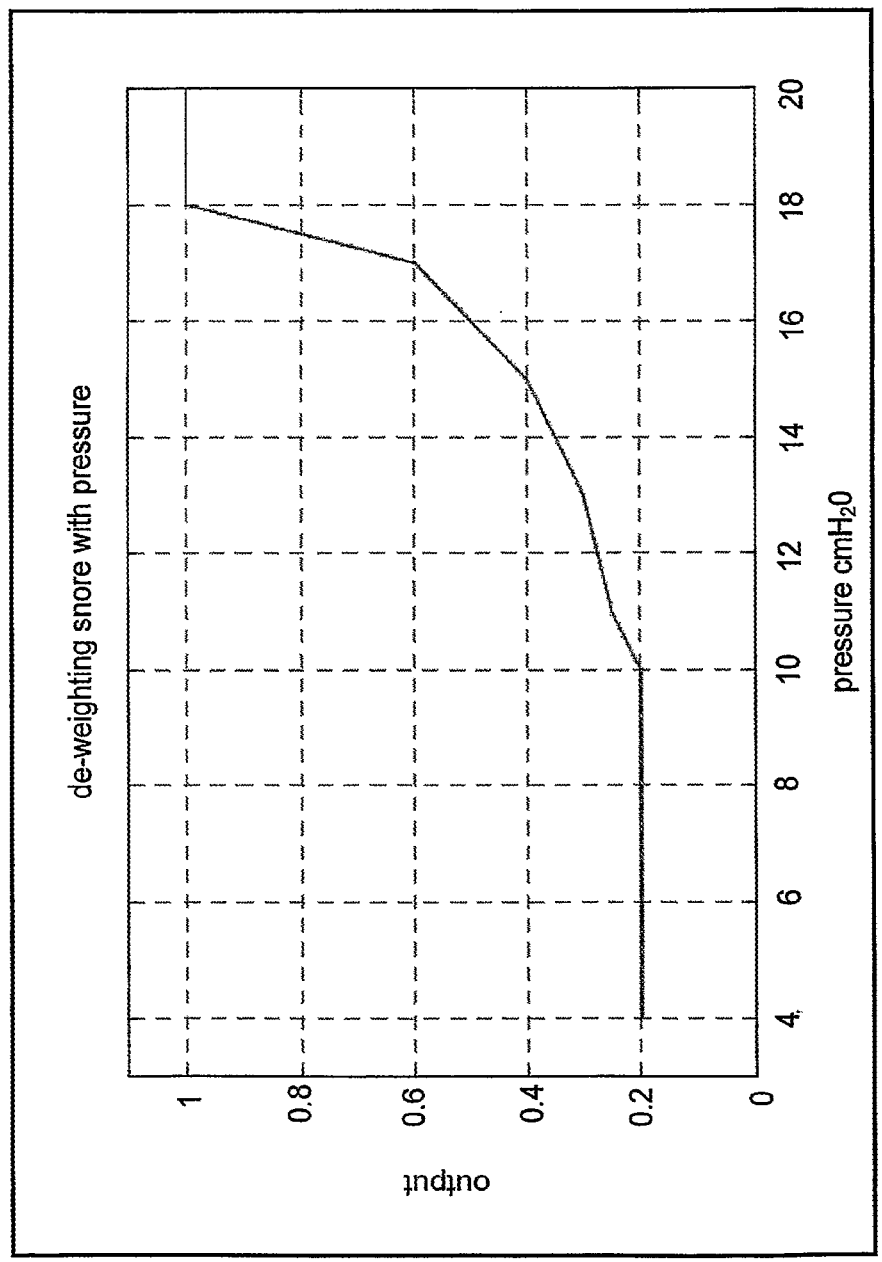
FIG. 36 is a graph of a function suitable for de-weighting a snore measure as a function of treatment pressure.

Similarly, a measure of snore may be de-weighted based on various conditions of the system. For example, a value of snore may be de-weighted by the function of pressure illustrated in FIG. 36. This makes the system less sensitive to the snore measure for purposes of generating a pressure rise. Thus, the value of snore required for a rise in treatment pressure increases with increasing pressure.

Figure 37:
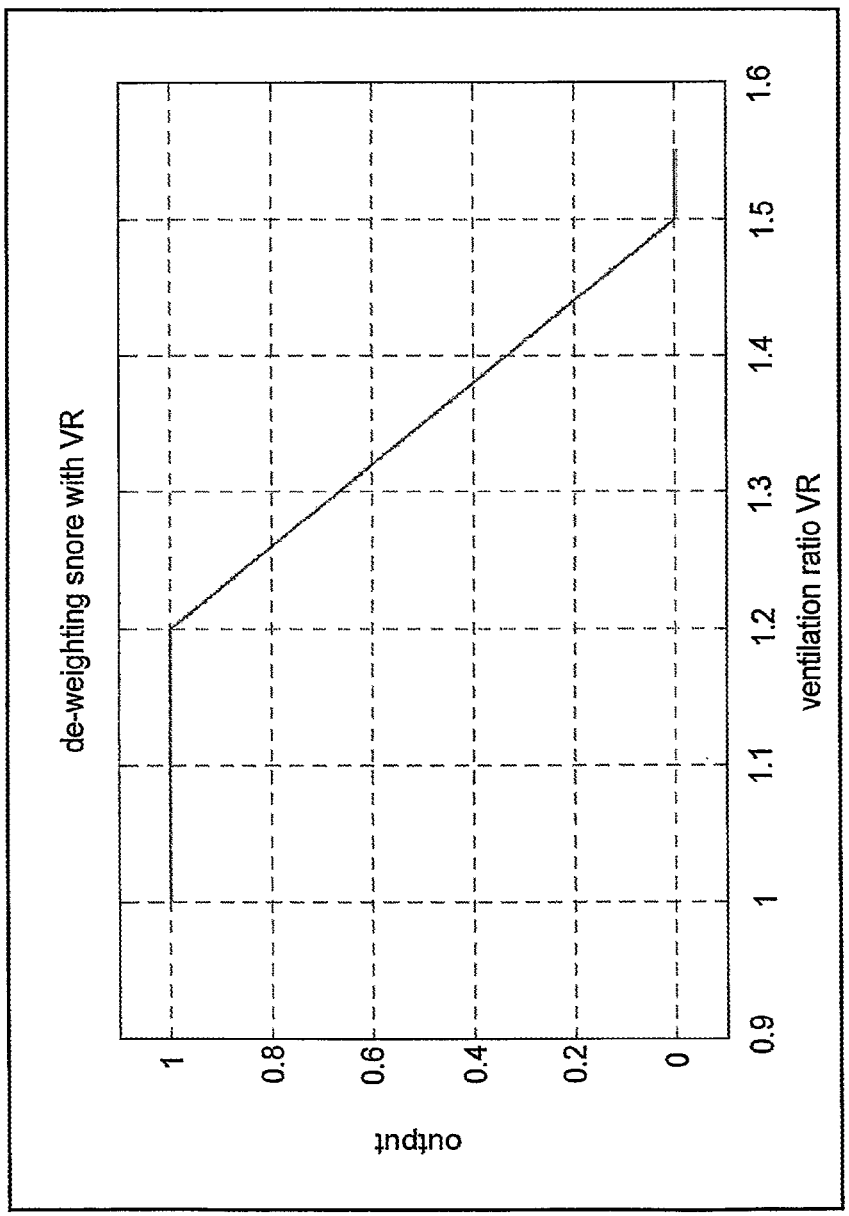
FIG. 37 is a graph of a function suitable for de-weighting a snore measure based on a ventilation measure indicative of a big breath.

The inspiratory snore index can also be de-weighted by a measure of ventilation such as a measure of a "big-breath." Big breaths often induce noise simply due to the high peak flows achieved. Utilizing the example function of FIG. 37, ventilation may be utilized to generate a de-weighting output factor depending on whether the ventilation measure is considered to be a big breath. For example, a ventilation measure such as the ventilation ratio (VR) may be used as a measure of big breaths. Values of VR greater than (>) 1 may be taken as indicating breaths that are large compared to the medium term ventilation. For values of VR less than (<) 1.2 the system may refrain from de-weighting any measure of snore and for values of VR greater then (>) 1.5 the system may completely de-weight the effect of snore. For values of VR between 1.2 and 1.5 the output de-weighting factor may decrease linearly from one to zero.

Other calculations to modify the effect of the flow limitation or snore based on the leak values, pressure, jamming and/or ventilation measures may also be utilized.

Section—I Normalized Expiratory Peak Location

A normalized expiratory peak location (NEPL) is a good indicator of a transition from sleep or obstructed sleep flow waveforms to waveforms indicative of wake, arousal or other unnatural, out-of-the-ordinary or unrecognizable events such as severe mouth leak. Thus, an apparatus of the present technology may implement a measure of arousal based on a peak expiratory flow. For example, depending on the location of a peak expiratory flow or normalized peak expiratory flow within an expiratory portion of a respiratory cycle, an arousal may be assessed. In such an embodiment, the time of the expiratory portion may be defined by ranges and the occurrence of the peak within the defined ranges defines an index that is indicative of arousal. The index may be indicative of arousal if the expiratory peak occurs in a latter time portion or range of the expiratory portion of the respiratory cycle.

Such an index may be calculated as follows:
1. Frame up breaths.
2. Isolate the expiratory portion of each breath.
3. Locate the time at which peak expiratory flow occurred.
4. Divide the time from the beginning of the expiration to the peak by the total expiratory time, e.g., the index is in the range [0.0:1.0].

Ordinarily when a patient is asleep the NEPL lies in the range zero to 0.3. For example, consider the histograms of FIG. 38 which show a comparison of three datasets corresponding to NEPL:

(1) Essen—OSA patients on treatment,
(2) Concord—patients being titrated, and
(3) Awake—people breathing on an AutoSet Spirit airway pressure device available from ResMed.

Figure 38:
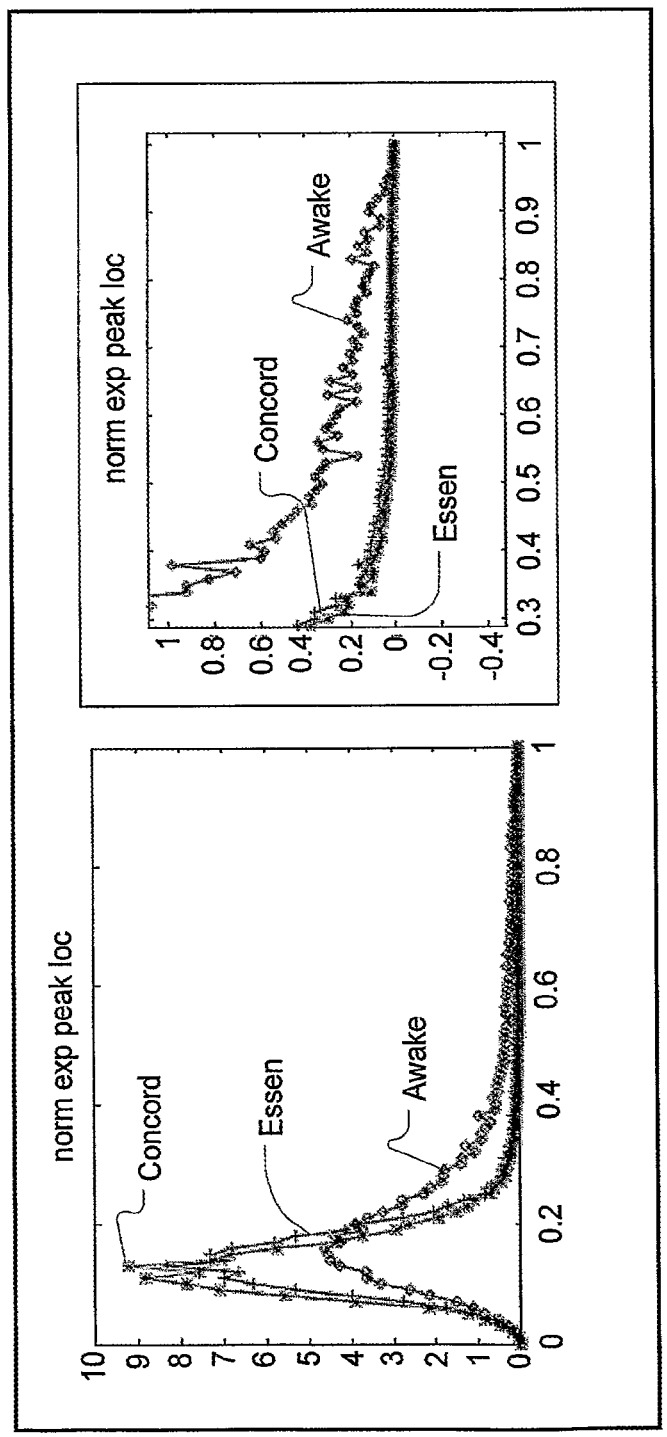
FIG. 38 is a histogram of normalized expiratory peak location for various groups of patients.
Figure 39:
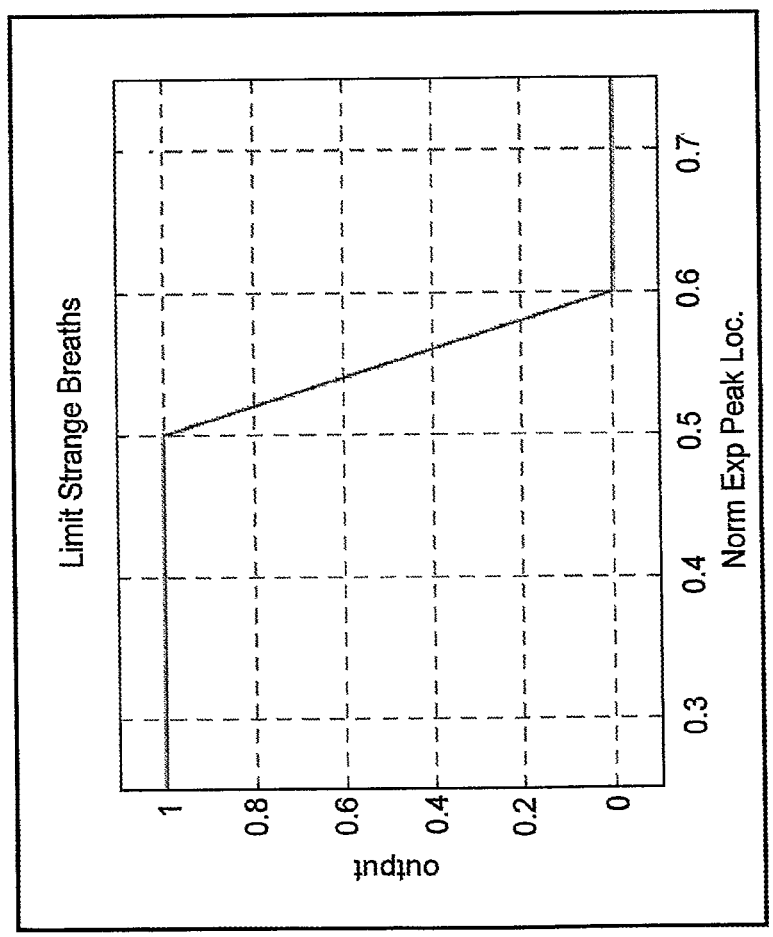
FIG. 39 is a graph of a function of a de-weighting factor to be applied to a flow limitation or partial obstruction measure based on a normalized expiratory peak location value.

The graph in the right-hand side of FIG. 38 shows that awake breathers have far more breaths with values greater than (>) 0.5 than the asleep patients who have few. Thus, a system can be implemented with a de-weighting function for a flow limitation measure based out-of-the-ordinary, unnatural or unexpected events with respect to sleep. A suitable function based on a calculated or determined normalized inspiratory peak location value is illustrated in the graph of FIG. 39. The function is used to increase the strength of the flow-limitation measure required to cause a rise in treatment pressure as the breath becomes more unnatural, out-of-the-ordinary or unrecognizable (e.g., weird).

In the foregoing description and in the accompanying drawings, specific terminology and drawing symbols are set forth to provide a thorough understanding of the present technology. In some instances, the terminology and symbols may imply specific details that are not required to practice the technology. Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements may be devised without departing from the spirit and scope of the technology.

For example, the desired flow limitation detection and/or treatment system can be based on other techniques for pattern recognition such as taking each inspiration and interpolating it over a grid of as many points as required to maintain important frequency information. For example, each inspiration may be interpolated over a grid of 65 points. A large set of training data may be developed with the different types of obstructed waveforms that can be recorded based on clinical evaluations. The waveforms may be pre-classified to categories such as mild, moderate and severe or other such category as desired. The 65 points of each waveform may then be input into a classifier for training (such as a neural network, support vector machine or other) and using an appropriate algorithm, such as one based on a genetic algorithm, arbitrary boundaries can be defined in the 65 dimensional space between the various categories of obstruction. Such a system would then be capable of classifying any inspiratory waveform measured in a patient against the metric of the classifier and used in a control system for treatment of the patient.

Some potential issues for consideration with the approach are as follows:

1. The "curse of dimensionality" refers to the exponential growth of hypervolume as a function of dimensionality. In other words, as the number of dimensions of our input space grow so the number of training vectors required to "cover" that space adequately grows exponentially. Covering 65 dimensions could present issues for the speed of the technology.

2. Pre-classifying waveforms as obstructive (and to what degree) is problematical and probably has a high interobserver variability. In the absence of raising the CPAP pressure to observe a waveform change such as "round up", it is difficult to determine whether obstruction actually exists. A reliable measure of effort, such as oesophageal pressure, can help with the detection issue but the problem of classifying such data in the determination can still be tricky. For example, REM sleep can produce different and unexpected waveforms.

3. The training phase would require "significant" numerical resources and lots of processor cycles.

4. The resulting classifier might be difficult for anyone to interpret and numerically intensive to run on an embedded system (depending, for example, on how many neurones we ended up with if using a neural network).

5. In order to test the resulting classifier we might need to feed it with the sleep studies everyone on the planet.

However, one way to reduce the complexity of the system is to limit the information fed into it to only that which is "interesting". The calculation of particular features, such as the flattening index, does just that; it acts as a form of compression of the signal.

The invention claimed is:

1. A method of detecting partial obstruction comprising:
   in one or more processors of a controller of a flow limitation detection device:
   receiving a measure of respiratory flow from a flow sensor;
   determining a shape index indicative of a pattern of partial obstruction from the measure of respiratory flow;
   determining a ratio of a current ventilation measure to a prior ventilation measure, the current ventilation measure calculated by dividing a total of inspired volume and expired volume of a current breathing cycle by a total of inspiratory time and expiratory time of the current breathing cycle;
   deriving a flow limitation measure as a function of the determined shape index and the determined ratio of ventilation measures; and
   affecting an output of the flow limitation detection device based on the derived flow limitation measure.

2. The method of claim 1 wherein the output is an indication of a detection of partial obstruction.

3. The method of claim 1 wherein the output is an indication of a quantified degree of partial obstruction.

4. The method of claim 1 wherein the output is an adjustment to a parameter of an operation of an associated respiratory treatment device.

5. The method of claim 1 wherein the pattern of partial obstruction is an M shape flow detection function.

6. The method of claim 5 wherein the prior ventilation measure is a recent medium-term ventilation determined by filtering the measure of respiratory flow with a time constant.

7. The method of claim 6 further comprising in the one or more processors calculating a pressure request as a function of the flow limitation measure.

8. The method of claim 7 wherein a processor increases a prior pressure request value based on (a) the shape index being indicative of a presence of an M shape breath in the respiratory flow and (b) the ratio of ventilation measures decreasing sufficiently to be indicative of less than normal ventilation.

9. The method of claim 8 further comprising in the one or more processors determining a second shape index indicative of a chair pattern of partial obstruction determined from the measure of respiratory flow and wherein the derived flow limitation measure is a further function of the second shape index.

10. A non-transitory information-bearing medium having processor-readable information thereon, the processor-readable information to control a processor for detecting respiratory partial obstruction with a flow limitation detection device, the processor-readable information when executed by a processor, perform at least the following:
    receiving a measure of respiratory flow in the processor from a sensor;
    determining a shape index indicative of a pattern of partial obstruction from the measure of respiratory flow in the processor;
    determining a ratio of a current ventilation measure to a prior ventilation measure in the processor, the current ventilation measure calculated by dividing a total of inspired volume and expired volume of a current breathing cycle by a total of inspiratory time and expiratory time of the current breathing cycle;
    deriving a flow limitation measure as a function of the determined shape index and the determined ratio of ventilation measures in the processor; and
    affecting an output of the flow limitation detection device based on the derived flow limitation measure.

11. The non-transitory information bearing medium of claim 10 wherein the output is an indication of a detection of partial obstruction.

12. The non-transitory information bearing medium of claim 10 wherein the output is an indication of a quantified degree of partial obstruction.

13. The non-transitory information bearing medium of claim 10 wherein the output is an adjustment to a parameter of an operation of an associated respiratory treatment device.

14. The non-transitory information-bearing medium of claim 10 wherein the pattern of partial obstruction is an M shape flow detection function.

15. The non-transitory information-bearing medium of claim 14 wherein the prior ventilation measure is a recent medium-term ventilation determined by filtering the measure of respiratory flow with a time constant.

16. The non-transitory information-bearing medium of claim 10 wherein the processor-readable information further comprises calculating a pressure request as a function of the flow limitation measure in the processor.

17. The non-transitory information-bearing medium of claim 16 wherein the processor-readable information comprises increasing a prior pressure request value in the processor based on (a) the shape index being indicative of a presence of an M shape breath in respiratory airflow and (b) the ratio of ventilation measures decreasing sufficiently to be indicative of less than normal ventilation.

18. The non-transitory information-bearing medium of claim 10 wherein the processor-readable information further comprises determining in the processor a second shape index indicative of a chair pattern of partial obstruction determined from the measure of respiratory flow and wherein the derived flow limitation measure is a further function of the second shape index.

19. A method of detecting partial obstruction comprising:
    in one or more processors of a controller of a flow limitation detection device:
    receiving a measure of respiratory flow from a sensor;
    determining a shape index indicative of a pattern of partial obstruction from the measure of respiratory flow;

determining a duty cycle measure from the measure of respiratory flow, the determined duty cycle measure being a ratio of a current duty cycle measure to a prior duty cycle measure, the current duty cycle measure being a ratio of inspiration time of a current breathing cycle to a total breath time of the current breathing cycle;

deriving a flow limitation measure as a function of the determined shape index and the determined duty cycle measure; and affecting an output of the flow limitation detection device based on the derived flow limitation measure.

20. The method of claim 19 wherein the output is an indication of a detection of partial obstruction.

21. The method of claim 19 wherein the output is an indication of a quantified degree of partial obstruction.

22. The method of claim 19 wherein the output is an adjustment to a parameter of an operation of an associated respiratory treatment device.

23. The method of claim 19 wherein the pattern of partial obstruction is an M shape flow detection function.

24. The method of claim 23 wherein the prior duty cycle measure is a recent medium-term duty cycle measure determined by filtering with a time constant.

25. The method of claim 24 further comprising calculating a pressure request as a function of the flow limitation measure.

26. The method of claim 25 wherein a processor increases a prior pressure request value based on the shape index being indicative of a presence of an M shape breath in respiratory airflow and an increase of the duty cycle measure.

27. The method of claim 26 further comprising determining a second shape index indicative of a chair pattern of partial obstruction determined from the measure of respiratory flow and wherein the derived flow limitation measure is a further function of the second shape index.

28. A non-transitory information-bearing medium having processor-readable information thereon, the processor-readable information to control a processor for detecting respiratory partial obstruction with a flow limitation detection device, the processor-readable information when executed by a processor, perform at least the following:

accessing in the processor a measure of respiratory flow;

determining in the processor a shape index indicative of a pattern of partial obstruction from the measure of respiratory flow;

determining in the processor a duty cycle measure from the measure of respiratory flow, the determined duty cycle measure being a ratio of a current duty cycle measure to a prior duty cycle measure, the current duty cycle measure being a ratio of inspiration time of a current breathing cycle to a total breath time of the current breathing cycle;

deriving in the processor a flow limitation measure as a function of the determined shape index and the determined duty cycle measure; and affecting an output of the flow limitation detection device based on the derived flow limitation measure.

29. The non-transitory information bearing medium of claim 28 wherein the output is an indication of a detection of partial obstruction.

30. The non-transitory information bearing medium of claim 28 wherein the output is an indication of a quantified degree of partial obstruction.

31. The non-transitory information bearing medium of claim 28 wherein the output is an adjustment to a parameter of an operation of an associated respiratory treatment device.

32. The non-transitory information-bearing medium of claim 28 wherein the pattern of partial obstruction is an M shape flow detection function.

33. The non-transitory information-bearing medium of claim 32 wherein the prior duty cycle measure is a recent medium-term duty cycle measure determined by filtering with a time constant.

34. The non-transitory information-bearing medium of claim 28 wherein the processor-readable information further comprises calculating a pressure request as a function of the flow limitation measure.

35. The non-transitory information-bearing medium of claim 34 wherein the calculating increases a prior pressure request value based on the shape index being indicative of a presence of an M shape breath in respiratory airflow and an increase of the duty cycle measure.

36. The non-transitory information-bearing medium of claim 28 wherein the processor-readable information further comprises determining a second shape index indicative of a chair pattern of partial obstruction determined from the measure of respiratory flow and wherein the derived flow limitation measure is a further function of the second shape index.

37. A method of determining a treatment setting for a respiratory treatment device comprising:

in one or more processors of a controller of a respiratory treatment device:

accessing a measure of respiratory flow;

from the measure of respiratory flow, determining a shape index representing a degree of partial obstruction;

from the measure of respiratory flow, determining a ratio of ventilation measures representing a degree of change in ventilation, the ratio of ventilation measures being a ratio of a current ventilation measure to a prior ventilation measure, the current ventilation measure calculated by dividing a total of inspired volume and expired volume of a current breathing cycle by a total of inspiratory time and expiratory time of the current breathing cycle;

calculating a treatment setting for the controller of the respiratory treatment device as a proportional function of both the degree of partial obstruction and the degree of change in ventilation; and setting the controller of the respiratory treatment device to control a treatment with the calculated treatment setting.

38. The method of claim 37 wherein the shape index is determined from a number of breaths in a range from 1 to 3 breaths.

39. The method of claim 37 wherein the shape index is an M-shape breath index.

40. The method of claim 37 wherein the treatment setting is applied by the controller to set an auto-titrating respiratory treatment device.

* * * * *